(12) United States Patent
Reiner

(10) Patent No.: US 11,974,861 B2
(45) Date of Patent: May 7, 2024

(54) NANOBOTS WITH EMBEDDED BIOSENSORS

(71) Applicant: Bruce Reiner, Berlin, MD (US)

(72) Inventor: Bruce Reiner, Berlin, MD (US)

( * ) Notice: Subject to any disclaimer, the term of this patent is extended or adjusted under 35 U.S.C. 154(b) by 220 days.

(21) Appl. No.: 17/712,693

(22) Filed: Apr. 4, 2022

(65) Prior Publication Data
US 2022/0225942 A1     Jul. 21, 2022

Related U.S. Application Data

(63) Continuation of application No. 16/503,920, filed on Jul. 5, 2019, now Pat. No. 11,324,451, which is a
(Continued)

(51) Int. Cl.
*A61B 5/00*     (2006.01)
*A61B 5/07*     (2006.01)
(Continued)

(52) U.S. Cl.
CPC .............. *A61B 5/6861* (2013.01); *A61B 5/07* (2013.01); *A61B 34/30* (2016.02); *A61B 1/041* (2013.01);
(Continued)

(58) Field of Classification Search
CPC ....... A61B 5/07; A61B 5/6861; A61B 5/0205; A61B 5/145; A61B 5/1455; A61B 5/067;
(Continued)

(56) References Cited

U.S. PATENT DOCUMENTS 8,235,055 B2 *   8/2012   Mintchev ........... A61B 5/14539
                                                    128/899
9,320,465 B2     4/2016   Kline
(Continued)

OTHER PUBLICATIONS

K. Ogawa et al.; "On-chip internalization process of an intracellular nanobot into a single cell"; 2017 IEEE 30th International Conference on Micro Electro Mechanical Systems (MEMS); 2017, pp. 581-584, doi: 10.1109/MEMSYS.2017.7863473. (Year: 2017).
(Continued)

*Primary Examiner* — Chu Chuan Liu
(74) *Attorney, Agent, or Firm* — Edwards Neils LLC; Jean C. Edwards, Esq.

(57) ABSTRACT

The present invention relates to a visualization system disposed in a human body, including, a nanobot configured to be disposed within the human body, the nanobot having at least one embedded biosensor, the biosensor which operates in real-time to continuously obtain data from within the human body; a visualization device configured to be integrated and/or embedded within the nanobot to provide real-time visualization data in the human body; a transmitter/receiver disposed on the nanobot which transmits data from the nanobot to an external transmitter/receiver, the transmitted data including the data from the biosensor and the data from the visualization device; and a processor configured to receive the data from the external transmitter/receiver of the nanobot and analyze the visualization data to determine the anatomic localization of the nanobot at a specific anatomic position within the human body.

20 Claims, 5 Drawing Sheets

Related U.S. Application Data continuation-in-part of application No. 15/632,817, filed on Jun. 26, 2017, now abandoned.

(60) Provisional application No. 62/694,248, filed on Jul. 5, 2018.

(51) Int. Cl.
  *A61B 34/30* (2016.01)
  *A61B 1/04* (2006.01)
  *A61B 10/04* (2006.01)
  *A61B 90/00* (2016.01)

(52) U.S. Cl.
  CPC ......... *A61B 10/04* (2013.01); *A61B 2034/303* (2016.02); *A61B 2090/3983* (2016.02); *A61B 2562/0285* (2013.01)

(58) Field of Classification Search
  CPC .............. A61B 5/14503; A61B 5/6867; A61B 2562/0285; A61B 2034/2051; A61B 2034/2055; A61B 2034/2063
  See application file for complete search history.

(56) References Cited

U.S. PATENT DOCUMENTS

2003/0214579 A1* 11/2003 Iddan ...................... A61B 5/07
                                                            348/81
2007/0225633 A1*  9/2007 Ferren ................ A61B 5/14546
                                                            604/27
2017/0119278 A1   5/2017 Hyde et al.

OTHER PUBLICATIONS

M. Pourhomayoun et al.; "Accurate Localization of In-Body Medical Implants Based on Spatial Sparsity"; IEEE Transactions on Biomedical Engineering, vol. 61, No. 2, pp. 590-597, Feb. 2014, doi: 10.1109/TBME.2013.2284271. (Year: 2014).

J. Li et al; Micro/nanorobots for biomedicine: Delivery, surgery, sensing, and detoxification. Science Robotics, 2(4), eaam6431; https://doi .org/10.1126/scirobotics.aam6431 (Year: 2017).

Non-Final Office Action issued in U.S. Appl. No. 16/503,920 dated Oct. 7, 2021.

* cited by examiner

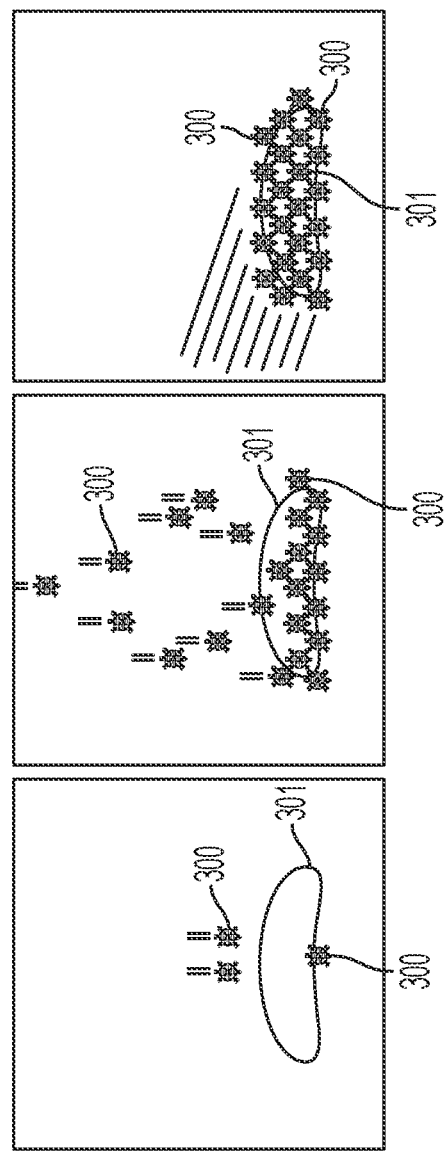

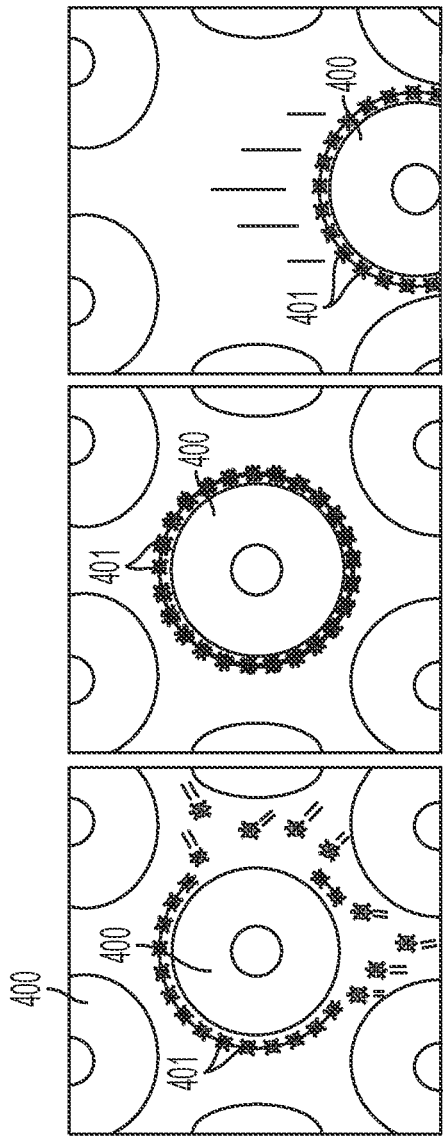
FIG. 4A
FIG. 4B
FIG. 4C
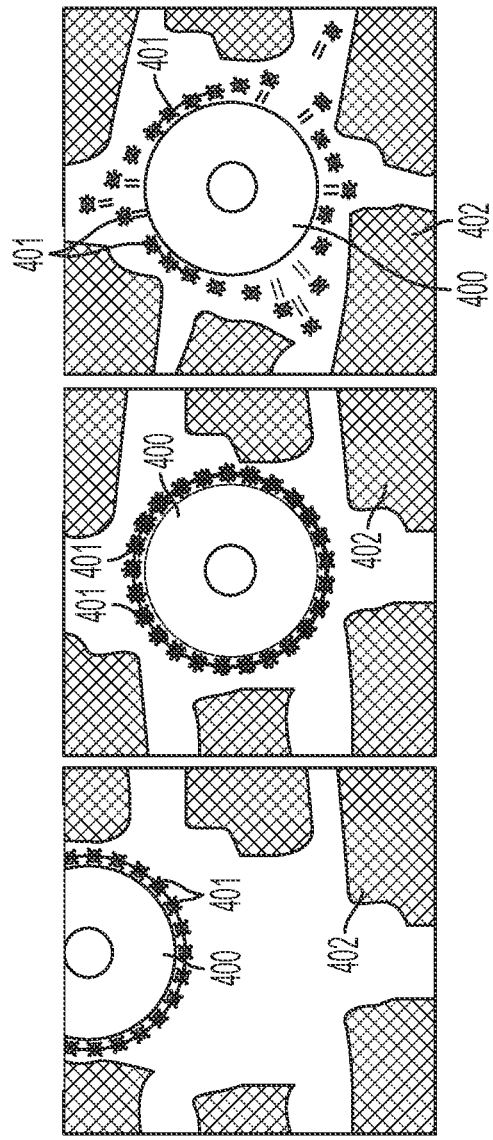
FIG. 4D
FIG. 4E
FIG. 4F

NANOBOTS WITH EMBEDDED BIOSENSORS

CROSS-REFERENCE TO RELATED APPLICATIONS

The present patent application is a continuation application of U.S. patent application Ser. No. 16/503,920, filed Jul. 5, 2019, which is a continuation-in-part (CIP) of U.S. patent application Ser. No. 15/632,817, filed Jun. 26, 2017, entitled "Embedded Biosensors for Anatomic Positioning and Continuous Location Tracking and Analysis of Medical Devices", and claims priority from U.S. Patent Provisional Application No. 62/694,248, filed Jul. 5, 2018, the contents of which are herein incorporated by reference in their entirety.

BACKGROUND OF THE INVENTION

Field of the Invention

The present invention relates to medical nanobots with embedded biosensors for real-time and continuous in-vivo anatomic localization, diagnosis, disease surveillance, and therapeutic intervention.

Description of the Related Art

Nanobots are miniaturized robots which typically have a size range of 0.01 to 0.1 micrometers and are constructed of nanoscale or molecular components. Other existing forms of microscopic devices also exist including microbots and micromotors, which are larger in size than nanobots and as a result, currently offer greater utility and practicality.

The integration of microscopic biosensors into bots provides a unique and expansive capability of performing a wide array of diagnostic and/or therapeutic functions; which can be applied to the living organisms, inanimate objects, or the local environment. Medical applications are an important application of the present invention.

SUMMARY OF THE INVENTION

The present invention relates to medical nanobots with embedded biosensors for real-time and continuous in-vivo anatomic localization, diagnosis, disease surveillance, and therapeutic intervention.

In one embodiment, the system of the present invention includes: a nanobot having at least one embedded biosensor, the biosensor which operates in real-time to continuously obtain data from within a human body; a transmitter/receiver disposed on the nanobot which transmits the data to an external transmitter/receiver; an anatomic localizer disposed within the human body; wherein the anatomic localizer provides data on its position within the human body to the nanobot and/or to the external transmitter/receiver; and a processor which receives the data from the external transmitter receiver, and which analyzes the data to determine anatomic localization of the anatomic localizer and the nanobot, and to determine a diagnosis of disease, and a therapeutic intervention.

Thus, has been outlined, some features consistent with the present invention in order that the detailed description thereof that follows may be better understood, and in order that the present contribution to the art may be better appreciated. There are, of course, additional features consistent with the present invention that will be described below, and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

FIGS. 3A-3C show a series of schematic diagrams of a bot

FIGS. 4A-4F show a series of schematic diagrams of a

DESCRIPTION OF THE INVENTION

The present invention relates to medical nanobots with embedded biosensors for real-time and continuous in-vivo anatomic localization, diagnosis, disease surveillance, and therapeutic intervention.

Bots

Figure 1A:
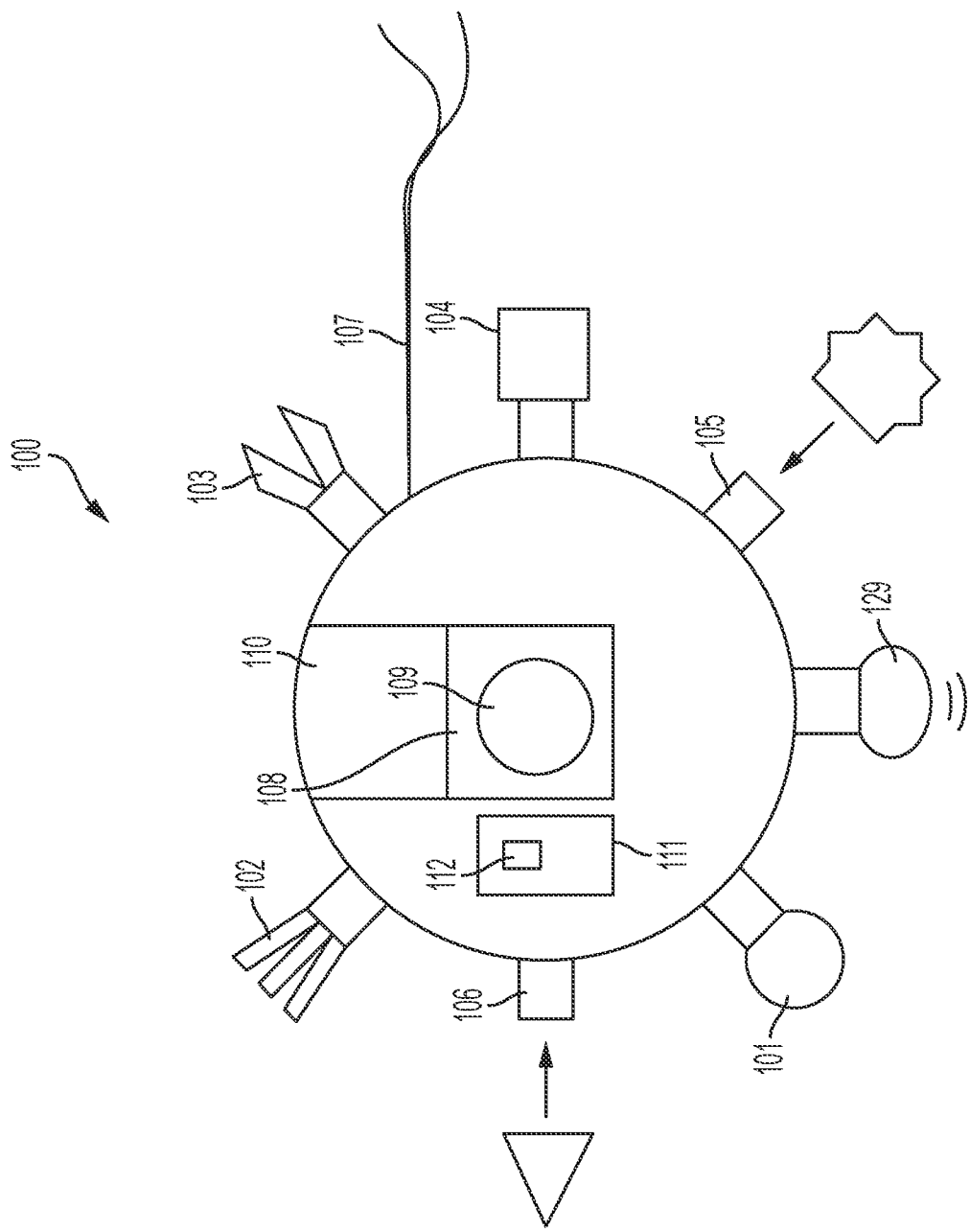
FIG. 1A is a schematic diagram of a nanobot according to one embodiment consistent with the present invention.

In one embodiment, a miniaturized robot 100 (i.e., microbot, nanobot) (see FIG. 1A) contains various types of embedded biosensors 102, 104, 105, 106 etc. (i.e., "smart bots") and other microscopic "appendages" (i.e., see camera 101, cutting implement 103, propulsion device 107, signal transmitter 129, etc., in FIG. 1A). The term "bot" 100 is used to describe various components of the present invention and includes all available forms of microscopic robots. These smart bots 100 provide for the creation of miniaturized devices 100 which can build, manipulate, or analyze data at an atomic level. When applied to the human body and medical applications, these smart bots 100 can exert their collective actions at the organ, tissue, cellular, or molecular levels.

In one embodiment, in addition to appendages, the bots100 may include a storage area 108 for an internal payload or sample 109, such as a sample of biological material. The attribute of an internal storage 108 provides for the bot 100 to have the ability to store the cellular or subcellular biological material 109 collected in-vivo, in order for the biological material 109 to be directly analyzed.

A variety of methods can be used to store and transfer these biologic specimens 109. In one embodiment, after sampling and storing the biological material 109 in the storage compartment 108, the sample 109 is retrieved by bot 100 elimination from the host.

Alternatively, in another embodiment, the bot 100 which performs the collection of a biologic specimen 109 could actively transfer the biologic material 109 to a secondary storage device 108 of another nanodevice (or a bot 100), which has a larger storage capacity capable of storing larger quantities of material from multiple individual microbots/nanobots. The transfer mechanism is accomplished by juxtaposing the two devices via location control mechanisms of the bots/devices, as further described below. The specific type of storage device, storage capacity, and ability to actively transfer biologic material are all properties which can be adapted to the user's requirements.

In one embodiment, the bot 100 is miniature in size, and able to travel throughout the body, but the size, morphology or composition of the nanobots is not strictly defined, as long as they can contain the desired embedded biosensors/appendages. Since the bots are miniaturized in size (i.e., nanotechnology), there is limited physical space to accommodate multi-functionality within an individual bot 100. While individual bots 100 may contain a variety of different types of miniaturized biosensors, for example, for performing bioassays, the ability to perform a wide array of other specialized functions (e.g., biopsy, cell/fluid collection, drug delivery, microsurgery), which are intrinsic to bot performance, these biosensors/appendages are not limited, and specialized bot functions may require the creation of dedicated bots, which add to bot diversity.

In one embodiment, the intrinsic differences in bot functionality, structure, and transporting capabilities may serve as a method for bot classification. Non-limiting examples of different types of bots of the present invention, and their functionality, include: Anatomic Scouts and Localizers; Specimen Collection and Retrieval (e.g., biopsy, aspirate); Microsurgery; Aggregator (Coalescence of multiple bots); Storage (Biologic Material, Drugs—both entry storage functions (i.e., antibiotics for delivery) and exit storage functions (i.e., biopsy specimen); Destroyer ("Killer") (Physical destruction of (faulty) bots); Anti-Bleeding (Cauterization, Embolization); Drug Delivery; Non-surgical Intervention (Radiation, Cryotherapy, Electromagnetic, Stem Cell Delivery/Injection); Quality Assurance and Quality Control; Communication (Data Delivery and Transmission or receipt of data to/from other bots); "Smart" Supervisory (Directs/Redirects Bot Actions or Tasks performed in accordance with real-time data, for example); and Therapeutic Deployment (e.g., delivery of radiation, cryotherapy, electromagnetic pulse, stem cells, etc.).

In the embodiments of the present invention, the above classifications are not intended to be complete but instead provide a broad list of functional applications for descriptive purposes. In addition to classification schema based upon function, bots used in the present invention can also be categorized in accordance with other attributes such as size, structure, mobility, organ system/anatomic coverage, and adaptability.

In one embodiment, the physical, mobility, and functional characteristics of microbots/nanobots will often dictate the local milieu in which they can operate. As a result, some microbots/nanobots may selectively operate in one organ or anatomic system, while other microbots/nanobots may have greater versatility and applicability. Any anatomic specificity of microbots/nanobots may serve as an additional method for categorization.

In one embodiment, while some microbots/nanobots may operate in a completely independent fashion, others may have the capability to operate in conjunction with other microbots/nanobots, which may prove to be particularly beneficial when successful task completion requires large numbers of individual microbots/nanobots to operate in unison. In certain applications, microbots/nanobots may be required to physically attach to one another (i.e., coalescence or aggregation), in order to complete a designated action (e.g., macrocytic phagocytosis, embolization). This ability to indirectly or directly operate in a synchronous fashion with other microbots/nanobots also serves as a differentiating quality and source of classification.

In one embodiment, in addition to these individual specialized functions, some bots of the present invention possess the ability to perform multiple functions and would therefore be classified as "multi-functional bots" (discussed further below).

In one embodiment, the bots of the present invention can also be categorized in a more structural and intrinsic way, to include functional and interactive components. The Classification Schema and Functionality of the Bots may include, in addition to Mobility, Size, Morphology, Storage, and Aggregation, as discussed above, but also: Functionality (Diagnostic versus Therapeutic), Independence, Communication, Visualization, Sampling, Sensor technology, Anatomy Specificity, Intervention, Elimination, Adherence, Measurements, Artificial Intelligence, and Anatomic Localization.

In one embodiment, the bots 100 accomplish their tasks by having their own internal electronics, such as an internal microprocessor 111 and memory 112, which runs a program to handle various bot 100 operations, including certain specific tasks such the bot propulsion mechanism 107, or other features of the bots 100—i.e., cutting implement 103, etc.

Figure 1B:
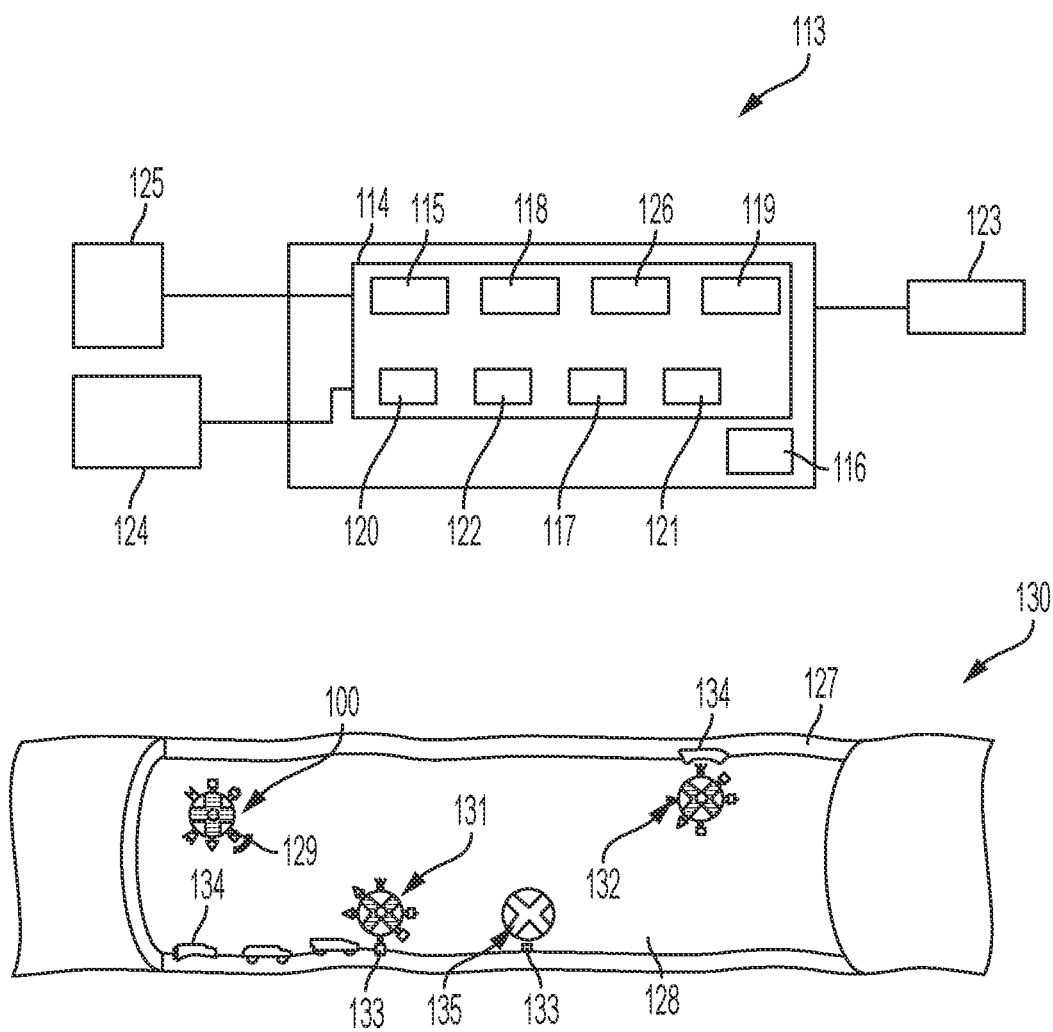
FIG. 1B is a schematic diagram of the electronics of the present invention which operates to provide operational control of said nanobot of FIG. 1A, while said nanobot moves throughout the human body, according to one embodiment consistent with the present invention.
Figure 2A:
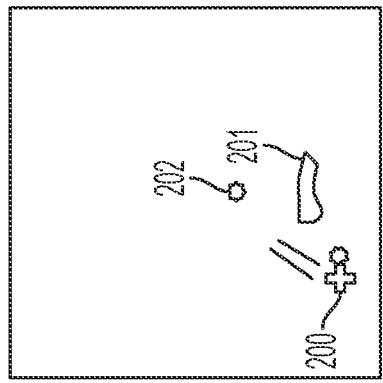
FIGS. 2A-2F show a series of schematic diagrams of a bot approaching a cellular material in a human body, according to one embodiment consistent with the present invention.
Figure 2B:
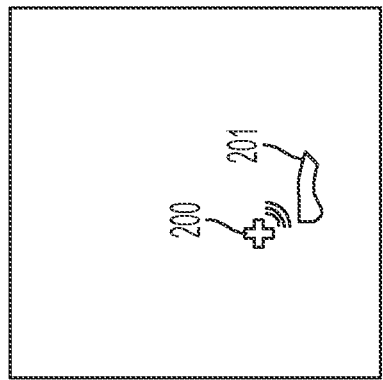
Figure 2C:
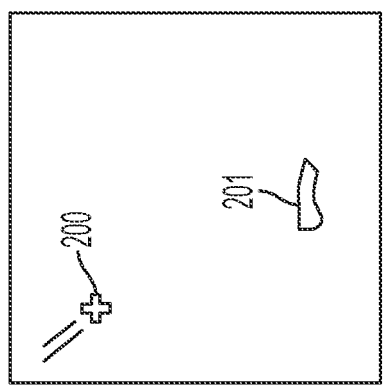
Figure 2D:
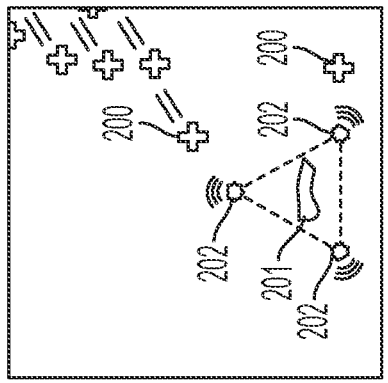
Figure 2E:
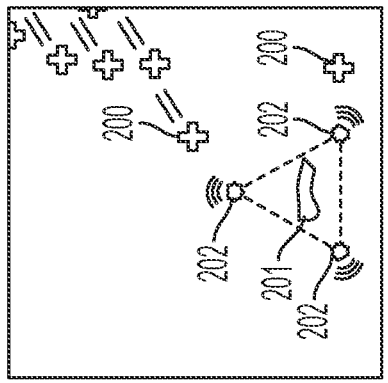
Figure 2F:
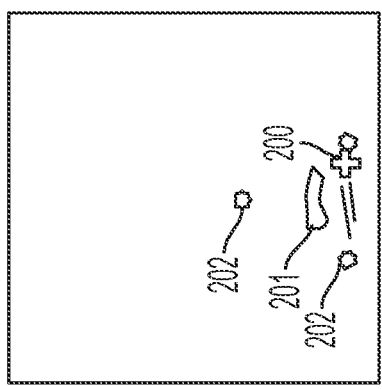

In one embodiment, the bots 100 are directed externally, from a computer system 113 (see FIG. 1B), having a processor 114, memory 115, with various program modules 116-122, input/output interface 116, display 123, external data storage 125, and a software program which runs the various bot operations. The computer system 113 interfaces with the bots 100 via a transmitter/receiver 124 (wireless, internal or external), which receives wireless signals from the transmitter 129 on the bots 100 within the system 128 (i.e., blood, etc.) of a patient body 127, and sends them to the receiver 124, which forwards the signals to the processor 114 for analysis.

The various attributes of the present invention are discussed below.

Mobility

In one embodiment, an important distinguishing feature of the bots 100 is their mobility, which can be broadly defined by two different groups; those which rely on passive movement through the medium (i.e., blood 128) in which they reside and those which have the capability of active movement through self-propulsion (i.e., via propulsion tail/device 107). Active movement has a number of distinct advantages, the most notably of which is the ability to travel through most in-vivo environmental conditions, and the second is the ability to actively travel to a predefined anatomic location. Along the same lines, are size and morphology which as physical attributes, also define the characteristics of bots in navigating within various anatomic locations and sequestering within a designated cellular or subcellular location.

In one embodiment, in the medical field, bots can be created in both passive and active modes of operation. Passive bots are designed to be transported via intrinsic naturally occurring flow media 128, such as the bloodstream, lymphatics, gastrointestinal tract, airways, or cerebrospinal fluid. In passive transportation mode, the bots 100 travel in concert with intrinsic flow and/or pressure inherent to the medium 128 or tissue in which it is positioned. In the human body 130, examples of such media 128 include (but are not limited by) the bloodstream (arteries, veins, capillaries), lymphatics, cerebrospinal fluid (CSF), gastrointestinal (GI) tract, genitourinary (GU) tract, biliary system, and respiratory tract. In these systems, bots 100 would passively navigate in accordance with the volume, pressure, and directionality of the media 128 in which it is contained.

In some pathologic cases however, organ/tissue systems which are normally devoid of internal flow may have underlying pathology which creates flow/pressure where it should not normally exist. As an example, if a bronchopleural fistula was present (which is an abnormal connection between the lung bronchus and the pleural space), intrinsic flow within the bronchus would be transmitted into the pleural space which is normally devoid of internal flow/pressure. As a result, bots 100 located in the pleural space in the setting of a bronchopleural fistula would now be subjected to pressure and passive movement. This can serve as an important diagnostic tool, for the resulting bot movement and pressure (which can be measured by embedded biosensors (i.e., sensors 102, 106 etc.)), can both be used by the diagnosis module 120 of the computer system 110, so that the program can diagnose the underlying pathology while simultaneously quantifying its severity by analyzing the measurements of the abnormal flow and pressure within the pleural space.

In one embodiment, active bots 100 have the inherent capability of self-propulsion (see propulsion device 107 or tail 107 in FIG. 1A), and as a result can actively transport the bots 100 in anatomic locations devoid of intrinsic flow (e.g., hollow viscera (e.g. bladder, gall bladder), pathologic fluid collections (e.g., hematoma, abscess), or non-mobile tissue (e.g., skin, skeletal structures)). Active bots 100 can also be used to navigate through space in the opposite direction of intrinsic flow, as in the example where bots travel in the bloodstream in a direction opposite to normal blood flow. (As an example, when embedded biosensors 102, etc., are used to detect flow directionality, turbulence, pressure, and/or velocity).

In one embodiment, the program can record the bot's 100 time-stamped location at the time of biosensor data collection. In active transportation mode, the bots 100 would rely on intrinsic energy contained within the bot 100 or contiguous structures to propel the bot 100 in a direction of its choosing. Active transportation mode of bots 100 would be routinely required in the absence of intrinsic organ/tissue flow (e.g., peritoneal cavity, pleural space, internal auditory canal, hematoma).

In one embodiment, bots 100 can also be stationary in position (i.e., static transportation—see bot 131 in FIG. 1B, for example), in which they remain in a fixed location. This takes on importance when, in one embodiment, continuous data over time is required at a fixed anatomic location, thereby providing longitudinal data for temporal analysis by the program. In the previously cited example of analysis of sepsis, continuous biosensor derived data of inflammation markers when analyzed by the program, provides important insights as to the phase, severity, disease progression, and response to intervention (e.g., antibiotics).

Anatomic Localizers

The ability to direct bots 201 (see FIG. 1B) to a specific anatomic location 131 is another important feature of the present invention. A variety of methods can be employed by the present invention for bot localization, which in some respects may be analogous to global positioning satellite (GPS) inside the human body. The net result is the program's creation of a real-time three-dimensional (3D) bot 100 localization tool (i.e., location module of computer system 113), which can be continuously updated in accordance with bot 100 movement.

In prior art systems, while existing circulating bots can provide cursory anatomic localization of abnormal data recorded (for example, which can be made optimally localized by combining synchronous data from multiple bots at a variety of locations), existing bots are limited in their ability to closely and accurately monitor subtle changes in data over time.

The present invention solves this problem by directing circulating bots 131 to a specific anatomic location 133 using a signal device 133 implanted in the wall of the medium 128, or by transmitting a signal to the bot 100 from transmitter/receiver 124 or internally from transmitter/receiver 129.

In one embodiment, in order to direct the bots 100 to the specific anatomic site of interest through the deployment of anatomic markers 133, the marker 133 has the ability to emit a specific tracking signal (e.g., light, sound, temperature). This signal would in turn could be received by the bot 100 which has been equipped with a receiving sensor 129. Upon successful transmission and receipt of the anatomic localization signal, the corresponding bot 100 could engage at the specific anatomic site of interest 133 and perform its designated function (e.g., bioassay). Certain bot performed functions (e.g., biopsy, drug release) may require third party confirmation of successful anatomic localization between the anatomic localizer and bot before the bot can be actively engaged and perform its duties.

In one embodiment, once at the anatomic site of interest 133, continuous data collection by the bot 100 can be obtained over a defined time period, which can be correlated by the software program with comparable data measurements from neighboring bots also in fixed nearby anatomic locations.

As noted above, in order to ensure the anatomic localization of these bots 131 is accurate, in one embodiment, the signal device 124, 129 can be used to guide bot migration to the specific location 133 of clinical interest. Examples of such signaling devices 124, 129, which may be external or internal, may include (but not be limited to) emitters of electromagnetic pulses, microwaves, light, sound, or vibration. For example, these deployed anatomic localizers 133 may elicit a specific radiofrequency which is received by selected microbots/nanobots 100, which in turn can be driven to the specific site of anatomic localization. The radiofrequency of the signal being emitted is specific to the individual class or functionality of microbots/nanobots 100 required to perform the requisite task.

In one embodiment, these anatomic localizing "emitters" 129 can be performed by specialized "deployment" bots, which are directed or programmed (via internal microprocessors 111 which propel the bots 100) to deliver the emitter 129 to a specific anatomic location (i.e., location marker 133) based upon the collective data analysis of circulating bots 100 by the software program. Once the specific anatomic location (i.e., location 133) is determined by a location module 120 of the computer system 113, the deployment bot is transported to the region of anatomic concern by the signal device 129, and deposits a series of emitter devices or location markers 133.

In one embodiment, the positional relationships between the bot 100 and fixed anatomic marker 133 can be established in a variety of ways. In one application, as noted above, the bot 100 can emit a signal (e.g., ultrasound, photo-magnetic pulse, light, thermal) which will be received by sensors embedded in the fixed anatomic markers. Based upon the signal magnitude, time (between signal transmission and receipt), and direction, an anatomic vector will be created by the location module 120 which determines the specific location and distance between the two entities.

In one embodiment, direct visualization tools can also be directly integrated into microbots/nanobots 100, as another method for anatomic localization, and the local deployment of anatomic markers 133 serves as an in-vivo guide to circulating microbots/nanobots 100 to direct them to a specific anatomic site of interest.

In one embodiment, a method of accomplishing this task would be through the creation of a unique signal upon successful anatomic registration of the two entities (i.e., bot 100 and anatomic localizer 133), which would be transmitted via wireless technology using a signal transmitter/receiver 129, to the receiver 124 of the computer system 113 of the authorized third party. Upon successful receipt of the unique signal, the authorized third party can in turn transmit a unique signal back via transmitter/receiver 129 to the bot 100 which would confirm successful anatomic localization using the location module 120, and approval of instituting the defined bot action. This serves as a quality assurance measure for patient safety and bot performance, which is of particular importance for those actions in which incorrect anatomic location could result in a deleterious outcome to the patient and local anatomic milieu.

In one embodiment, as long as these emitting devices 133 are biodegradable, no formal retrieval process is required. If, however, the emitting devices 133 are not biodegradable, retrieval would be required, which could be accomplished through either manual extraction (with the extraction device guided to the specific site by the emitter) or through detachment and excretion (e.g., urinary, gastrointestinal). The method for deployment of these emitters 133 may vary in accordance with the anatomic structure/tissue in which it is localized. Retrieval is discussed further below.

In an exemplary embodiment, deployment of a bot 100 in a blood vessel wall 127 may be performed via a suturing technique in which the microscopic transmitter/localizer device 133 is sutured to the blood vessel wall 127 as a fixed anatomic markers 133, to provide an anatomic reference point for nearby bots 100 (which may be stationary or mobile), of the location of a cellular material 134, for example. If the desired location is within a solid organ (e.g., liver), the transmitter device 133 may be deployed though injection (performed by the delivering bot armed with a needle driven delivery device). The anatomic relationship of bots 100 relative to these fixed anatomic markers 133 can be periodically monitored by the location module of the computer system to determine the specific location of each individual bot 100 at a single point in time, the three-dimensional distance of the bot 100 from the anatomic marker 133, the velocity of the bot (when mobile), and the directionality of bot movement (when applicable).

Since these emitting devices 133 may become dislodged and become mobile, the present invention includes integrating an internal motion sensor into the transmitter 129 design of the bot 100 so as to alert the end-user by electronic means (i.e., alarm on a display 123, text, etc.) when it becomes detached from its intended stationary location. At this point in time, the emitting device 133 is no longer serving its intended function (of directing bots 100 to the desired anatomic location), and in the present invention, can be effectively disarmed (i.e., turned off from emitting signals) so as to prevent unintended bot migration to an incorrect anatomic location.

In one embodiment, in the case of migratory bots, data is continuously being recorded in a database 115 of the computer system 113, commensurate with bot and embedded biosensor functionality. In addition to biosensor-derived data, anatomic localization of the migrating bot 100 is important in order to accurately determine the location of abnormal data. Once an abnormal data is transmitted and the measurement is received and recorded by the program in the computer system database 115, the data can be verified by the location module 133 cross-referencing the data abnormality with comparable data from neighboring or nearby bots 100 in the same time period. If the abnormal data is confirmed by the program, it is important to accurately localize the source of the abnormal data.

In one embodiment, in the case of a mobile or migratory bot, successive signal analysis by the program can provide additional data related to velocity and directionality of bot 100 movement over time, relative to the fixed anatomic marker 133. Since the number of bot signals being transmitted by the transmitter 129 to the fixed anatomic marker 133 may be quite numerous, each individual bot's 100 signal would have its own unique characteristics to differentiate it from nearby bots 100 which are simultaneously emitting signals.

In one embodiment, in order to accommodate extremely large numbers of bot signal transmissions, each fixed anatomic marker 133 would have a large number of embedded sensors capable of receiving these signals and the specific three-dimensional location of each receiving sensor would be accessible via a defined anatomic marker sensor roadmap which can be stored in memory 115 and displayed for the user on a display 123. In many instances where bots 100 are being transported at fairly high velocities (e.g., bloodstream), simultaneous transmission signals may be sent from a single bot 100 and received by multiple fixed anatomic markers 133. This ability to cross reference anatomic localizing data from multiple fixed anatomic markers 133 by the location module 120 provides for increased accuracy in 3D bot localization.

In one embodiment, each individual anatomic localizer 133 may have its own unique signal, which can be used to attract specific types of bots 100 commensurate with the desired action to be performed. The localizer 133 may be used to direct different types of bots to anatomic locations of interest—i.e., direct diagnostic bots 100 to the anatomic location of interest for continuous bioassay data collection; another localizer may be used to direct bots capable of local cell/tissue collection; and another localizer used to direct therapeutic bots for local drug delivery.

In a continuation of the previous example of a bot in a blood vessel, traveling to a location marker in the liver, it is noted that a sudden increase in local inflammatory biomarkers may indicate either an intratumoral inflammatory response to chemotherapy or a localized infection, both of which can be treated through local release of anti-inflammatory agents or antibiotics (via the therapeutic capabilities of bots). Alternatively, if the inflammatory biomarkers are systemic (as evidence by release of biomarkers far away from the tumor site), this may be an early harbinger of remote infection which could easily lead to life threatening sepsis in an immunocompromised patient. In one embodiment, by the program determining the general location of circulating bots 100 which first detected this elevation in inflammatory biomarkers, the location module 133 can begin to identify the anatomic location of the developing pathology, and the program can be used to identify the specific inflammatory etiology, determine the severity of disease (through continuous data collection at the infection site), and response to intervention.

In another exemplary embodiment, suppose an abnormal bioassay has been detected in the liver in closest proximity to an anatomic localizer in segment VI (using the Couinaud anatomic classification of segmental liver anatomy). Since both the right portal and right hepatic veins are relevant nearby anatomic structures in segment VI if the right hepatic lobe, which also serve as directional conduits throughout the liver, fractional bioassays obtained within these venous structures can be used by the localization module 120 to define the specific anatomic location of greatest interest.

In one embodiment, if localizing coordinates within these veins are created at 1 cm intervals, the specific locations which recorded the highest bioassay measures as determined by the program, can be transmitted to the circulating bots 100 for optimal localization. As numerous bots 100 are directed to the anatomic locations of interest, new bioassays are performed by the program to confirm the abnormality in question, record the severity of the abnormal biomarker, track temporal change, and refine the anatomic location by determining both the epicenter in which the highest measure of the abnormal biomarker is recorded, as well as the peripheral anatomic boundaries in which the abnormal biomarker measurements return to normalcy.

In one embodiment, since these anatomic markers 133 will define the area of anatomic interest in three dimensions (by using simultaneous data recordings from the right hepatic vein, right portal vein, corresponding venues, and capillaries), in the present invention, additional anatomic markers (e.g., biodegradable surgical clip, suture) can be deposited in the corresponding walls of these structures, which contain sensors capable of emitting unique signals for future anatomic location tracking and directional assistance.

Communication

In one embodiment, through the use of wireless technologies, communication between bots 100 and authorized end-users can readily occur. In the present invention, these communication protocols first require verification and authentication of the involved parties to ensure that the communication is properly authorized. This communication and contained data can lead to the creation of local area network (LAN) within the host subject (i.e., body area network), which in turn can communicate with local, regional, or distant centralized data networks for larger scale data storage and analysis from single or multiple data sources.

In order to externally (or remotely) direct circulating bots 100 to a given anatomic location and function, a communication system must exist which allows an authorized end-user to selectively transmit a signal to those bots 100 capable of performing a desired action (either diagnostic or therapeutic) and directing them to the specific anatomic location of interest. As noted above, the communication system can be predicated on creating a unique radiofrequency for each individual bot function and category. The authorized end-user can then input the specific functional requirement (e.g., biopsy, bioassay) and the number of required bots 100 to satisfactorily complete the required task. The appropriate radiofrequency signal is then transmitted from the computer system 113 to "qualified" bots 100, which in turn are required to transmit a "received and acknowledged" signal from transmitter/receiver 129 back to the computer system 113.

In one embodiment, upon successful verification, the authorized end-user will then submit the anatomic location data of the desired action to be performed. Once the "qualified bots" 100 reach the intended anatomic location, a signal is emitted to verify their current location to ensure that the anatomic location of record matches their current location, as determined by the program. In many circumstances, a local "on site" bot(s) 100 and/or anatomic localizer 133 will assist in exact localization. In all situations, multi-directional communication is required to ensure the recruited bots 100 have the appropriate functionality. These "qualified" bots 100 have successfully received and acknowledged the required action, the anatomic location has been verified and successfully navigated, and a final directive of authorization is sent by the program and received by involved and authenticated parties.

In one embodiment, each individual bot is assigned its own unique identifier, which is important for identification, tracking, functional analysis, quality control, anatomic localization and steerage, and communication. In addition to unique individual identifiers (for each specific bots), the identifying information and corresponding signal frequencies used for communication can also be applied to the specific classification scheme (i.e., categorical type of bots), anatomy/organ system in which it is designed to function, specific type of diagnostic or therapeutic actions it is designed to perform, biosensors and/or other embedded tools, and communication capabilities. The present system allows bidirectional communication between in-vivo bots and authorized external sources (e.g., physician, biomedical engineer, scientist) or between in-vivo bots in which individual and/or specific groups of bots can be continuously tracked by the program for anatomic location, directed to alternative locations, instructed as to tasks requiring performance (or cessation), monitored for quality assurance/quality control, and data transfer.

In some select cases, communication can also exist between authorized bots 100, and not necessarily require direct human input. Since the level of sophistication in these communication capabilities may be highly variable in nature, the communication technology and protocols used may be another way in which bots 100 can be categorized.

Since thousands (or even millions) of individual bots 100 may be contained within a single host source at any single point in time, it is important that the communication protocols used have the capability of correctly identifying either an individual or small group of bots 100 specific to the communication and/or task of record. In one embodiment of the present invention, the manner in which this selective bot communication can occur is through the creation of a unique electronic signature (e.g., operating frequency) for each individual bot 100, which provides each individual bot 100 with a secure method of identification, data security, transmission, and receipt to/from the transmitter/receiver 124 and the computer system 113.

In one embodiment, in addition to solo operational mode where each bot performs its own independent actions, bots can also operate in group mode where multiple bots act in a collaborative fashion to fulfill a designated task. This "group mode" of operation is of particular importance when the desired action is beyond the scope, time, magnitude, and/or physical capability of a single bot.

Further, in addition to individual bot-specific electronic signatures, in one embodiment of the present invention, pools of bots 100 can have a shared electronic signature (e.g., based on bot classification, functionality, and mission), thereby providing a method for "group" communication and data sharing. Before common data is shared between individual bots 100 within a shared communication network, the present invention requires a security feature to be elicited to ensure that data being sent or received via transmitter/receiver 124 is first validated to ensure authenticity, integrity, and security clearance of the data source or party receiving the data.

In one embodiment of the present invention, there are two distinct options available for "group" bot communication. In the first option, individual bot-specific signals are transmitted to all verified bots 100 which fulfill the criteria of interest. In the second option, a single specialized signal is transmitted which accounts for all bots 100 within a designated class. These classes may be predefined at the time of bot conception or defined "after the fact", in accordance with the clinical situation at hand.

In one embodiment of the present invention, in order to newly create "group" bot signals, authorized end-users (at least two different authenticated users) identify the individual bots 100 within each desired group and create a unique signal frequency which can be simultaneously transmitted to all corresponding bots 100. The new group signal transmission will contain the specific anatomic location of interest, specific task to be performed, date and time of the occurrence, and duration of activity. If any inter-bot communication is required, the specific identities of the corresponding bots 100 will be included.

In one embodiment, before any action is to occur, the bots 100 receiving these transmissions must first acknowledge receipt of the transmission and acceptance of the task. Once these signals and instructions have been received and acknowledged by the program, all verified bots 100 within the group can now respond to a single "group specific" signal for further transmissions. In the event that any individual bots are non-compliant with the requested action or become disabled as determined by the program (i.e., lack of signal response or verification etc.), they can be removed from the group transmissions by the program by eliminating from the group (the directive of which is performed through their unique individual signal frequency). In this manner, authorized end-users can continuously monitor the actions performed, and modify group directives in accordance with changes in patient status and/or required compensatory actions. This illustrates how the present invention can be used to accommodate communications with bots on both individual and group bases.

In one exemplary embodiment, suppose a critically ill cancer patient with a depressed immune status is found to have a rapid rise in temperature, leukocytosis (i.e., elevation in white blood cell count) and early signs of sepsis. The only realistic way to treat the patient before they succumb to their illness would be to promptly identify the anatomic source of infection, identify the offending pathogen, identify antibiotic sensitivity of the pathogen, and locally deliver high doses of the optimal antibiotic. These multi-functional requirements would take a synchronized effort of multiple bots, with different bot groups performing different functions. In order to synchronize these divergent tasks, the program of the present invention would be instructing different bot groups accordingly, and would have the bot groups staged in a sequential fashion: first identifying the anatomic site of interest; then obtaining cell/tissue specimens for culture and sensitivity; and then local delivery of the optimal antibiotic regimen.

In one embodiment, one example of a clinical scenarios in which coordinated bot "group mode" may be required may include a severe infection (e.g., abscess), in which therapeutic drainage would require the coordinated action of hundreds (or thousands) of individual bots in order to completely drain the volume of infected material.

In another exemplary embodiment of coordinated, not "group mode", of action, may be in response to a toxic biologic exposure which encompasses a large anatomic region (e.g., lung fields) or multi-organ involvement (e.g., cardiovascular system). In these scenarios, the diffuse nature of exposure to the environmental or toxic agent would require rapid diagnostic and/or therapeutic response which may entail millions of bots acting in unison, with some performing diagnostic actions (e.g., bioassays, specimen collection), and others performing therapeutic actions (e.g., drug delivery, sequestration of toxins).

As previously discussed, group communication may be accomplished through a shared radiofrequency. Since large number of bots may encompass large anatomic regions and/or multiple organ systems, compartmentalization or subgroups may be required to coordinate action within a limited anatomic region. In this scenario, a number of individualized subgroups may be designated which provides both a method for targeted communication as well as data collection and analysis. In the example of a toxic inhalation affecting the entire lung fields, coordinated bot subgroups may be defined in accordance with segmental lung anatomy (e.g., apical segment right upper lobe, posterior basilar segment left lower lobe). By subdividing the anatomic region of clinical concern into subgroups, it becomes easier to delegate, manage, update, and react to ongoing clinical changes, while also segmenting and analyzing data, which may vary among different anatomic regions.

In one embodiment, the data derived from bots (either acting independently or in concert with one another) may also be shared, cross referenced, and communicated with other authorized medical devices (e.g., cardiac pacemaker, insulin pump, vascular catheter). This provides a methodology for longitudinal real-time analysis by the program of multifunctional and multi-organ system data, which can lead to synchronized data analysis and intervention throughout the entire host biologic milieu.

As an example, suppose a diabetic patient who is normally well controlled is found to be acutely develop severe hyperglycemia and diabetic ketoacidosis. The first course of action is to ensure that the patient's insulin pump is properly working, and the correct amount of insulin is being delivered. By the program mobilizing diagnostic bots to the anatomic location of interest (i.e., pancreatic veins), serial measures of insulin can be collected to ensure that the pump is properly functioning, and the released insulin levels are consistent with the prescribed baseline levels.

Once the program has confirmed that the insulin pump is not the source, a number of other potential causes may be explored. These would include (but are not limited to) underlying infection, emotional stress, medication related, trauma, stroke, and heart attack. While medications can be readily excluded (by the program correlating with the patients' medical record and list of administered drugs), the other potential etiologies may be analyzed by the program through bot detected bioassays for a variety of disease-specific biomarkers. Examples may include C-reactive protein, lipoprotein associated phospholipase A2, and urinary albumin for stroke, troponin, myoglobin, modulated albumin for myocardial infarction, and procalcitonin, soluble triggering receptor on myeloid cells, human neutrophil lipocalin for infection. Coordinated bot derived bioassay data offers the potential for both earlier and more accurate diagnosis, anatomic localization, and the ability for early and targeted intervention.

At the same time, correlation by the program with data derived from other in-dwelling medical devices may also prove useful in establishing diagnosis. In this example, suppose the bot derived bioassays reveal early signs of myocardial infarction as the underlying cause for the hyperglycemia. If a cardiac pacemaker was also in place, then data related to cardiac rate and rhythm and pacemaker activation may provide the program with additional data to assist in program and/or clinician diagnosis and analysis of the severity of the infarct and cardiac function.

The present invention provides the means with which bots can act both independently and in coordinated groups for the purpose of targeted diagnosis and intervention. When applicable, bot derived data and actions can also be coordinated by the program with a variety of other in-vivo medical devices, leading to the creation of a body area network which facilitates multi-organ and multi-disease diagnosis and intervention.

Functionality

Functionality is an important determinant of bot categorization since it defines the intrinsic working capabilities in both diagnostic and therapeutic actions. In one embodiment, from a diagnostic perspective, the principal function that bots may carry out include (but are not limited to) bioassays, sampling/collection, physical measurements, visualization, and recording of local environmental conditions. The resulting data and/or specimens derived from these actions can be locally stored in bot memory 112 by the program, or transferred to a secondary collection site 115, 125. In the case of data, this would entail local and area storage networks whereas in the case of physical specimens, this would entail local storage reservoirs 108 which may be contained within the primary bots 100 or a secondary device (through physical transfer of the specimen).

In one embodiment, a variety of micro-extraction sampling methods (e.g., needles, probes, aspiration devices 105, etc.) can be integrated into bots 100 providing them with the ability to sample and/or collect cellular and/or subcellular in-vivo biologic specimens. The specific nature of these micro-extraction techniques and functionality can serve as another means of bot categorization.

In one embodiment, since multiple numbers and types of miniaturized biosensors 102, 105, 106 etc., can be integrated into a single bot 100, this leads to the creation of multifunctional bots, which when applied to medicine can possess both multi-diagnostic and multi-therapeutic capabilities. As an example, a single bot 100 released in the bloodstream can be programmed for both diagnostic and therapeutic purposes.

A. Diagnostic and Therapeutic Bots

In one embodiment, on the basis of functionality, these fall into two broad categories, diagnostic and therapeutic. Diagnostic bots function to collect data which can be used for diagnostic analysis, while therapeutic bots interact with the local environment to instill some sort of change, which routinely serves a therapeutic effect. Examples of relevant therapeutic actions include (but are not limited to) local drug delivery, ablation, microsurgery, embolization, radiation emission, and cellular aggregation.

In one embodiment, since bioassays and physical measurements are primary diagnostic functions of bots 100, the underlying technology which facilitates these measurements (e.g., microscopic biosensors 102, 105, etc.) are another important way in which bots can be categorized. As described herein, a large and continuously growing list of biomarkers exists, which can be used to provide early and more accurate diagnosis of disease. Each of these biomarkers (and other physical measurements) require specific sensor technologies, which, in one embodiment, can be used to define bot functionality. Since bots 100 may contain more than one type of embedded biosensor 102, 105 etc., classification should account for the full complement of diagnostic capabilities. Depending upon the clinical circumstance and required action, bots with multi-sensor functionality may be required by the program to actively record data specific to one group of biosensors without active participation of another. Since bots can be used in large numbers (e.g., millions), active recruitment of specific categories by the program may be required for different tasks.

In one embodiment of the present invention, one or more multifunctional bots 100 can perform proactive real-time diagnosis using diagnostic/therapeutic module 126, as it/they move through a biologic medium (e.g., bloodstream) performing routine diagnostics for early disease detection. These bots 100 may contain a variety of microscopic biosensors 102, 105 etc., which are used for bioassays, which are aimed at detecting microscopic quantities of disease markers. For example, in the diagnostic mode of operation, the bot 100 can contain sensors 102, 105, etc., designed to detect a variety of chemicals, enzymes, or genetic tumor markers. At the same time, separate and distinct miniaturized bio-devices 106 etc., in the same bot 100 can be used for a variety of therapeutic purposes (e.g., drug delivery, cell destruction, genetic manipulation).

In one embodiment, in the event that abnormal biomarkers are detected by, for example, biosensor 106, and the data is transmitted externally via transmitter 129 to the computer system 113, which records and saves the data in a database 112, verifies the data using analysis by the program, and quantifies the data in accordance with an active disease state, then anatomic localizers 133 may be deployed by the program at the various sites of abnormal data detection, thereby providing an anatomic reference for further bot migration, analysis, and potential intervention.

In one embodiment, from a therapeutic perspective, bots 100 can be categorized in accordance with the specific type of therapeutic functions they are capable of performing including (but not limited to) drug delivery, ablation, cryotherapy, cauterization, microsurgery, and embolization. While the small size of bots 100 limits the scope of the intervention, their unique ability to perform their actions on a cellular/molecular level provides the capability of therapeutic intervention before disease becomes clinically apparent, at which time macroscopic intervention at the tissue/organ level would be necessary for effective treatment.

In an exemplary embodiment as noted above, a single bot released in the bloodstream can be programmed for both diagnostic and therapeutic purposes. In the diagnostic mode of operation, the bot can contain sensors designed to detect a variety of chemicals, enzymes, or genetic tumor markers. At the same time, separate and distinct miniaturized bio-devices in the same bot can be used for a variety of therapeutic purposes (e.g. drug delivery, cell destruction, genetic manipulation).

In one embodiment, by integrating the miniaturized sensors 102, 105 etc., within the structure of the bot, each individual bot would possess functionality commensurate with both the individual and collective attributes of the embedded sensors. In circumstances in which different types of biosensors 104 etc., are contained within the same bot, the biosensor derived data may be complementary or synergistic to one another and lead the program to perform enhanced diagnosis.

In one exemplary embodiment, different types of biosensors embedded within the same bot can provide complementary diagnostic data, sepsis, which represents a life-threatening infection. In the course of sepsis, two distinct and predictable phases are observed over time (i.e., biphasic model of sepsis), which relate to the physiologic response elicited to the pathogen. In the first phase (i.e., hyper-inflammatory phase), the body responds by activating a number of inflammatory response pathways and with this comes the predictable release of a number of biomarkers. In the second hypo-inflammatory (or immunosuppressive) phase, a different set of biomarkers are recorded. Examples of relevant biomarkers for diagnosis and analysis of sepsis by the program include biomarkers specific to the early hyper-inflammatory phase (e.g., cytokines, chemokines, liposaccharide binding protein) and biomarkers specific to the late hypo-inflammatory phase (macrophage migration inhibiting factor, C-reactive protein, procalcitonin, lactate, and angiopoietin). Quantitative and qualitative temporal measurements of these biomarkers may be used for a variety of clinical analyses by the program, including screening high risk patients, establishing early diagnosis (when treatment will be more effective), patient risk stratification, prediction of clinical outcomes, and monitoring of intervention response.

It is important to note that measurements of single biomarkers are often inconclusive. A preferable strategy is for the program to collect and analyze data from multiple different types of biomarkers (i.e., combination biomarker analysis), which has been shown in scientific studies to improve the sensitivity and specificity of clinical diagnosis and outcomes analysis.

In one embodiment, the program of the present invention can facilitate this strategy of combination biomarker analysis by combining synergistic data from different types of biosensors embedded within individual and/or neighboring bots. In addition, the resulting combination biomarker (i.e., microscopic) data can be correlated using the program with other types of "macroscopic" clinical data (e.g., body temperature, heart rate, respiratory rate, white blood cell (WBC) count to create a quantitative multi-data scoring system for improved diagnostic and therapeutic analysis. Since the degree and duration of immune response will often differ among patients, the combination biomarker analysis can be customized by the program to unique patient and clinical attributes (e.g., age, physical state, comorbidities, pathogen virulence, pathogen burden, and genetic factors) to create a personalized biomedical patient profile.

By creating the ability to embed a variety and number of biomarkers within mobile bots, the program of the present invention can effectively create continuous data—driven temporal analysis specific to the individual patient, clinical context (i.e., disease state), anatomic location, and intervention.

While the aforementioned illustrative example was specific to sepsis (i.e., systemic infection), other applications of the present invention may include a wide array of other pathologic conditions including (but not limited to) exposure to toxins (e.g., alcohol, drugs, chemical agents, radiation), malignancy (i.e., cancer), trauma, autoimmune disease, iatrogenic insult, vasculitis, and genetic disease.

In one embodiment, another functional component of microbots/nanobots 100 of the present invention, is the ability to adhere or attach to the surface of the biologic substrate in which it is performing its intended diagnostic and/or therapeutic function. This adherence capability allows the microbots/nanobots 100 to remain stationary and fixed in position, creating the ability to perform longitudinal data collection and/or therapeutic action. This ability to adhere to an anatomic surface can be achieved by physical (e.g., micro-prongs) or chemical (e.g., biologic adhesive) means. This also serves as a functional component of microbot/nanobot 100 categorization.

In one exemplary embodiment of diagnostic/therapeutic function, if the preliminary data collected by the bots 100, which are analyzed by the program, reveal the source of the bioassay elevation to reside in a particular region, such as the sinuses, a more focused analysis can be performed by the location module 120 to more accurately localize the exact site of infection. As this targeted sinus data is collected and analyzed by the program, it is learned that the specific location of infection is the left sphenoid sinus. Bots 100 with the capability of cellular collection can then be directed by the program to transport local mucosal cells from the infected left sphenoid sinus to a collection medical device (i.e., intravascular catheter), which when removed can provide clinicians with cells for microbiologic analysis.

In one embodiment, cultures of the specimen analyzed by the program, can both identify the offending bacterial or fungal pathogen, while also providing the ability to determine which antibiotics are most effective for treatment. This ability to prospectively analyze cellular biology, physiology, pathology, and anatomic location in real-time and direct therapeutic response is a unique attribute of the present invention which transforms traditional macroscopic assessment and intervention to one of a microscopic nature.

In one embodiment, in addition to the quantitative and qualitative assessment of trauma related biomarkers, bots can also provide a bevy of physical data related to trauma. In addition to anatomic localization of the trauma site(s), biosensor and image derived data can provide important insights related to the size and severity of tissue/organ injury, presence of leakage or extravasation of fluid (e.g., urine, bile, cerebrospinal fluid), velocity and directionality of abnormal flow (e.g., active bleeding), size/volume and rate of expansion of abnormal fluid collections.

In one embodiment, in addition to diagnosis, bots are used for therapeutic purposes such as thermal ablation, injection of bio-adhesives and anticoagulants, localized drug release, and microsurgery, where the specially designed bots can be directed to the specific site of injury and deployed for therapeutic purposes. Continuous monitoring of trauma related data by the program provides insight as to the relative impact of these interventions on tissue/organ injury.

In one embodiment, bots provide a number of potential therapeutic options which can be facilitated in the field including local drug delivery (e.g., antibiotics for prophylaxis of infection, opioids for analgesia, and local administration of thrombin for control of bleeding). In addition to localized drug delivery, specialized bots can provide a number of other therapeutic interventions at the specific site of vascular injury including (but not limited to) microsurgery, embolization, and tamponade. The key element is that diagnostic bots provide a mechanism for injury diagnosis, detailed anatomic localization, and grading of severity.

Therapeutic bots in turn provide for a number of potential interventions which can be customized in accordance with the specific type, location, and severity of injury.

In one embodiment, once the therapeutic intervention has been initiated, diagnostic bots can in turn monitor treatment response and requirement for modification. While most soldiers in the field may have limited accessibility to specialized bots, the medic may be equipped with a variety of specialized bots for these more intensive operations. Once provided with the salient patient-specific data, the medic could administer a bolus of these specialized bots via an injection in the field. Once injected, these bots can be directed to the specific site of injury in accordance with the previously described methods of communication.

In one embodiment, each individual bot would have its own specific operational radiofrequency which provides the ability to locate, direct, and communicate with individual bots. In addition to this "individual specific" radiofrequency identification signal, commonly shared identification signals can be used for a given functional class or category of bots, which enables communication on a group basis (discussed further below).

In an exemplary embodiment, suppose an authorized end-user wants to direct a number of 'retrieval' bots to the liver for collection of cellular/tissue specimens which are being collected by "biopsy/aspiration" bots. By utilizing the shared communication frequency for those bots with the appropriate functionality and structure, a directive can be transmitted by the program which alerts those bots to the anatomic location of interest and the identity of those bots in which they will engage for transfer of the cellular/tissue specimens being collected. Once the transfer has been successfully completed, a second "shared" signal can be transmitted by the program requesting those retrieval bots to "return home" (which instructs them to return to a designated anatomic site for removal from the body). In some applications, an authorized end-user may not want an entire class of bots to perform a given function, but only a subset of the total number. In this circumstance, the "shared" communication signal can be selectively sent to a specific number of qualified bots based on the number required to complete the task at hand.

In an alternative embodiment, the shared signal is transmitted by the program from a given location (e.g., liver), with a predetermined transmission range, so that only qualified bots within a predefined signal range will successfully receive the transmitted signal. This provides a method of communication and rapid response in accordance with bot location. Since an infinitely large number of radiofrequency signals can be used for communication, one can design a large number of subsets of bots for each individual frequency in accordance with a given action. As an example, since the number of circulating bots at any single point of time may number in the millions, functional groups of a specific number (e.g., 10,000) can be created, to provide flexibility in the number of bots assigned to a single task.

Since bots are often multifunctional in nature and may possess a variety of different embedded nanotechnologies (e.g., micro-sensors), each individual property, functionality, or contained technology can be used to define an associated communication signal. As a result, an individual bot may have ten different associated signal frequencies it can respond to, in accordance with the individual property which is being sought. As an example, a bot containing three different types of embedded micro-sensors and possessing the combined functions of tissue/cell collection, bioassay, and chemical storage may have seven different radiofrequency communication signals (its individual unique identifier, one for each type of sensor (3), and one for each functional capability (3). At any point in time, the individual signal used for communication would be specific to the individual bot and the application of interest.

Note that the method used for individual bot identification and communication is not necessarily restricted to radiofrequency waves but can utilize other technologies and signal forms including (but not limited to) light, sound, temperature, ultrasound, lasers, and magnetism.

In one embodiment, the unique identifiers and corresponding signals for each individual bot can be stored in a central database 115, 125 for the purpose of bot-specific longitudinal data collection and analysis by the program. In addition to the clinical applications being performed for the individual host (e.g., patient, animal), this data can also be used by the program for quality control (i.e., technical performance of the individual bots), comparative technology assessment (i.e., functional performance of different bots providers), operator assessment (i.e., performance relative to the authorized end-user directing bots action), anatomic assessment (i.e., performance of bots within different anatomic structures and/or organ systems), and disease assessment (performance of bots for a given disease state or in combination of multiple disease states). The intended purpose of this longitudinal data assessment by the program is to provide continuous analysis of microbot/nanobot performance on an individual and group basis and comingle this data with large numbers of end-users for the purpose of creating large sample size statistical analysis which can be used to create "best practice" guidelines and evidence based medicine standards which can be customized to the genotype and phenotype of the individual patient, disease, anatomy, and clinical application (i.e., personalized medicine).

B. Visualization

In one embodiment, an important feature of microbot/nanobot 100 functionality is visualization capabilities. Visualization technology can take a number of different forms including (but not limited to) photography, video, endoscopy, confocal imaging, two photon imaging, intravital imaging, laser excitation, optical frequency domain imaging, optical coherence tomography, infrared imaging, and ultrasound. In one embodiment, the visualization technologies of the present invention can be used at the microscopic level and can become integrated and/or embedded within microbots/nanobots 100, thereby providing in-vivo visualization which can be used for pathology assessment, anatomic mapping, and anatomic localization.

In one embodiment, the ability for microbots/nanobots 100 to localize at a specific anatomic site can be accomplished through both indirect means (e.g., external anatomic markers, radiofrequency navigation), and direct means, with embedded visualization technologies providing the ability for microbots/nanobots to become self-directed to a specific anatomic location of clinical interest. The ability of microbots/nanobots to possess visualization capabilities is another variable which can be included in the categorization schema.

In one embodiment, additional features of the present invention include (but are not limited to) video (i.e., camera 101), ultrasound, light, electromagnetic waves, and infrared imaging. Individual imaging techniques can also be combined to form synergistic hybrid imaging (e.g., multispectral optoacoustic tomography). The primary purpose of these embedded visualization tools is to provide a direct method for in-vivo visualization at a microscopic level which can be combined with the aforementioned anatomic localization methods for anatomic mapping at the cellular and/or molecular levels. These microscopic anatomic maps can in turn be correlated with the "macroscopic" imaging data (e.g., conventional MRI, ultrasound, intraoperative or intra-procedural photography) by a visualization module 122 of the computer system, to create combination visualization data from external and internal sources, at both tissue/organ and cellular levels.

In one embodiment, while the microscopic imaging data obtained from a single bot would be of limited utility in anatomic mapping and pathology visualization, the ability of the visualization module 122 to combine anatomic and visualization from large quantities of bots 100 creates the ability to pool large quantities of visualization data from a single (as well as contiguous) anatomic sites to create enhanced visualization, which can be combined using the program, with various types of biologic and pathologic data (e.g., chemical bioassays, DNA analysis, biopsies) to yield a comprehensive anatomic, visualization, and functional in-vivo four dimensional (4D) map (time is the $4^{th}$ dimension) which can be continuously monitored by the program over time to detect local environmental changes at both cellular and tissue levels.

In one embodiment, the resulting program-derived in-vivo anatomic mapping and visualization data (for both normal anatomy and pathology), in combination with external data from macroscopic imaging/visualization technologies provides a unique method for creating detailed 4D visualization maps using the visualization module, which have a variety of clinical applications.

It is noted that while the anatomic data is relatively fixed, since pathology contained within the body can change over time, this does create some degree of temporal change at both cellular and tissue levels. Examples such as infection, inflammation, trauma, and neoplasm may all distort local anatomic architecture which can be accounted for in one embodiment, by the visualization module 122 of the present invention, through the longitudinal data collection provided by bots 100.

In the exemplary embodiment of a solid organ (e.g., liver), the real-time collection of this anatomic/visualization data by the program is largely limited to internal "conduits" such as capillaries, venules, sinusoids, veins, arteries, and arteries which traverse the internal architecture of liver parenchyma. At the same time, pathologic states with internal air or fluid (e.g., liquefied hematoma, necrotic tumor) provide an alternative means in which migrating bots 100 can enter the region of pathology, map out its anatomy, and create internal 4D visualization maps which can be combined by the program with external visualization data using the visualization module 122. Using computerized advanced visualization technologies, this combined internal and external anatomic and visualization data can have the visualization module 122 of the present invention produce intricately detailed anatomic maps which can provide the ability to track disease progression/regression, plan and direct interventional strategies (e.g., image-guided microsurgery), identify anatomic variations (which may not be visible through conventional external imaging technologies), and directly correlate biologic functionality with anatomic structure—providing this information to the clinician for his review.

This latter embodiment of the present invention is important for it allows for the program's correlation of biologic and physiologic data at microscopic, cellular, and tissue levels, so that the program can directly correlate this data with the anatomy. In an exemplary embodiment, in the case of a malignant liver tumor (e.g., hepatocellular carcinoma, metastasis), bot derived bioassays can be used by the program to analyze tumor metabolic activity, DNA mutations, or apoptosis while the anatomic derived data can provide correlating data related to sites of necrosis, neovascularity (i.e., malignant angiogenesis), or neoplastic cellular proliferation. This unique ability of the program of the present invention to collect, analyze, and visualize simultaneous biologic, genomic, and anatomic data along with real-time change provides a powerful method of early diagnosis, treatment, and assessment of response to various types of interventions.

C. Bot Elimination and Retrieval

In one embodiment, there are a number of different ways in which microbots/nanobots 100 can be eliminated from the host. The simplest mode of elimination is through normal biologic channels, such as the urinary and gastrointestinal tracts. When bots are eliminated via physiologic pathways, their subsequent retrieval for additional processing and/or salvage can be facilitated by filtration of the medium 128 in which they are eliminated. This may entail filtering urinary or stool output for sequestering the excreted bots. In certain circumstances, ancillary markers and/or emission signals (e.g. sound, electromagnetic signals, light) can be used to enhance this filtration process. This mode of elimination is preferred when the microbots/nanobots contain data or material which needs to be retrieved for additional analysis.

In addition to physiologic excretion, in one embodiment, bots (or bot containing macrophages) may also be salvaged through the bloodstream through the filtration of blood (i.e. in a manner similar to hemodialysis) or targeted blood collection. In the case of targeted blood collection, the circulating bots can be mobilized at a specific anatomic location (e.g., right antecubital vein) through external signal transmission and then externally withdrawn through targeted venipuncture. Before the venipuncture is performed, the sequestration of the targeted bots in the desired location can be confirmed through transmission and receipt of bot generated signals (e.g. light, radiofrequency, electromagnetic, sound), which can be externally verified and localized by the program using an externally located receiving device 133 at the anatomic location of interest. In addition to verifying bot location, these external receiving devices 133 can also be used to transmit signals and direct the circulating bots of interest to the desired anatomic location (in a manner analogous to a magnet physically attracting ferrous material).

In another embodiment in which microbots/nanobots 100 can be eliminated is through biodegradability and/or metabolism (i.e. end of lifetime) —i.e., intrinsic metabolic pathways (e.g., liver) —in which the microbots/nanobots undergo breakdown and are therefore not retrievable. In situations where the function of the microbots/nanobots have been successfully completed (e.g., bioassay), this method of elimination is a viable option.

In yet another embodiment of the present invention, elimination is through phagocytosis, in which the microbots/nanobots 100 are actively engulfed in-vivo by circulating host phagocytes, which may or may not be retrieved in the future through filtration of blood. This latter form of elimination can be stimulated through emission of an external signal triggering multiple nanobots to aggregate with one another and subsequently eliciting a chemical and/or electrical signal to stimulate macrophage ingestion (i.e. triggered phagocytosis). This method of elimination may be preferred when intracellular data collection is a requirement of microbots/nanobots 100 function. Phagocytosis is a major mechanism within a host immune system for removal of pathogens, foreign bodies, and cell debris. Once the pathogen becomes trapped in the phagocyte it then undergoes fusion with a lysosome to form a phagolysosome, in which enzymes and peroxides are released and act to destroy the pathogen. The ability of microbots/nanobots to undergo phagocytosis can serve as an important method for intracellular diagnosis, followed by elimination.

In an exemplary embodiment of non-retrieval such as phagocytosis, the internal bot contents (i.e., material in storage 108), are deemed "non-essential" by the program or clinician, and therefore, left to in-vivo lysosome destruction by the host phagocyte (i.e., compartment 108 is left open to phagocyte, or expelled to be enveloped by the phagocyte). In the example in which the bot contents are deemed by the program (or clinician) to be important for additional analysis, the bot must be evacuated prior to the destructive phagocytic process and this can be accomplished by a third-party transfer.

In the third-party transfer embodiment, the "donor bot" may be directed to a specific anatomic location through a targeted signal transmission, which contains the anatomic coordinates, date and time for the desired action to occur, and unique transmission coordinates for communication, identification, and verification between the "donor" and receiver" bots. The structure and function of the "receiver bot" can be highly variable, in accordance with its functionality and storage requirements. In the event that the 'receiver bot" must have large storage capacity, the receiving device may be macroscopic in nature (e.g., vascular catheter, subcutaneous implant). Once the receiver bot/device has successfully completed its task it can then be externally retrieved for content and data processing.

In one embodiment, a retrieval device (e.g., catheter, tube, stent) can be used for bot retrieval, and can send out a specific "retrieval" signal to bots which have completed their designated task or function. The bots can in turn be directed (via either active or passive movement) to the internal device, which collects and quantifies the number of retrieved bots. Since each individual bot has its own unique emitted signal frequency, both the number and individual classification of bots can be recorded by the program. The associated data can then be transmitted to an authorized end-user who can determine the appropriate time for device removal.

In one embodiment, another retrieval option is through insertion of an in-vivo device which has the capabilities of emitting electromagnetic waves which can serve to physically direct and attract the circulating bots to its location. In addition, once can preferentially retrieve specific bots through selective signal transmission, thereby allowing for only those "desired" bots to be selectively retrieved while allowing all other bots to continue to operate.

In one embodiment, the strategy for bot elimination can in part be driven based upon the functionality, structure, internal contents, and/or intrinsic value of the individual bot in question. If for example, a bot is simply performing the function of data collection/analysis and the associated data has been verified, transmitted, and received by the program and stored in an external data storage device 125, its remaining intrinsic value following task completion may not require active salvage. On the other hand, a bot 100 tasked with collection of biologic material (e.g. DNA, cells, tissue, fluid) would require successful transfer of the collected specimen prior to its disposal. If this disposal could be satisfactorily performed in-vivo (e.g., to an external collection device), then the long-term retention of the bot may not be necessary. If, on the other hand, the bot requires retrieval outside of the host for retrieval of the collected specimen, then its active "intact" retrieval is important. In this embodiment, the bot may be designed to be eliminated from the host via a physiologic pathway (e.g. gastrointestinal, genitourinary tracts) in order to preserve its structure and maintain integrity of the stored contents for future analysis.

D. Aggregation

In one embodiment, the present invention includes selective aggregation of bots 100 for biologic elimination. As stated above, in some embodiments (e.g., specimen collection), bots may contain valuable biologic material which when retrieved outside of the host can provide valuable medical information used for enhanced diagnosis and/or treatment.

In one embodiment of the present invention, bot retrieval can be enhanced by aggregation of multiple bots 300 into a conglomerate entity 302 (see FIGS. 3A-3C), which can then be excreted through conventional biologic pathways (e.g., gastrointestinal (GI) or genitourinary (GU) tracts) or via macrophage consumption (which can subsequently be retrieved through plasmapheresis). FIGS. 3A-3C depict both the coalescence of multiple bots 300 at a target site 301, into a macrobot 302 which is subsequently excreted through the GI/GU tracts or consumed by a macrophage (which is turn retrieved).

In one embodiment of the present invention, the process of bot 300 aggregation may be facilitated through selective inter-bot communication and/or attraction, in which selected bots 300 may respond to an external signal (e.g., electrical charge, radiofrequency wave, audio signal) which causes them to coalesce with one another into a conglomerate bot 302. Once the conglomerate bot 302 is excreted or phagocytized, it can subsequently be retrieved and microscopically dissected, in order to retrieve individual bot 300 contents for further medical analysis. Note that bot 300 aggregation may also play an important role when functionality can be enhanced through large numbers of bots 300 acting in a single collective fashion (e.g., drug delivery).

In one embodiment, a feature of the present invention is the ability to coordinate the coalescence of multiple bots 300 at a single anatomic location for the purpose of synergistic diagnostic and/or therapeutic functionality. Once circulating bots have arrived at the specific anatomic location of interest, a specific secure signal can be transmitted via wireless technology to activate the physical coalescence of a specific category of bots for the purpose of creating a macro-aggregated bot (MAB), including thousands (or even millions) of individual bots 300 which can simultaneously perform the same diagnostic and/or therapeutic function. By acting in concert to one another this creates markedly expanded functionality, which would not be readily available by individual bots acting independent to one another. The wireless transmission of signals by an authorized end-user over a secure network can result in a number of actions including (but not limited to) the following:

1. Specific anatomic location/s of interest.
2. Breadth and depth requirements for volumetric coverage (by the coalesced bots).
3. Functional requirements (i.e. specific diagnostic and/or therapeutic actions to be taken).
4. Time duration (i.e. defined endpoint) for requisite action.
5. Method of bots disassembly, retrieval, and/or elimination.
6. Physical assembly requirements (e.g. shape, size, geometry) of macro-aggregated bot (MAB).
7. Identification of specific bots for inclusion in the MAB In one embodiment, both in-vivo and external data sources can be used to assist in identifying the anatomic location of interest. External data sources may include medical imaging tests (e.g., MRI, nuclear medicine, CT), peripheral blood assays (e.g., chemical analysis, tumor markers, genomics), intraoperative/percutaneous procedures, and photography. In-vivo data sources may include smart medical devices (e.g., vascular catheters, insulin pump, implanted defibrillator), endoscopy, or circulating bots. The granularity and accuracy of the data being analyzed by the program will determine the specificity of the anatomic location, which will often require validation and refinement through in-vivo bot analysis by the program. Once the anatomic location has been validated and narrowly defined, the subsequent action of MAB creation can be performed.

In order to accomplish this task, in one embodiment, an authorized end-user must input a number of data requirements which define the desired actions, functional requirements, and physical attributes of the MAB. In one embodiment, once this input data has been completed, a second authorized end-user would be required for verification and activation (in order to improve system security and clinical outcomes). In one embodiment, a wireless transmission would then be generated which contains the specific signal signatures for the bots which fulfill the functional and physical requirements for the desired MAB. These individual bots can then be directed to the specific anatomic location of interest by a localizing signal (i.e. beacon) which is emitted by an in-vivo anatomic marker (e.g. surgical clip, suture), which has been placed by a tasked bot. In some instances, multiple anatomic markers may be deposited by localizing bots to define the desired 3-dimensional (3D) boundaries of the MAB, corresponding to the entire area of underlying pathology. Based upon these 3D boundaries, a 3D graphic display can be created by the program which provides both the authorized end-user with a visual representation on the display 123, of the desired MAB within the anatomic structures of interest.

In many respects this would be analogous to conventional computer-assisted design (CAD) programs currently used in a variety of applications including architecture, engineering, and aerospace design. In the present invention, the derived 3D display 123 would provide a visual representation of the MAB based upon the input data. The authorized end-users could in turn make design modifications (if needed) by modifying the data input requirements, with the final display being reviewed by the artificial intelligence techniques of the program to ensure biologic functionality and safety requirements are maintained.

In one exemplary embodiment, to illustrate how this MAB data input and 3D design would be performed, a suspected tumor in the liver is located adjacent to the origin of the bifurcation of the right and central hepatic veins. The diagnosis was originally made using externally derived data from an MRI, which was subsequently confirmed by bots derived in-vivo bioassays. Following collection of biomarkers at a number of anatomic locations and the program correlating with the external MRI data (which delineates the size, morphology, and anatomic location of the suspected tumor), anatomic localizers were deposited by the deployment bots (in the venous walls) outlining the entire 3-dimensional area for MAB creation at the origin of the right and middle hepatic vein bifurcation. Following human and/or artificial intelligence data input, a 3D visual display was created by the program which represents the optimum MAB design, in accordance with the local anatomy, functional requirements, and safety considerations. In this example, the MAB would be Y-shaped based on the anatomy, tumor volume, and bot functionality. At the same time, in order to preserve normal venous flow (and avoid venous occlusion), the MAB would be porous in design, so as to allow continuous venous flow in the involved hepatic veins.

In one exemplary embodiment, using in-vivo physiologic data obtained from local bots, the venous flow rate measurements are tested by the program on the computer-derived MAB porous design structure, which estimates that the current design will restrict venous flow by 30%. In order to return the estimated venous flow rate to its baseline (i.e., physiologic value), larger internal gaps in MAB design are required. Once the revised data input is used by the program in redesigning the MAB structure, a new visual display is presented by the program for review by the user on the display 123, which incorporates the prior data input along with the revised flow estimates. If found to be acceptable (by human and/or artificial intelligence analysis), the MAB design is verified by the program and MAB creation is activated (through appropriate signal transmission).

The corresponding signals being transmitted correspond to the following for MAB assembly:
1. Identification of the number of required bots.
2. Specification of bots functionality and classification.
3. Chronology (i.e. timing) of bots aggregation.
4. Physical location of individual bots (relative to the embedded anatomic localizers and overall MAB structure).
5. Identification of "structural" bots used for anatomic stabilization of the MAB.

In one embodiment, as these transmitted signals are received by circulating bots and acted upon, a MAB begins to form, which conforms to the design specifications of the computer assisted design. Before the MAB can begin to form through progressive aggregation of preselected bots, anchoring bots (which are a specific type of bots) are initially directed to the anatomic site(s) of interest and deployed along the biologic substrate so as to produce a stationary and fixed position of the MAB. The number of deployed anchoring bots are dependent upon the size of the anatomic area of coverage, the specific substrate in which they will adhere to, and the overall size of planned MAB.

A variety of techniques can be used for adherence of the anchoring bots to the biologic substrate including (but not limited to) secretion of a bioadhesive from the surface of the bots which acts as a sealant, extrusion of numerous physical micro-structures (e.g. prong, screw, strut) producing a physical connection, or emission of an electrostatic charge which produces a magnetic attraction between the opposing surfaces. By deployment of numerous anchoring bots along the entire surface area of the anatomic region of interest, a broad foundation is established from which other functional bots can begin to aggregate and form the MAB, which is localized to the specific anatomic region(s) of interest.

In one embodiment, in addition to adherence to the biologic substrate of anatomic interest (e.g., hepatic vein wall), the coalescing bots must also have a mechanism for attaching to one another in order to form the conglomerate MAB. This can be accomplished by incorporating a micro-reservoir (capable of releasing a sealant) or surface bioadhesive compound in the walls of the bots, which can be selectively activated to provide a locking mechanism between neighboring bots. By spacing these attachment mechanisms at various locations on the bot's surface, one creates the ability to attach multiple bots to a single bot and at a variety of different surface locations. The specific locations on a given bot's surface which are most desired for binding (based on bot position within the MAB), are then activated to provide an adherence guide for the neighboring bots. In the event that an incorrect location is used for adherence, the bots can be deactivated, thereby removing the physical connection between the adjacent bots. This ability to intelligently "build" a MAB by targeted coalescence of numerous bots provides a mechanism in which the MAB can be constructed in accordance with the computer-derived 3D design by the program.

In one exemplary embodiment, in a hepatic tumor requiring diagnostic tumor analysis, the bots which possess the ability to perform the specific bioassays of interest will be targeted for aggregation. When the corresponding signal is transmitted by the program (externally from an authenticated end-user and/or internally from a messenger bot), the circulating bots which meet the criteria of interest are then activated by the signal and are in turn directed to the anatomic region of interest. In this example, MAB formation is desired at the bifurcation of the right and middle hepatic veins, so the messenger bots will first position themselves at this location before emitting the appropriate aggregation signal. Those bots which possess the desired diagnostic capabilities will then follow the emitted signal to the bots' anatomic location of interest. In this example, the same bots used for anchoring may also possess messenger capabilities (i.e., are multifunctional). As a result, once anchored at the desired anatomic location (e.g., hepatic vein bifurcation), their messenger functionality can be invoked (e.g., through external activation by an authorized end-user). The net result is as circulating bots possessing the appropriate functionality receive the appropriate signal, they are guided to the location of interest and begin coalescing with one another, to eventually form the desired MAB. Once the MAB has been completed in accordance with design specifications, the messenger signal is terminated, thereby completing MAB construction.

In one exemplary embodiment, a Y-shaped diagnostic MAB is formed at the junction of the right and middle hepatic veins, comprised of thousands (or millions) of bots. The power of aggregation creates a complex of similarly functioned bots to perform bioassays at an exponential level when compared with bioassays of individual bots. As a result, the diagnostic sensitivity/specificity of the bioassay of interest is far more accurate and can provide expedited diagnosis and treatment planning. In this example, the diagnosis of hepatocellular carcinoma is realized, which in turn prompts therapeutic intervention. Rather than starting from scratch the same anatomic specific MAB infrastructure can be used to convert the MAB from one of diagnostic to therapeutic functionality. Since this will likely require replacing the diagnostic bots with therapeutic bots, a transformation is directed by the program which entails releasing the diagnostic bots from the core of the MAB and replacing them with the desired therapeutic bots, while continuing to utilize the existing MAB infrastructure and design. This ability to transition or "rebuild" MABs is another unique attribute of the present invention and provides added versatility and functionality.

In this example, the anchoring bots which provide structural support and adherence of the MAB to the biologic substrate of interest would be maintained, while the 'functional" bots which provide specific diagnostic and/or therapeutic actions would be disassociated from the MAB and return to the medium (e.g., blood) from which they were originally introduced. Residual messenger bots would then provide signal transmission to the specifically desired bots (e.g., therapeutic bots) which could then be directed to the anatomic location of interest and then incorporate themselves into the MAB complex. As new bots begin to assume their position within the existing MAB complex, signals are initiated by the program and transmitted from both the existing and newly migrated bots to monitor MAB growth. Once the full capacity has been reached, then signals from the messenger bots cease, so that additional therapeutic bots are no longer recruited. The functional and physical status of the newly converted MAB can also be externally monitored by the program via wireless signal transmission and analysis, along with feedback and data obtained from circulating bots equipped with visual apparatus (e.g., photography, video, ultrasound, light, electromagnetic pulse). Once the MAB conversion has been completed, authorized end-users or the program can then direct the bots within the MAB to begin functioning. In this example, this action may consist of release of anti-tumor pharmaceuticals aimed at local destruction of malignant cells.

In one embodiment, an additional advantage of the MAB is the ability to utilize other in-vivo tools and techniques for expanded diagnosis and/or treatment which might not be available to individual bots. In an exemplary embodiment, of a local drug delivery to a hepatic malignancy, the locally stored pharmacologic agents may be resupplied or replaced by circulating storage devices which have the ability to attach to the MAB complex through externally located anchoring bots. Once engaged, a signal can be emitted (either externally via an authorized end-user or internally from bots contained within the MAB) which authorizes release of the storage device reservoir to the MAB contained bots. Once released, the reservoir empties its contents directly into the MAB complex (e.g., into the open porous space), from which the drug can be either passively absorbed by local cells/tissue or actively released by needles/injection devices contained within bots which have retrieved the pharmaceutical into their own individual reservoirs 108 through physical suction and/or diffusion.

In one embodiment, the replacement of the MAB complex need not only be restricted between diagnostic and therapeutic functions but can also include replacing one diagnostic function with another diagnostic function. The ability to form MABs can also prove useful in other applications including (but not limited to) filtration (e.g., filtering out toxins, viruses, bacteria from biologic media), elimination (e.g., macro-aggregation with subsequent physiologic removal by circulating macrophages), collection of stored cells and/or DNA material (e.g., macro-aggregation with subsequent excretion via urinary system from which it can be collected), and mobile therapeutic action (e.g., circulating MABs in infected media (e.g., bacterial blood infection) in which circulating MABs release drugs over a prolonged anatomic region/territory.

Note the ability to form MABs is particularly advantageous when biologic specimens are being collected, since it may be difficult to reliably identify and retrieve individual bots do to size constraints. A MAB containing thousands or millions of individual bots on the other hand can provide physical protection of individual bots while also providing an important size for identification and retrieval. If for example the MAB is excreted via the urinary system, the urine can be collected and filtered, in order to capture and retrieve the excreted MABs.

D. Artificial Intelligence

In one embodiment of the present invention, artificial intelligence (AI) may be integrated into microbots/nanobots which provides the program with the ability to adapt and/or react to real-time data and/or environmental stimuli and adjust the system of the present invention's actions via timing module 121.

If, for example, a microbot/nanobot 100 whose primary function is to quantify active bleeding encounters unexpectedly high flow rates at a site of active bleeding it may possess the capability of recruiting other microbots/nanobots for therapeutic action (e.g., cauterization), release self-contained medication payload (e.g., thrombin 109), or initiate a self-destruction protocol which serves as a method of embolization/tamponade. If the microbot/nanobot did not possess intrinsic AI capability, the program would simply transmit the data from the bot to an external source (e.g., computer system 113 of an authorized provider), in which it would be analyzed by the program and then acted upon. Since this data transmission and analysis process would take valuable time, the ability of the program to integrate targeted and context-specific AI into microbots/nanobots would have great advantages and would be another component of functionality used in categorization.

E. Modification of Bot Functionality in Use

In one embodiment, while bot functionality may in part be predetermined at the time of construction (e.g., through embedding specialized microprocessors, biosensors, components for bio-sampling or storage), the present invention includes the additional feature of modifying bot functionality while in active use. This illustrates the ability of bots and authorized healthcare professionals to adapt in real-time to the changing biologic/pathologic conditions which may be encountered in everyday use.

As an example, a bot primarily designated as "diagnostic" in nature through embedded biosensors performing various types of bioassays may encounter an unexpectedly high level of a given type of pathology (e.g., white blood cell localization with high levels of excreted cytokines). Once this data has been validated by the program through continuous longitudinal bioassays confirmed by neighboring bots, an immediate action may be required to respond to the unexpected pathologic condition. On a more superficial level, one real-time adaptation may include changing the type of active biosensors in use so that the bioassays performed more accurately reflect the changing conditions. Since bots may contain multiple types of different sensors, the specific type of biosensors in active mode may vary from time to time.

In one embodiment, in a more in-depth mode, the physical structure of the bot may undergo modification to accommodate to real-time events. In the aforementioned example of localized white blood cell accumulation and cytokine release, the prevailing data would suggest an early stage of developing infection. In response, some of these localized white blood cells and surrounding cellular material/debris may be sequestered by the bots for microbiologic analysis. In the absence of dedicated bots for specimen collection, the most expedient course of action would be to have the diagnostic bots present at the anatomic site of interest undergo conversion to collection bots. This may be accomplished by the bot being modified from its original purpose to utilize a centrally located storage receptacle 108 and deploying an aspiration microneedle for specimen collection. Once the modified bot has satisfactorily collected the specimen of interest, it can be directed by the program to undergo physiologic excretion, so that it can be subsequently retrieved and undergo analysis.

In one embodiment, the real-time modification of bot function can be directed externally by an authorized healthcare professional or internally by a "smart" bot through incorporation of artificial intelligence (AI) in internal electronics. In either case the directed information is transmitted via wireless technology to the receiver/transmitter 129 using the specific individual or group bot frequency, thereby identifying the specific bot(s) of interest. In order to avoid external tampering a security feature of the program may require verification of both the individual entities directing the modification as well as the bots receiving the directive.

In another exemplary embodiment of changing bot functionality, is the situation where bot function has been compromised (e.g., structural defect, faulty biosensor). In this setting, a directive may be issued by the program which calls for the bot to undergo destruction or elimination, in order to prevent physical injury or use of erroneous data. Upon receipt and validation of the "self-destruct" instruction, the bot would then follow the prescribed course of elimination (e.g., phagocytosis, physiologic elimination).

A more detailed analysis and illustrative examples will be subsequently provided explaining many of these microbot/nanobot functions. The important point to be made is that these various functions can be used to classify and categorize the diverse numbers and types of microbots/nanobots which are included in the present invention.

Continuous Real-Time In-Vivo Data Collection and Analysis

In one embodiment, a number of standardized time stamped data can be continuously collected and stored by the program in the database 115 from the bot embedded sensors which provide real-time objective data measurements of in-vivo physiology, anatomy, and pathology. These longitudinal data can in turn be used by the software program to create temporal analyses which can be specific to an individual or type of bot, biosensor, anatomic location, disease state, or bioassay. Individual data thresholds (or critical values) can be established by the program which define when a given data measurement requires additional analysis, notification, and/or intervention. These "data thresholds" can be static or dynamic in nature, in accordance with temporal data trends.

As an example, if an active infection is being monitored by the program through serial measurements of cytokines and chemokines, a physician may request that a critical change in value which exceeds a predefined threshold or an increase of >25% of baseline values warrant immediate notification and acknowledgment of data receipt. If subsequent measurements analyzed by the program verify the initially elevated data measurements and continue to show progressive elevation in these cytokine measures, an elevated alert notification schema is mandated by the program which requires both acknowledgment of the abnormal data readings and a physician-determined intervention.

In one embodiment, in addition to physician notification, these data thresholds may also automatically trigger the program to implement automated decision support to support clinical diagnosis and treatment. Examples of automated decision support may include (but not be limited to) data mining of the patient's medical record to detect other instances of comparable data trends were observed and the response to various interventions, computerized data mining of "comparable" patients whose clinical profile were similar to the patient of record and/or exhibited similar data trends relative to the individual bioassay of concern, review of pharmacological information systems to identify alternative treatment regimens to specifically address the data abnormality of record, or identification of a clinical consultant with proven experience and/or expertise of clinical relevance.

In one embodiment, since in-vivo bots provide the capability of obtaining real time and immediate data in response to any intervention, the program of the present invention provides the capability of objectively defining clinical response to any given intervention, both at local anatomic and systemic levels. Based upon the location, type, method, and timing of intervention, the program can effectively determine the clinical impact of effectiveness over time, which would not be as readily available in the setting of systemic therapy. At the same time, these bot derived bioassay measurements can be correlated by the program with a number of other objective data measurements and test procedures to determine the relationships and interaction effects between disparate different data elements.

The present invention provides a method in which circulating bots would continuously update changes in anatomy (at both macroscopic and microscopic levels), internal flow (e.g., arterial, venous, biliary, lymphatic), hepatic functionality, and physiology. As this continuous data is recorded and analyzed by the program, any subtle change from the post-operative baseline would be promptly detected by the program and warrant closer scrutiny by the program in accordance with the anatomic location, type, and severity of the abnormal data recorded. In the example of the biliary duct leakage, the specific anatomic location, severity, and flow characteristics could be quantified by the program over time, in order to provide a dynamic assessment of the leak along with treatment options.

In one embodiment, in the event that the leakage site was extremely small and self-contained, an in-vivo bot-derived intervention may be chosen by the program (e.g., plugging site of anastomotic leakage with biologic adhesive). On the other hand, if the size and flow rate of the leak required more aggressive treatment, an internal catheter or stent may be required. The anatomic and functional responses of bio-adhesive or stent placement could in turn be continuously monitored by circulating bots, with subsequent upgrading of the 4D anatomic map by the program.

In one embodiment, the derived bot data by the program, can provide an overview of data at systemic, organ, tissue, and cellular levels. While the concentration of these trauma biomarkers will be highest at the site of injury, elevated biomarkers can be detected at lower concentrations in areas far removed. Through circulating bots, the program can first identify the presence of trauma biomarkers and then validate the data abnormality by continuous measurements of numerous bots. Once validated, the site of tissue injury can be localized through continuous data collection of circulating bots with anatomic location tracking. As the concentration of the biomarkers reaches its highest discernible levels, targeted bots can be directed to the anatomic region of interest for the purpose of fine tuning the injury location. Once these bots have localized at the specific site of injury, additional data can be recorded and analyzed by the program to quantify the severity of injury, assess progression of tissue/organ damage over time, identify potential intervention options, assess the response to therapeutic intervention, and predict clinical outcomes. Examples of organ specific trauma biomarkers include (but are not limited to) glial fibrillary acidic protein (brain), kidney injury marker-1 (renal), cardiac troponin (heart), intestinal-type fatty acid binding protein (gastrointestinal), intercellular adhesion molecule-1 (lung), cytokeratin-18 (liver), and miR-216a (pancreas). In addition to these direct biomarkers specific to tissue/organ injury, other biomarkers can serve to identify adverse sequela of trauma such as d-dimer with coagulopathy, C-reactive protein with sepsis, and angiopoietin-2 with vascular instability.

Bot Derived In-Vivo Tissue Sampling and Collection

In one embodiment, DNA, cellular, tissue sampling and/or specimen collection can be accomplished through biopsy/aspiration needles, suction apparatus, and storage reservoirs 108 contained in the bots. Since the storage containers are size restricted in accordance with the physical size of the bots, they will routinely accommodate relatively small sample sizes. When larger size/volume specimens are required, they can be obtained through the combined efforts of multiple bots 100 acting in tandem within the same anatomic region of interest. The exact anatomic location, cell/tissue type, method of specimen collection, identity of the performing bot, and date/time of sampling is recorded by the program to accompany the specimen received. This supporting time-stamped and bot-specific data is of particular importance when a single anatomic location/specimen source is used for multiple/sequential sampling over time.

In one embodiment, some specimen analysis can be performed in-vivo, either within the confines of the acquiring bot or within a larger storage receptacle 135. This analysis would be subjected by the program to internal quality control (QC) and quality assurance (QA) tests (discussed later), which are aimed at ensuring that the acquired data has been validated for accuracy and the miniaturized biosensor technologies used in the analysis by the program have been appropriately calibrated and tested on a routine basis. Since the vast majority of derived data will be recorded by multiple individual biosensors, any variation in inter-sensor quantitative and/or qualitative measurements will serve as a trigger for additional testing, in order to identify and correct any individually deficient biosensor. When larger sample volumes are required for diagnosis and/or therapeutic actions, external transfer from the "acquisition" bot to an external storage bot or device 135 is often required. In addition to the intrinsic data associated with each individual biopsy/aspiration specimen, each specimen may require physical tagging in order to differentiate one specimen from another, since large numbers of individual specimens may be required to fulfill the requisite diagnostic and/or therapeutic requirements.

In one embodiment, upon transfer to a secondary storage device 135, the individual specimens may be collectively pooled or compartmentalized, depending upon the desired function and tissue of origin. As an example, for the purpose of therapeutic aspiration of a small infection (e.g., early abscess formation), it is not important to maintain separation of the multitude of aspirated specimens. As a result, multiple specimens from the same infection source can be collectively pooled into a single storage reservoir 108, 135, from which it can be analyzed by the program (e.g., microbiology, cell count, antibiotic sensitivity) and later disposed of.

In one embodiment, a diagnostic example when multi-bot specimens can be pooled is when a macroscopic mass from a single tissue source (e.g., liver, lung) undergoes biopsy for diagnosis. Since multiple biopsy specimens can be expected to be analogous to one another they can be pooled into a single storage device 135 and undergo diagnostic testing in unison, by the program. Alternatively, if cellular/subcellular specimens are being collected on a microscopic level or in a non-uniform biologic environment, the specimens obtained from multiple individual bots (either at the same or different times) may require compartmentalization of the individual specimens, in order to prevent cross contamination and comingling of individual specimens, which may adversely affect diagnostic purity.

By the program linking support data to each individual specimen, the resulting analysis by the program provides bot-specific data related to the anatomic source of biopsy/aspiration, the identity of the performing bot, the date and time in which the action was performed, corresponding signal transmissions associated with the action, and any biosensor derived associated data.

Mapping

In addition to conventional methods of 2 dimensional (2D) and three dimensional (3D) data display and analysis (e.g., charts, graphs, heat maps), the program of the present invention has the ability to directly correlate in-vivo macroscopic and microscopic data specific to the anatomic location in which it was recorded and provide a unique ability to create 4-dimensional (4D) anatomic maps specific to single or multiple data measures, using mapping module 118. Since disease states typically run across a wide spectrum of severity, it is important that recorded data is placed in the context of this disease spectrum by the program. This provides the program with the ability to characterize disease severity (at a single point of time), identify trends in disease progression or regression, determine response to therapy, and produce disease algorithms for prognostication.

In one embodiment, in order to illustrate how these disease specific tissue and molecular anatomic maps can be created and utilized in clinical practice, an example of a patient with chronic liver disease (i.e., hepatitis), which may be the result of viral infection, excessive alcohol, drugs, or autoimmune disease, is disclosed. Two common complications of chronic hepatitis are cirrhosis (resulting in liver failure) and carcinoma (i.e., hepatocellular carcinoma). The net effect is that at any point in time, the liver in a patient with chronic hepatitis may have varying degrees of acute inflammation, chronic inflammation, cell death, fibrosis, and malignant transformation. Quantitative and qualitative analysis of the liver at both tissue and cellular (i.e., molecular) levels by the program, could provide critical insights as to the degree of hepatic compromise, distinction of different disease states, severity of disease, and specific anatomic locations of viable versus non-viable tissue (i.e., hepatocytes) versus malignancy.

In conventional clinical practice, this distinction of different states of liver disease are largely performed by macroscopic analysis which can consist of serum biomarkers or external medical imaging tests (e.g., CT, MRI). On occasion, a liver biopsy may be performed (either percutaneously or via open surgery) for additional microscopic analysis, but this is fraught with the increased morbidity associated with an interventional procedure. In addition, liver biopsies are focal in nature and as a result provide molecular analysis for a small an isolated area of the liver (thereby limiting molecular assessment of the remaining non-biopsied portions of the liver).

In one embodiment of the present invention, for the program to accomplish analysis of the liver disease, a testing method is provided which would provide comprehensive analysis of the entire liver, allow for specific anatomic localization of disease, provide for in-vivo analysis at both tissue and molecular levels, provide for continuous analysis over time, and provide objective assessment of therapeutic response (which is both anatomic specific and time sensitive). The ability to embed a variety of biosensors into circulating bots which can simultaneously record the specific anatomic location in which the data was recorded by the program, could theoretically provide this functionality. At the same time, the multifunctionality of bots provides for a bevy of other tasks to be performed including (but not limited to) biopsy, cellular collection, drug delivery, and anatomic localization.

Returning to the example of chronic liver disease, in one embodiment, sensors within the bots can perform a wide array of in-vivo bioassays at both tissue and molecular levels which provide the ability to differentiate disease states, quantify disease severity, and track treatment response. In the setting of chronic hepatitis, it is well established that many of these patients go on to develop cirrhosis and/or hepatoceullar carcinoma. By having the program having the ability to continuously monitor disease-specific in-vivo biomarkers, the program of the present invention has the ability to detect disease transformation at a much earlier level than is currently available, while also depicting the specific anatomic location in which this transformation is taking place.

For example, Biomarkers for Assessment of Liver Disease, include:
1. Hepatocellular Carcinoma
   A. Oncofetal and glycoprotein antigens (e.g., alpha fetoprotein, glypican 3)
   B. Enzymes and isoenzymes (e.g., des-gamma-carboxy prothrombin, gamma-glutamyl transferase, alpha 1 fucosidase)
   C. Growth factors and receptors (e.g., transforming growth factor beta, tumor specific growth factor, epidermal growth factor receptor family)
   D. Molecular markers (e.g., circulating nucleic acids, alpha fetoprotein mRNA, gamma-glutamyl transferase mRNA, albumin mRNA).
2. Cirrhosis: Direct markers for fibrosis
   A. Matrix deposition (e.g., procollagen, hyaluronic acid, type IV collagen, laminin)
   B. Matrix degradation (e.g., metalloproteinase enzymes [MMP] 1, 2 and 9).
   C. Cytokines and chemokines (e.g., transforming growth factors alpha and beta).

In one embodiment, using this anatomic specific biomarker data, bots capable of performing biopsy and/or cellular collection can be dispatched by the program to the anatomic area(s) of interest for the purpose of obtaining targeted tissue/cells for pathologic confirmation and detailed molecular analysis by the program. As this longitudinal data is collected and analyzed by the program over time, a dynamic four dimensional (4D) anatomic map of the liver can be created which defines different states and severity of disease in the liver, temporal change, areas "at high risk", and differential response to treatment. In the event that a patient with chronic hepatitis was to undergo liver transplant for treatment, these same analyses and anatomic maps can also be applied by the program to transplanted liver, which may be prone to similar and different disease states (e.g., rejection, graft versus host response, infarction).

In one embodiment, the program derived 4D in-vivo maps provide a combination of anatomic, physiologic, functional, and pathologic data for the user. These maps can provide in depth visualization of anatomy at cellular, tissue, and organ specific levels, which can be combined by the program with external data sources for multi-data source analysis.

The dynamic manner in which the program can display anatomic maps and changes in disease state can also be applied to iatrogenic changes in anatomy as well. In the prior example of chronic liver disease resulting in a liver transplant the original anatomy undergoes fundamental change following hepatic transplant. In addition to the placement of the new liver transplant, a number of other anatomic changes take place related to blood supply (e.g., changes in arterial and venous anastomoses), biliary duct drainage, and neighboring organ systems.

In one embodiment, on a macroscopic level, these changes can be visualized through external medical imaging (e.g., ultrasound, CT), however these do not provide in depth knowledge, functional assessment, or visualization at the cellular levels. In the example of a liver transplant, suppose a post-operative leak or stricture was to occur at the biliary anastomotic site which is too small to warrant immediate clinical ramifications. In this scenario, the complication would likely go undetected for a significant period of time until the accumulation or leakage of bile at the site of pathology was great enough to warrant overt clinical symptomatology. In addition, the compromised immune status of the transplant patient (resulting from anti-rejection immunosuppression medication) may result in a relatively minor infection caused by the biliary leakage to quickly result in bacteremia and life-threatening sepsis.

Disease Mapping

In one embodiment of the present invention, a bot may be used to customize disease mapping at organ, tissue and cellular levels. In particular, various disease states and pathologies are dynamic in nature (i.e., medical continuum), and may be active, quiescent, or in remission at any point in time. Some diseases are multi-organ system in nature (e.g., diabetes), while some are specific to an individual anatomic location (e.g., coronary artery disease). Using information derived from a variety of medical data sources, a customized disease map can be created by the program which serves as a reference guide to authorized individuals for depicting the various types and anatomic locations of medical disease and intervention. This customized disease map can be viewed on a display, at whole body, organ system, tissue, and cellular levels in accordance with individual and/or collective disease states. In addition, the dynamic nature of disease results in a constantly evolving disease map which can reflect minute, hourly, daily, weekly, or yearly change.

While most existing data sources are macroscopic in nature (e.g., CT, EKG, laboratory tests), the bots 100 of the present invention can provide detailed and granular data at the cellular and/or molecular levels, with the potential for earlier and more accurate disease detection and response to therapy. Thus, disease maps can be prepared by the program to provide reference data at whole body, organ system, tissue, and cellular levels for a variety of diseases, with a specific focus on, for example, vascular disease at the level of the heart.

In one exemplary embodiment, such as a localized infection, the ability of the program to continuously analyze data from neighboring bots in a fixed location using the location module 120 of the computer system 100, also provides critical information related to the anatomic spread (or shrinkage) of inflammation and/or cellular migration. While this data could also be derived by the program from circulating (i.e., mobile) bots, the sensitivity and specificity of the data is far superior for stationary bots in a fixed location at the infection site for they are in direct proximity to the infection nidus and their fixed location minimizes the impact of subtle positional changes at the time of data recording.

In addition to iatrogenic anatomic change, these program-derived anatomic and functional maps can also play a vital role in the setting of trauma. Conventional medical imaging and functional assessment tools are macroscopic in nature and typically require significant injury at the tissue/organ level before they become readily apparent. In addition, these conventional techniques are largely restricted to being performed in a traditional medical diagnostic setting (e.g., physician office, medical imaging department), which limits their applicability in the field. Subjects who may be at high risk for trauma (e.g., soldiers, contact sports performers) or excessive bleeding to minor injury (e.g., patients with a bleeding diathesis or on anticoagulation therapy) may be able to benefit from the ability of circulating bots to detect rapid changes in anatomy, flow, physiology, and pathology.

To illustrate how this might be applied, in one exemplary embodiment, a soldier in the field who has incurred penetrating trauma (e.g., ballistic injury) with a well-defined point of entry. The baseline anatomic map of the region of interest (as well as the entire body) is established and readily available, thereby providing an important baseline from which interval change can be assessed. For trauma, the principles variables for analysis would include physical anatomy, functionality, vascular flow, physiology, and pathology. In this example, the entry point for the ballistic injury was the right flank and no discernible exit wound was established. Since there is no external data source (e.g., medic), all information and analysis will be through circulating bots. Note that these bots may be already reside in the host body (i.e., baseline circulating bots) or be introduced through external injection performed by the injured soldier or a colleague. Potential injection ports include trauma entry site (i.e., local) or systemic (e.g., peripheral vein).

Over time, the derived organ-specific anatomic maps can be continuously updated to reflect the biologic and physical changes at the tissue level.

Cell Mapping

In one embodiment of the present invention, bots for differential cell identification and characterization are utilized within the host entity. Using the multifunctional diagnostic capabilities inherent in bots and embedded microsensors, bots can be used to provide information for the program to identify and characterize various cell populations in the host. The derived data by the program can subsequently be transmitted via wireless technology and the local area network (LAN) to a user who records the data in a database 115, and employs a program to create cell maps which depict the anatomic location, cell type, genetic markers, and biologic activity of the cells being analyzed.

A. Stem and Progenitor Cell Mapping

In one embodiment of the present invention, stem and progenitor cell mapping can be performed by the program, the mapping which can have a number of medical applications, particularly in disease states resulting in cell death, injury, and/or malfunction which can be treated through stem/progenitor cell transplantation.

One example is in the case of myocardial infarction (i.e., heart attack), in which critical myocardial tissue dies resulting in diminished heart function and/or electrical conductivity, which can result in death if left untreated. While externally derived fetal stem cells are an option for transplantation, an arguably preferable option is to harvest adult stem and/or progenitor cells from the host. In order to do this one must identify, characterize, and localize potential stem/progenitor cell candidates using the program. Once this is completed, the program can create a host-specific stem/progenitor cell map which provides an up to date graphical display of existing stem and progenitor cell populations throughout the entire body, encompassing multiple organ systems, tissue types, and anatomic locations.

In addition to a generalized overview of stem/progenitor cell distribution, the map can provide more in-depth and detailed information relating to individual cell characteristics (e.g., genetic markers, metabolism, differentiation potential) which may provide important data for determining optimal stem/progenitor cell candidates using the program, in the event that transplantation is indicated.

In this embodiment, an authorized end-user may select a specific anatomic region of interest containing stem/progenitor cells and request additional data. Once accessed, an in-depth analysis of stem/progenitor cell populations localized in the anatomic region of interest can be prepared by the program, which provides an authorized healthcare provider with the ability to identify candidates with the highest chance of transplantation success, specific to the clinical indication.

Alternatively, in another embodiment of the invention, an authorized provider may input the specific stem/progenitor cell requirements for a given application and the program will provide a graphical display of the anatomic map on display 123 to show specific anatomic locations and stem/progenitor cell populations which fulfill the search criteria. In the example of a patient with a recent myocardial infarction requiring stem/progenitor cell transplantation, the physician is seeking to identify qualified stem/progenitor cells, with a preference for cells localized in the heart. After inputting the search criteria, the program will display the map and show stem/progenitor cells located in the heart, on the display 123, which fulfill the inputted transplantation requirements.

In one embodiment, a program which receives the data transmitted from the bots would display the data on computer display 123. The end user could scroll through a number of display options on the display 123 to view the specific version of the stem cell map of interest. In one embodiment, the stem cell map could appear as a whole-body image which shows the distribution of stem and progenitor cells throughout the entire body. In another embodiment, the user could highlight a specific population of stem cells of interest by identifying the region of interest on the displayed image, through multiple input options (e.g., speech, electronic stylus, text), and the program could present the user with a magnified graphical display which shows the specific anatomic region of interest in far greater detail.

In one embodiment, the stem cell map would depict the location and distribution of stem cells, population density (i.e., concentration), cell type of origin, and differentiation potential. Differentiation potential is important because it provides a biologic measure of the stem cell's potential to successfully differentiate into the tissue/cell type of interest. In the example of a stem cell transplant in the treatment of cardiac infarction, the harvested stem cells may arise from another organ system (e.g., skin, bone marrow) with the goal of differentiating into functioning myocardial cells (i.e., myocytes). For the purpose of graphical display, the program can show the stem cells which can be classified in accordance with their differentiation potential using the following schema:

0: Unknown differentiation potential
    1: Low differentiation potential
    2: intermediate differentiation potential
    3: High differentiation potential In one embodiment, the end-user may wish to view only a version of the stem cell map on the display 123, showing only those stem cells deemed category 3 (High differentiation potential). The program may identify six populations of grade 3 stem cells (i.e., skin, brain, bone marrow of left arm, bone marrow of right hip, heart, and left kidney). The user would then select on the display 123, those regions of greatest interest (e.g., heart) and then request that the program show a magnified display of these category 3 stem cells located in the heart.

B. Stem and Progenitor Cell Harvesting

In one embodiment related to stem cell transplantation, stem cells 400 are harvested from a host patient and subsequently transplanted at the site of disease (e.g., myocardial infarction), and the multifunctional bots of the present invention will be used to identify and characterize autologous stem and progenitor cell populations in the host (i.e., patient), harvest those stem cells of greatest relevance to the disease state, transplant cells at specific locations of disease, and then utilize the program to monitor myocardial cell function (pre and post intervention) and ascertain the relative success of the intervention (see FIGS. 4A-F).

More specifically, in one embodiment of the present invention, once the specific anatomic locations of stem/progenitor cells 400 have been determined by the program, these cells 400 are harvested so that subsequent transplantation can take place at the specific site of disease (i.e., see FIG. 4F). While current medical practice entails harvesting stem/progenitor cells 400 outside of the host (i.e., in vitro harvesting), the present invention provides the means in which stem/progenitor cells 400 can be harvested within the host (i.e., in-vivo harvesting).

In one embodiment, once the stem/progenitor cell 400 candidates have been screened and analyzed by the program, the specific locations of stem/progenitor cells 400 selected as donors for transplantation are selected by the program and the respective anatomic locations are provided to specialized bots 401 whose job is to retrieve (i.e., harvest) the selected stem/progenitor cells 400 and transport them to the specific transplantation site (see FIGS. 4A-4F).

In one embodiment of the invention, the same bots 400 tasked with stem/progenitor cell 401 retrieval also serve to transport the retrieved stem/progenitor cells 400 to the transplantation site, whereas in another application, the bot 401 tasked with retrieval may transfer the harvested stem/progenitor cells 400 to another bot 401 which will then deliver it to the site of transplantation.

C. Stem and Progenitor Cell Transplantation

In one embodiment, once properly harvested, the sequestered stem/progenitor cells 400 are transported to the specific anatomic region 402 of concern and strategically transplanted in accordance with clinical and anatomic requirements. In certain clinical scenarios a more detailed transplantation plan may be required so as to ensure maximal success.

In an exemplary embodiment of a stem/progenitor cell 400 transplantation following myocardial infarction, a detailed anatomic map is created by the program which delineates the full extent of myocardial cell death, along with the affected anatomy and clinical ramifications. In the example cited, a highly important electrical pathway was adversely affected by the infarction, resulting in abnormal electrical conductivity and arrhythmia (which resulted in need of a pacemaker).

In one embodiment, in order to improve the clinical success of the stem/progenitor cell transplantation a hierarchy was assigned by the program to the harvested stem/progenitor cells with the highest rated cells 401 allocated for transplantation at the most clinically significant anatomic locations within the infarction site. One of those "critical" locations was the myocardial cells 402 in and around the location of the AV node, which is responsible for electrical conductivity. As a result, stem/progenitor cells 400 with the highest likelihood of clinical success and restoration of normal myocardial activity are selected by the program for transplantation at this location.

In an alternate embodiment, cells 400 deemed of lower potential are strategically positioned at the periphery of the infarction site and far removed from electrical pathways. This ability of the program to prioritize and selectively allocate stem/progenitor cell transplantation through selective bot delivery and implantation is a unique application of the present invention.

D. Post-Transplantation Monitoring

In one embodiment, a unique advantage of the invention is the ability of the program to perform post-transplantation monitoring of cardiac function and cell viability, based upon the ability of the multifunctional bots to continuously perform bioassays at and around the transplantation site. In this embodiment, bots can continuously collect data at the transplantation site for the program to assess the relative success or failure of the transplanted cells to resume myocardial function (e.g., contractively, electrical conductivity). This bot-derived data at the cellular level can in turn be correlated by the program with macroscopic myocardial data (e.g., EKG, echocardiography) to determine myocardial function and biologic activity at both the cellular and organ levels.

In one embodiment, following completion of the stem/progenitor cell transplantation at the specific site of myocardial infarction, bots and their embedded biosensors continuously record a variety of data for the purpose of the program assessing changes in myocardial functional status as well as potential post-procedural complications. This data is used by the program to provide the authorized healthcare providers with real-time longitudinal data which can be used to guide additional decision making (e.g., pharmacologic therapy, re-transplantation).

E. Patient-Specific Map

In one embodiment, the program can create a comprehensive 4D in-vivo patient-specific biologic map, which records, analyzes, and continuously updates a variety of biologic data on a cellular, tissue, and organ specific basis. The map incorporates the real-time data being collected by the program in accordance with the anatomic site of origin and ongoing intervention (e.g., drug delivery, microsurgery, embolization) and displays it into a 4D graphical representation which highlights interval change over time. The authenticated end-user can selectively view this data on the display 123 in part or in totality based upon their occupational status, clinical focus, and authorization privileges.

In an exemplary embodiment, a pulmonologist who is treating a cancer patient for new onset of pneumonia would want to limit their clinical analysis to the lungs, with an emphasis on bioassays and biomarkers linked to infection, with temporal analysis closely following new or change in antibiotic regimens. In addition to global analysis of the lungs, the pulmonologist may designate a sub-anatomic region of primary concern (e.g., posterior segment right upper lobe), which is specifically localized to the site of new onset pneumonia. In addition to these macroscopic anatomic and disease specific analyses by the program, the pulmonologist may request more detailed analyses at the bronchial, bronchiolar, alveolar, and cellular levels; which effectively takes into account the infection nidus at the most fundamental (i.e., cellular) level, along with adjacent incremental anatomy. This ability of the program to provide longitudinal real-time hierarchical disease (i.e., clinical context) and anatomic specific analysis is a unique attribute of the present invention and can be represented in text and graphical descriptive forms by the following descriptors:

A. Clinical Context: Inflammatory and Infectious Biomarkers and Assays

A wide array of biomarkers exist for analysis of infection which may be both generalized and organ specific. A list of potential representative biomarkers for Infection and Inflammation include:
1. White blood cell (i.e. leukocyte) count
2. Erythrocyte sedimentation rate (ESR)
3. C-reactive protein (CRP)
4. Soluble triggering receptor expressed in myeloid cells (sTREM-1)
5. Pro-adrenomedullin (ProADM)
6. Serum procalcitonin (PCT)
7. Mid regional proatrial natriuretic peptide (ANP)
8. Interleukins (IL-6, IL-8, IL-27)
9. Presepsin
10. Soluble urokinase-type plasminogen activator receptor (suPAR)
11. Serum amyloid A (SAA)

In addition to inflammatory markers and chemicals, alveolar macrophages are of primary importance in pulmonary infections and are responsible for the activation of lysosomes, proteases, complement, thromboplastin, and cytokines. As a result, quantification and analysis of macrophage migration by the program is of utmost importance in the diagnosis and assessment of treatment response in pulmonary infections.

A. Anatomy of Interest: Lungs
1. Trachea
2. Mainstream bronchi
3. Lobar bronchi
4. Segmental bronchi
5. Terminal bronchioles
6. Respiratory bronchioles
7. Alveolar ducts
8. Alveolar sacs
9. Alveoli
10. Cellular and subcellular
   a. Alveolar epithelial cells (Types I and II pneumocytes)
   b. Epithelial call basement membrane
   c. Interstitial space
   d. Capillary basement membrane
   e. Capillary endothelial cells In one embodiment, the authorized end-user can identify the specific area of desired analysis by the program, using a variety of anatomic data inputs including (but not limited to) text, medical imaging, anatomic maps, photographic images, endoscopic capsules, surgery and interventional procedures, procedural notes, or clinical test data.

In this example of a pulmonologist seeking to evaluate pulmonary infection, the pulmonologist could input the anatomic location of interest (e.g., right lower lobe), select image/s from an imaging exam (e.g., chest CT) demonstrating the specific pathology/anatomic region of interest, graphical annotations of an anatomic reference map, photographic images from bronchoscopy, or textual data from the bronchoscopy report. Regardless of the method employed for anatomic localization, the inputted data would in turn be used by the program to identify and annotate the area of anatomic concern on the 2D or 3D patient-specific anatomic reference map and present this annotated graphical display to the authorized end-user on display 123, for confirmation. The end-user would then be given the option by the program to accept, modify, or cancel the program-derived anatomic referenced area of concern. Included in the option by the program to modify the anatomic area, would be the ability to expand or contract the anatomic region of interest along with modifying the search area to a more granular level (e.g., modify the original input data of right lower lobe segmental bronchus to an alveolar sac within the posterior segment of the right lower lobe). In addition to having the human end-user input the anatomic selection criteria, artificial and computer-derived intelligence can be used by the program for anatomic localization input. In this application, data mining from a variety of data sources (e.g., chest CT report, bronchoscopy, spirometry, lung biopsy) in the patient electronic medical record (EMR) can be used by the program to identify potential targets for analysis and present this to the authorized end-user on the display 123 along with the supporting data used. The end-user can then elect to accept, reject, or modify this program-derived anatomic data for further analysis by the program.

Once the anatomic region of interest and clinical context has been finalized and submitted for analysis to the program, the longitudinal data being recorded, collected, and analyzed by the bots is used by the program to generate a targeted 4D anatomic map in accordance with the selected search criteria.

In addition to single anatomic maps, in one embodiment, the program can create multiple anatomic maps for analysis and review based upon the clinical context, anatomy/organ system of interest, and the degree of anatomic detail. For example, in the case of the pulmonologist interested in analyzing temporal change of infection markers in the right lower lobe pre- and post-treatment, both macroscopic and microscopic analyses might be requested. For macroscopic analysis, the pulmonologist might use selected images from the recent chest CT exam to highlight the macroscopic area of interest. By highlighting the pathology in question (i.e., pneumonia) on the CT images (in both axial and coronal orientations), a 3D volumetric region of anatomic involvement within the posterior segment of the right lower lobe is derived by the program and used to create the corresponding 4D anatomic map. Since both retrospective and prospective data from the selected anatomic region of interest can be used to create the 4D anatomic map, the derived analysis by the program shows temporal change of infection biomarkers, assays, and corresponding clinical data (e.g., white blood cell count, fever, microbiologic sputum culture) over time. In addition, various therapeutic actions (e.g., initiation and/or change in antibiotics, respiratory therapy) can be directly incorporated into the analysis and anatomic maps by the program to show the cause and effect relationship between disease and various therapeutic interventions.

Personalized Medical Analysis

In one embodiment, the program of the present invention can customize the biosensor data and derived analyses for each individual patient. Since bots provide the ability to continuously collect in-vivo data over prolonged periods of time, the program can effectively create a patient-specific time sensitive biologic profile which can be subdivided in accordance with individual disease, anatomy (e.g., organ system), and therapeutic intervention. This can be particularly valuable in the setting of recurrent and/or chronic disease.

In one exemplary embodiment, a patient has a chronic vasculitis, so that the program identifying periodic changes to biosensor-derived inflammatory data can prove valuable in identifying early disease recurrence once a disease and patient specific profile has been created by the program. On the other hand, if the patient is developing an acute bacterial infection, the associated data profile compiled by the program would be expected to appear differently with respect to the magnitude, temporal change, and location of elevated biomarkers. When the same patient is being treated for intermittent bouts of acute vasculitis, the drug-specific biomarker response will provide data that the program can analyze to determine the therapeutic efficacy for this disease and specific patient. The program can combine the patient, disease, and drug specific biomarker derived data from large patient populations, such that important treatment specific data can be analyzed and identified by the program as to how individual therapeutic options differ in accordance with specific patient attributes (e.g., age, comorbidities, disease severity, genetics), macroscopic clinical data, and biomarker profiles.

As nanotechnology continues to evolve, the number and diversity of biosensors and bot functionality will exponentially expand, along with the clinical applications of the invention. As data analysis shifts from the macroscopic to microscopic levels, biomarker derived data analyzed by the program can provide analyses related to cellular dysfunction including (but not limited to) aging, atrophy, hypertrophy, hyperplasia, metaplasia, dysplasia, neoplasia, necrosis, and oxidative stress. Since the bot-derived data can be localized in time and location, this biosensor derived analysis by the program of cellular dysfunction can be localized to the specific organ system, anatomic location, and tissue of origin; with longitudinal data analysis to document cellular response to therapeutic interventions being generated by the program over time.

Merger of Multi-Source Anatomic Data

In addition to in-vivo (or internal) bot anatomic localization, in one embodiment, the anatomic data can also be correlated by the program with external anatomic data, which may take the form of traditional medical imaging techniques (e.g., ultrasound, magnetic resonance imaging (MRI), computed tomography (CT)). In this application, the anatomic data provided by the conventional medical imaging exam can be correlated by the software program with in-vivo anatomic data provided by the fixed anatomic markers and/or bots.

In one exemplary embodiment, one can perform an abdominal CT exam of a patient with embedded fixed anatomic markers within the liver. If each individual fixed liver marker 133 contained a series of internal radiopaque sub-markers readily visible by CT (e.g., metallic, calcium, air), then the exact three dimensional location of the fixed marker 133 as well as its individual sub-markers can be readily identified by the location module 120, as well as their relative locations with adjacent anatomic and pathologic structures. If in this example, the patient had a liver malignancy (e.g., hepatocellular carcinoma) which was undergoing treatment (e.g., chemotherapy, cryotherapy, embolization, radiation), then in order to more accurately determine location of circulating bots relative to the liver cancer, one may first localize the bots 100 relative to the fixed anatomic markers 133, and secondly localize these fixed anatomic markers 133 within the entire liver, along with their proximity to the liver cancer. By the location module 120 correlating both "internal" and "external" anatomic and pathologic data in combination with one another, one can achieve more accurate anatomic localization of stationary and/or mobile bots, while differentiating individual bots on the basis of their own unique individual signal characteristics. (Note the deployment of these fixed anatomic markers 133 can be performed in a variety of ways, both through external placement (e.g., percutaneous needle, surgery) and through internal deployment (e.g., vascular catheter, smart medical device).

Automated and Customizable Data Alerts

In one embodiment, a unique feature of the present invention is the ability to utilize 4D microscopic and cellular data to provide real-time alerts to authorized providers in the event that a predefined data threshold has been reached. In the prior example of a liver malignancy, suppose the treating oncologist has requested that any real-time data analysis (either systemic or local) identifying an increase in inflammation biomarkers prompt an immediate notification pathway using an electronic alert module 117.

In one embodiment, the bot-derived data and analyses can in turn be used by the program to create automated alerts to authorized end-users based upon predefined data thresholds. In one exemplary embodiment, to illustrate the importance of automated bot-derived data alerts by the program, would involve a post-transplant outpatient who is receiving immunosuppressive medications in order to prevent transplant rejection. Since the immunosuppressive therapy places the patient at increased risk for infection (which can often be life threatening), it is of utmost importance that any infection be diagnosed and treated as early as possible. In addition to conventional pathogens, the state of immunosuppression places the patient at increased risk for unusual opportunistic infections which are not routinely seen in patients with intact immune systems. As a result, diagnostic methods must account for a wide array of potential pathogens, which is challenging by conventional methods and often leads to delayed diagnosis and treatment.

However, in the present invention, since the diagnostic tools and assays employed by bots can be customized by the program in accordance with each individual patient's unique clinical circumstances and genetic predilection; the physicians treating this post-transplant patient have opted a continuous diagnostic regimen which employs a variety of bioassays which include cellular and chemical markers for infection and ability to proactively collect in-vivo specimens (e.g., tissue, cellular, and RNA) for microbiologic culture and antibiotic sensitivity. Since the circulating bots have anatomic tracking capabilities, the specific anatomic location and organ system serving as the source of these early infection markers can also provide important information relating to the specific infection source (which is often lacking in conventional methods such as peripheral blood cultures). A predefined algorithm can be established by the program which identifies the threshold at which an abnormal and/or changing data measurement automatically triggers an escalation pathway which may include data verification (i.e., reproducing the data abnormality in question by neighboring bots), analysis of disease progression (i.e., through continuous bots data collection at the original anatomic source), determination of severity (i.e., correlation of observed data measures with established disease severity metrics for comparable patients), identification of pathogen (i.e., through deployment of collection bots 200 (see FIGS. 2A-2F) which possess the ability to collect biologic specimens for testing), and preliminary treatment (i.e., deployment of therapeutic bots armed with commonly employed antibiotics specific to the most commonly encountered infections related to the individual patient and clinical circumstance).

If the data abnormality in question has been verified and determined by the program to place the patient at significant risk (as relating to the individual patient and clinical condition), an automated alert is transmitted by the program to authorized clinical care providers. Note the programmed selection of the appropriate clinical care providers for notification is dependent upon a predefined notification schema, the occupational status of the individual provider, and the availability of providers. If the provider/s do not acknowledge receipt of the alert, then a clinical provider escalation pathway is initiated by the program to ensure that the alert is received and acknowledged within a predetermined time period and subsequent clinical action is taken.

In another exemplary embodiment of how automated alerts are important to patient outcomes can be seen in the setting of trauma, such as a soldier in battle. Before engaging in combat each soldier is injected with a baseline number of bots which are capable of providing continuous surveillance over a defined period of time commensurate with the time interval of concern. Once injected, these diagnostic bots circulate throughout the host bloodstream. Since the clinical application is specifically focused on trauma, the diagnostic capabilities employed are specific to signs of tissue injury and/or active bleeding. In the event that a real-time in-vivo measurement indicates post-traumatic injury as determined by the program, the anatomic location of the bots is determined by the program, and a signal transmission alerts circulating bots of the location of concern for additional data collection and analysis. These alerts are simultaneously transmitted by the program to authorized end-users notifying them of the abnormal data collection, the identity of the host (e.g., soldier), anatomic location(s) of injury, physical location of the host (i.e., geographic location), the severity of the abnormality, and its temporal progression. This provides for real-time in-vivo analysis and treatment planning "in the field".

In one embodiment, since the transmission of the automated alerts can be customized by the program based upon the individual patient, clinical situation, authorized list of providers, and provider availability, one can dynamically interact with readily available resources on an "as needed" basis. In this example, the solider in battle may have suffered a ballistic liver injury resulting in significant tissue injury and active bleeding; all of which can be objectively quantified by the program through actively circulating bots, which in turn can further direct targeted and continuous data collection and analysis by the program at the specific site(s) of injury. This real-time dynamic data can be automatically sent by the program to authorized medical personnel in both remote and local locations; who can in turn facilitate rapid real-time intervention. Remote healthcare providers (e.g., trauma surgeon) can be located back at the central medical hospital while the local (i.e., on the ground) provider may include a combat medic. Given the real-time data, the medic can prioritize which soldiers are in greatest need of his/her immediate attention, what intervention options are applicable, and what specific therapeutic options are available locally (i.e., in the field), versus what requires helicopter transport.

In another exemplary embodiment in the setting of trauma, a soldier in battle whom is shot in the right flank and is actively bleeding but remains conscious. In addition to baseline bots which are circulating in the soldier's bloodstream, the soldier also has in his possession at additional syringe filled with bots which can be locally injected at the site of trauma or injected intravenously upon injury. If locally injected at the wound entry site, the bots would have to have embedded active propulsion to ensure bot navigation in the soft tissues at the site of penetrating trauma. As these local bots travel along the ballistic pathway, they continuously collect data related to nearby anatomic structures, biologic analysis of surrounding tissue and fluid, and the overall size and depth of the post-traumatic wound site. At the same time, circulating bots (in arteries, veins, venules, and lymphatics) continuously collect data of relevance (which in this application is focused on trauma). The desired data would be collected and transferred by the program to a database 115, 125.

In one embodiment, the ability of bots to deploy an anatomic marker (e.g., suture, metallic clip, biodegradable patch) at a given anatomic location, provides one with the ability to define the initial boundaries of tissue/cellular injury and monitoring over time. As bots delineate the borders of pathology based upon real-time objective data recordings of embedded biosensors, the associated anatomic delineation can be identified through biomarkers (e.g., suture, clip) which provides the program with the ability to analyze pathology extension or contraction in accordance with the data abnormality of record. Since there is a continuum in the degree of data abnormality, the markers employed can differ from one another based upon the magnitude of the data abnormality or a predetermined degree of data abnormality can be employed to delineate the boundaries in which the data abnormality warrants anatomic localization. As long as the same standard is utilized when implanting anatomic localizers, consistency exists for tracking and analyzing anatomic change in pathology. In some circumstances anatomic change in pathology borders can be extremely slow (e.g., tumor), intermediate (e.g., abscess) or extremely rapid (e.g., active hemorrhage). The ability of the program of the present invention to continuously track and analyze anatomic positional change of the pathology provides both an objective method of in-vivo disease surveillance at the tissue and/or cellular level as well as a method for mobilizing bots for continuous data collection, analysis, and intervention by the program.

In one embodiment, by incorporating the ability to transmit localizing signals (i.e., analogous to a beacon), these anatomic markers can provide active guidance to circulating bots as to the specific anatomic location of interest for performance of their specific duties, which may be diagnostic or therapeutic in nature.

Data Analysis

In one embodiment, the data resulting from bot communications can be transmitted via wireless technology and stored by the program in both local and central databases 112, 115, 125. Database size for local storage 112 at the level of the bots, will keep expanding over time. In-vivo local storage devices and networks can also be established at the level of the tissue/organ system level (e.g., liver, heart, skin), in which small implantable storage devices 135 can transmit and receive signals with in-vivo bots which can record the day/time, duration, identification of the bots (i.e., data source), anatomic location, and intrinsic biologic data. This same data can also be stored at external data storage devices 115, 125, where the program can analyze large volumes of data from multiple data sources, organ systems, and time periods. This combined data can in turn be communicated by the program with the conventional individual patient electronic medical record which currently records a variety of "macro" data (e.g., imaging studies, laboratory data, pharmaceuticals, treatment plan, medical diagnoses, surgical history, etc.). The ability to actively record, track, analyze, and cross reference these combined "in-vivo micro" and "macro" medical databases 125 creates synergistic real-time data analysis.

In one embodiment, in addition to intra-patient in-vivo data analysis, the bot's data derived from these local and central databases 112, 115, 125 can also be used for large sample size patient analysis, which is the principle behind population medicine and evidence-based medicine. By the program correlating this bot's derived data from the patient of record with similar bot-derived data from large numbers of patients with similarities in disease state, predictive analytics can be derived which provide diagnostic and therapeutic guidance. Since the present invention provides in-vivo medical data at the cellular and subcellular levels, earlier diagnosis and intervention would now be made available to the clinician which could dramatically impact both the timeliness and accuracy of diagnosis as well as successful clinical outcomes.

Data Standardization

In one embodiment, a number of standardized time stamped data are recorded by the program during the performance of bot duties. These include identification of the individual bots 100, in-vivo anatomic location in which the action took place, identity of the host (e.g., patient, animal), pertinent patient-specific clinical data (e.g., disease, lab data, pharmaceuticals), specific action performed (e.g., bioassay, tissue collection, chemical release), corresponding quantitative measurement (when applicable), and duration (i.e., period of time) required for completion of the action performed. In the situation in which multiple micro-sensors 102 etc., are contained within individual bots 100, the specific location and sensor type associated with the data is recorded by the program in the database. This resulting time stamped data can in turn be locally stored 112 or transmitted via wireless technology to a local storage network 115 (from which it can in turn be transmitted to a central database 125 on a network).

In one embodiment, the resulting time-stamped synchronous and sequential data from large numbers of bots allows the program to create a quantitative, objective, and real-time data-driven in-vivo biological system which can combine disparate data from numerous types of bioassays into a comprehensive patient, anatomic, and disease specific analysis. The program can track and analyze longitudinal data over time to identify emerging trends in disease diagnosis and treatment response and correlate these measurements and trends with data from comparable patients contained within the standardized central database 125. By the program's use of artificial intelligence, the derived and mined data from both the host and related patients can create a series of predictive data algorithms, which can assist healthcare providers in therapeutic decisions and selected interventions. Since the ongoing real-time data measurements can be directly assimilated by the program into these predictive analytics, the program can both identify emerging trends in disease progression/regression, while fine tuning and modifying therapeutic interventions. Unlike existing diagnosis and treatment planning, which is performed at a macroscopic holistic level, the present invention provides the means in which diagnosis and treatment can be performed at the cellular and tissue levels, which can in theory dramatically improve the accuracy, timeliness, and localization of both diagnosis and treatment.

Data and Multivariate Analysis

In one embodiment, individual patient specific anatomic maps can be combined by the program from multiple patients for the purpose of analyzing disease and anatomic specific interventions on a large numerical scale. In one exemplary embodiment, suppose one wishes to visualize and analyze treatment response to Pneumococcal pneumonia in all patients receiving a specific antibiotic over a 7-day time course. This can be done both individually and collectively by having the program superimpose the biomarker derived data from a large pool of patients who fit the search criteria of interest. This in effect can have the program provide a global visual analysis of infection and treatment response over time. One can modify the search criteria in a variety of ways to have the program provide more in-depth analysis in accordance with a given clinical scenario. Suppose the pulmonologist is dealing with an elderly patient who is immunocompromised by underlying diabetes. In order to derive more patient specific data, the selection criteria can now be modified to include all patients who fulfill the following search criteria:

1. Primary Clinical context: Pneumococcal pneumonia
2. Patient specific criteria: Age >80 years of age
3. Anatomy of Interest: Lungs
4. Additional clinical variables: Diabetes
5. Therapeutic intervention: Levofloxacin In this embodiment of the invention, the authorized end user can have the program search the database 115, 125 to identify all patients who fulfill the search criteria of interest and have the program generate multivariate anatomic maps with the combined data from the entire pool of qualified patients. In addition to having the program present these anatomic maps in combined formats on the display 123, individual or small groupings of patient anatomic maps can be selectively reviewed.

In an exemplary embodiment, suppose the patient of interest is not responding to the treatment protocol as quickly as many of the comparable patients. The pulmonologist may request that the program seek out individual patients with "similar" anatomic maps. This includes a small subgroup of patients from the larger all-inclusive pool whose 4D disease specific anatomic maps most closely approximate the patient of record. In this example, the program will select similar patients whose disease severity and treatment response were most similar to the patient of record. The physician can then review specific medical data in these "similar" patients with the goal of obtaining useful information in their clinical history which might provide useful information for the current case. In this manner, the disease specific anatomic maps can be used for a variety of clinical applications, including decision support based on comparable data from larger patient data pools.

In the original example where the pulmonologist requested a macroscopic anatomic map of the posterior segment of the right lower lobe pneumonia (based on CT imaging data), the pulmonologist could also request a second microscopic anatomic map from the program, which provides more granular data at the cellular level of the alveolus. In this microscopic anatomic map bioassays, DNA analysis, and macrophage migration is analyzed by the program and displayed on display 123 to provide changes in biologic activity at the molecular level, pre- and post-treatment. This provides the clinician with disease-specific biologic data at both the tissue and cellular levels, which may prove to be synergistic in diagnosis and treatment planning. The net effect is that 4D disease specific anatomic maps literally and figuratively come in a variety of size and shapes and can be customized in accordance with the individual preferences and needs of the authorized end user.

As previously stated, the derived 4D disease specific anatomic maps of the present invention can display both diagnostic and therapeutic data, as well as provide merged data from other medical information sources. This ability of the program to record, quantify, compare, and correlate real-time multidisciplinary medical data is a unique application of the invention and can be customized in accordance with a specific type of disease, pathologic source, therapy, anatomy/organ system, or healthcare provider. To illustrate how this application of the invention works we can cite a few illustrative examples.

In the first example, suppose the patient has a multi-systemic disease such as rheumatoid arthritis (RA). While the polyarticular joint disease is the primary manifestation of the disease, which is believed to be autoimmune in etiology, other organ systems may be involved including vascular (e.g., vasculitis), ocular (e.g., scleritis), pulmonary (e.g., interstitial lung disease), cardiac (e.g., pericarditis), skin (e.g., nodules), renal (e.g., glomerulonephritis), neurologic (e.g., sensorimotor neuropathy), and hematologic (e.g., anemia). The high degree of variability in disease severity, anatomic involvement, and progression often makes diagnosis and treatment problematic. While traditional medical practice has focused on "macroscopic" and external methods for diagnosis and treatment, the recent development of biomarkers and biologic forms of therapy have created new possibilities for earlier diagnosis and more effective treatment. In one embodiment of the present invention, these biomarkers and biologic forms of treatment can be applied both microscopically and in-vivo, thereby creating the opportunity for early and anatomic specific diagnosis by the program along with the ability to monitor and assess treatment response at the cellular level.

Four stages exist for the clinical assessment and treatment of RA which are Diagnosis, Prognosis, Monitoring of Activity, and Treatment. For diagnosis, a variety of clinical tests (e.g., erythrocyte sedimentation rate (ESR), C-reactive protein) and medical imaging tests (e.g., x-rays, CT, MRI) are commonly employed. For prognosis and disease monitoring a variety of biomarkers are utilized, the number and type of which are continuously expanding. Examples of RA specific biomarkers include (but are not limited to) rheumatoid factor (RF), anti-citrullinated peptide antibodies (ACPA), antibodies against carbamylated proteins (anti-Carp), 14-3-3 eta protein, antibodies against mutated citrullinated vimentin (anti-MCV) and cartilage oligomeric matrix protein. Medical treatment includes a wide array of drugs and biologic response modifiers, along with alternative forms of therapy (e.g., fish and plant oils). Surgical treatment may include synovectomy, tendon repair, joint fusion, and/or joint replacement. The more invasive forms of therapy are often related to those patients who have either delayed/late diagnosis and/or failed medical treatment.

The ultimate goal in RA would be to develop medical strategies leading to earlier and more accurate diagnosis, enhanced prognostication and monitoring of disease severity and multi-system involvement, creation of more effective treatment strategies with less side effects and toxicity, and the ability to proactively and objectively measure treatment response. A number of existing metrics are currently used to quantify disease activity including the disease activity score (DAS 28), simple disease activity index (SDA 1), and clinical disease activity index (CDA 1). While these serve an important function of objectifying the measurement of disease, they largely rely on "macroscopic" measures which quantify disease on large scale levels. A far superior strategy would be to objectively measure and quantify disease at the molecular or cellular levels, which would in theory provide more effective methods for earlier and more accurate diagnosis, disease prognostication and evolution, and earlier and more effective treatment.

In one embodiment, one could apply the present invention to the diagnosis and treatment of rheumatoid arthritis, and a number of 4D anatomic maps could be derived by the program. Circulating bots can continuously provide measurements of disease-specific biomarkers, along with the identification of the specific anatomic location from which these bioassays were recorded. If abnormal levels of biomarkers are recorded by the program, additional disease-specific biomarker assays can be performed by the bots through the deployment of other types of biosensors embedded within bots. Alternatively, biologic specimens (e.g., blood, fluid, cells, DNA) can be continuously collected through bots with aspiration capabilities and collection reservoirs 108, which would allow external analysis of the in-vivo specimens with well-defined anatomic localization of the specimen.

As these various bioassays are continuously recorded and analyzed by the program along with their associated anatomic locations of origin, anatomic maps can be derived by the program which can provide quantitative analysis of the individual bioassay over time, which in turn can be correlated by the program with related bioassays. The quantitative data from multiple bioassays can in turn be used by the program to create a multi-biomarker disease activity test (MDMA), which provides combination data of multiple biomarkers, which can in turn be correlated by the program with a variety of external clinical and imaging data (e.g., clinical exam, blood tests, x-rays). As large sample size data is collected by the program from a wide array of patients, this biomarker data can be used by the program to provide predictive analytics for the combined purposes of enhanced disease prognosis, evolution, multi-systemic involvement, and treatment response (to both pharmaceuticals and biologic therapies).

In one embodiment, as new data is collected, trending analysis is performed by the program which is directly incorporated into the 4D disease-specific anatomic maps to provide a visual display of disease severity, progression, and response to treatment, on display 123. These visual maps can be further subdivided or segmented by the program to display biomarker measurements in isolation or specific combinations, with or without correlating clinical and/or imaging test data so that an authorized healthcare provider or researcher can specifically visualize temporal change in a variety of data points. This may provide important insights as to which biomarker and/or clinical data is best suited for diagnostic and therapeutic analysis in a given disease, anatomic location, or individual patient. The 4D visual display presentation parameters can be customized by the program to optimally visualize differences in data magnitude, temporal change, and/or relationship to an external event (e.g., imitation of a new biologic therapy). The goal is to provide an intuitive form of visual display which provides the authorized end-user with an overview of clinical data without the need for supplemental text-based and/or numerical data.

The present invention provides the capability of displaying bot-derived data in a wide array of anatomy, ranging from the molecular to whole body levels. In the example of a patient with multi-systemic rheumatoid arthritis, one provider (e.g., rheumatologist) may want to limit their review to an anatomic map of a single joint (e.g., right knee), while another provider (e.g., cardiologist) may want to limit their review to a single organ (e.g., heart), and another provider (e.g., pharmacologist) to a whole body image. In the case of the whole body image which is being presented on the display 123 by the program, to visualize the entirety of multi-systemic involvement, the reviewer would have the capability of reviewing the number of active disease locations, the relative severity of involvement within individual organ systems, the temporal change of involvement over a predefined period of time, and the specific response of each site to different forms of treatment.

In the same example of a patient with systemic rheumatoid arthritis, suppose the patient has recently begun to experience respiratory symptoms (e.g., shortness of breath), requiring more in-depth evaluation. The patient undergoes a series of tests including chest CT, spirometry, arterial blood gas measurements, pulse oximetry, and blood cell count. These tests reveal that the patient has diminished lung capacity, decreased oxygenation in their blood, a mildly increased white blood cell count, and interstitial disease in the lungs. The provider is uncertain whether these changes are the result of a viral infection, rheumatoid involvement of the lungs, or a complication of medication. While a lung biopsy would likely provide more definitive diagnostic information, it would be invasive in nature and would be limited to the small area in which the biopsy was performed.

Using the present invention, circulating bots could be used to obtain a variety of data throughout different areas of the lung including biomarkers for RA and infection, drug assays, and oxygen/carbon dioxide measurements. In addition, the bots can collect cell/tissue samples from different anatomic regions in the lungs, which in turn can be directly correlated by the program with chest CT. By the program correlating the clinical/imaging data with the bot-derived data over time, a 4D anatomic map can be derived which identifies specific regions of pathology throughout the lung fields, the diagnosis and severity of disease, disease progression over time, and the response to various treatment regimens. In addition, the RA biomarker data can be correlated by the program with data of similar biomarkers in other anatomic regions (e.g., joints, skin, heart) to determine the extent of systemic involvement, relative severity in different organ systems, and changes in the biomarker profile within different anatomic regions. This biomarker profile data can in turn be used by the program to calculate a variety of quantitative disease metrics (e.g., MDMA), which can provide important prognostic and therapeutic data. In addition, this data and derived metrics can be correlated by the program with genomic data to determine the influence of genetics on disease expression and treatment response.

In one embodiment, the 4D anatomic maps derived by the program from bot data can be combined by the program with a variety of other anatomic data sources including (but not limited to) 2D and 3D imaging data, medical photography, endoscopic procedures, endoscopic capsules, and surgery. Since the program continuously assimilates new data into the 4D anatomic maps in order to provide temporal change, these 4D anatomic maps are continuously evolving. One option is for the program to display those anatomic areas over a defined period of time, in order to present the authorized end-user with a quick and intuitive method for visualizing quantitative and/or qualitative change. In the prior example of the patient with diffuse rheumatoid involvement of the lung interstitial, a sudden increase in biomarkers to a focal location would be indirect evidence to suggest a new disease process superimposed upon the diffuse RA involvement. By the program visually displaying this focal area of sudden change along with the specific biomarkers and severity of measurement, the provider can be directed as to the need for alternative diagnosis, additional test requirements, and treatment options. This may be otherwise overlooked if the method for data display is solely based on numerical data alone.

Real-Time Analysis

In one embodiment, real-time data requirements is a dynamic process requiring continuous adjustment in nanobot and biosensor functionality and anatomic localization. In order to best accomplish the task of real-time data collection, analysis, and intervention a methodology is created which provides both computerized and human input for continuous adjustment to available biomedical resources. As an example, if evidence of active bleeding is identified by a circulating nanobot which is subsequently confirmed by a second nanobot, the subsequent readjustment in resources is commensurate with the clinical severity which can be determined by a variety of data measurements including (but not limited to) the magnitude of an individual data measurement, the breadth of abnormal data (i.e., the size of the anatomic region affected), the change in measurement over time (i.e., temporal change), and secondary change in ancillary data (e.g., systemic drop in blood pressure, arterial shunting in non-essential anatomic structures (e.g., superficial blood flow). Based on this real-time data analysis, an automated (or human) response can be elicited by the program which determines the number of reallocated nanobots, the specific biosensor requirements (for diagnosis and/or treatment), the anatomic region/s of interest (including a topographic map for distributing individual nanobots to a specific anatomic region of interest based on differential data measurements). In the example of active bleeding from the liver, the highest concentration of nanobot data collection would occur in the identified epicenter of bleeding with gradually diminished nanobot concertation about the periphery of the bleeding site. The exact number of allocated nanobots, their respective locations, and the time interval between measurements would be commensurate with the size and severity of the bleeding along with the response to intervention.

While conventional medical data collection and analysis is primarily disease and organ specific, the present invention provides the ability to analyze multiple disease states and multiple bioassays within an organ system simultaneously while also analyzing the organ system or anatomic site in accordance with detailed location. In one example, there is a situation of a cirrhosis in which the liver has been severely damaged as a result of chronic hepatitis and there is new evidence suggestive of an early cancer (i.e., hepatocellular carcinoma (HCC)). Conventional laboratory analysis provides a variety of blood tests for measurements of hepatic dysfunction (e.g., albumin, partial prothrombin time (PTT)), inflammation (e.g., aspartate aminotransferase (AST), alanine aminotransferase (ALT), hepatitis (e.g., anti-hepatitis C (HCV) antibodies, HCV polymerase chain reaction), and hepatocellular carcinoma (e.g., alpha-fetoprotein (AFP)). In addition to these blood tests, a number of medical imaging studies (e.g., ultrasound, magnetic resonance imaging (MRI)) can be used to identify abnormalities in liver anatomy and pathology, in both generalized and focal forms. While these blood and imaging tests are collectively helpful in diagnosing liver pathology, they are often nonspecific and require significant degrees of pathology before the appropriate diagnosis can be made. A preferable approach would be to utilize bioassays which can both identify and localize disease at a molecular level when intervention would have its greatest clinical impact, while also decreasing iatrogenic complications and morbidity associated with regional and/or systemic therapy. The present invention provides a method for early diagnosis, specific and detailed anatomic localization, and localized therapeutic intervention by utilizing nanobots and a variety of specialized biosensors to detect and localize disease at a cellular level.

Quality Control (QC) and Quality Assurance (QA)

In one embodiment, the quality assurance of bot emitter 129 functionality includes two primary components: positioning and emission quality. The positioning is continuously monitored by the location module 120 of the computer system 113 through the aforementioned motion sensors (i.e., sensor 102) embedded within the emission device/bot 100. The emission quality is continuously assessed by the program, using the quality assurance module 119, by the emission signals received by neighboring bots 100, which measure and analyze both the amplitude and quality of the emission signal. If for example, the emission signal begins to deviate from its designated radiofrequency or light wavelength or dissipate in intensity, it may be deemed by the program to be no longer operational and require extraction and/or replacement. This illustrates an important application of the present invention; in that the program calls for a series of internal quality assurance measures and test procedures to continuously monitor bot and biosensor performance and location.

In one embodiment, QC and QA are important (and often overlooked) components, since it is inevitable that technology (both hardware and software) will fail to some degree over time. In addition to hardware mechanical failure, which will adversely affect function, hardware and/or software malfunction has the potential to result in faulty data, which in any aspect of medicine may result in different forms of medical error, the most serious of which is death. If for example, the incorrect dose, type, or anatomic location of drug delivery was to occur using the invention, the results could potentially be catastrophic. On the other hand, data obtained from faulty biosensors could lead to the inclusion of erroneous data in derived medical analytics, which may result in faulty diagnosis and/or treatment. Since many of the applications described in the invention are exceedingly time sensitive (e.g., life threatening bleeding), the overall success of the invention and its applications are predicated on the accurate and timely identification and remedy of any technology deficiencies; which lies at the core of internal QC and QA.

In the present invention, QC can be defined by issues related to the various hardware components of the invention and deployed bots. Examples of bot QC include (but are not limited to) mechanical failure of bots or individual components contained within them (e.g., breakage of exterior or individual parts), transmission failure (e.g., inability to send or receive electronic transmissions), identification failure (e.g., inability to detect or accurately respond to requests for bot identification), or failure in functionality (e.g., inability to perform desired task such as drug delivery, cell/tissue collection, or bioassay).

In the present invention, QA refers to the ability of the program to continuously monitor bot derived data for the combined purposes of assessing data integrity, security, accuracy, and reproducibility. By the program continuously monitoring and analyzing the identity and data associated with each individual bot (or bot subgroups), the quality assurance module 119 can continuously and longitudinally analyze inter- and intra-bot data consistency and reproducibility. If for example, a number of miniaturized biosensors within a single bot are responsible for a single type of bioassay, one would expect the derived data from these micro-sensors would be relatively consistent over time. If, however, the program determined that the data derived from a single micro-sensor is different from data of neighboring sensors, one might be concerned that this individual micro-sensor is deficient in function. The same analogy can be made if the program determined that data from a single micro-sensor was to dramatically differ over time, relative to baseline data measurements performed by the same micro-sensor. The net result is that continuous data analysis by the program provides a reliable and readily available source of bot QA. By knowing the identity of each individual bot and the specific location of contained biosensors (and other bot components), the program can readily detect data outliers, which can in turn elicit more rigorous QA testing by the program. Since the derived bot data can be enormous in quantity and scope, computerized algorithms of the program can continuously monitor bot-derived data for consistency and provide automated alerts to authorized providers (as well as other bots), as to the potential for bot malfunction and/or erroneous data. In addition, once identified, the involved bots or its subcomponents may be effectively "turned off" by the program, thereby ensuring the erroneous data is no longer actively used in data collection and analysis.

In one embodiment, in the event that the QC or QA deficiency creates a serious danger to the host and/or desired clinical outcome, the involved bot may also be 'terminated" by the program, which may include removing it from active duty or have it be physically destroyed. In the example of "turning off" functionality of a given bot or subcomponent (e.g., biosensor), the offending component is decommissioned by the program, so that its actions and/or derived data will not affect the ongoing function of neighboring bots or other subcomponents contained within the same bot. Termination on the other hand, calls for the bot in question to be physically removed and/or destroyed, thereby ensuring that any mechanical deficiency and/or data will immediately cease. Termination can be performed in a variety of methods including (but not limited to) triggering an internal mechanism for self-destruction, external destruction by a "killer bot", or directed phagocytosis.

In one embodiment, in the event that a QC or QA deficiency is suspected, additional in-depth testing can be performed by the program for diagnostic and/or therapeutic purposes. Since the identity, individual subcomponents, architecture, functionality, and anatomic location of each bot is known and continuously updated, continuous bot specific QC and QA is achievable. In addition to continuous monitoring by the program (which can be more extreme in the case of a suspected QC/QA deficiency), additional options are available for QA/QC scrutiny in accordance with the individual bot of record, its subcomponents, and functionality.

In one embodiment, an additional option is the ability for the program to send a dedicated QA/QC bot to the location of the "dysfunctional bot" (since its anatomic location and identity is well established). Upon arrival to the location of interest, the QA/QC bot can engage with the dysfunctional bot through wireless transmission (using the specific radiofrequency of the dysfunctional bot) and direct it to physically "synch up" with the QA/QC bot. This physical attachment of bots can be facilitated through a specific built-in bot portal (i.e., attachment portal), which allows for authorized bots to physically attach with one another for a designated purpose. The QA/QC bot can in turn issue a series of targeted test signals to determine the functionality of the bot and/or its subcomponents. If for example, biosensors or a biopsy device located in a specific location of the bot are suspected to be dysfunctional, the QA/QC bot can deploy ultrasound, video, or photography to assess the structural integrity of the bot and its subcomponents in the location of concern. Alternatively, the QA/QC bot can transmit a command for the subcomponents to perform internal QA/QC as directed by the program. In the event that a structural and/or functional abnormality is detected by the program, which cannot be easily fixed, a decision can subsequently be made by the program and/or an authorized provider to continue operation with the subcomponents disabled (i.e., turned off), have the intake bot returned (i.e., eliminated and captured outside of the host) for additional testing and/or repair, or have the bot terminated or destroyed. If on the other hand, the QA abnormality in question includes suspected faulty data collection, the QA bot can perform independent testing instituted by the program, which is analogous to that of the dysfunctional bot, for the purpose of determining data accuracy. In select cases, calibration and/or modification of the bot subcomponents may be the only required intervention recommended and/or instituted by the program, which a dedicated QA/QC bot may be able to perform in-vivo. Alternatively, the dysfunctional bot may be electronically labelled by the program, excreted, and subsequently captured outside of the host. Once the calibration/modification is complete, the bot may be recommissioned for future use.

The present invention provides an important method for continuous monitoring of individual bot performance as well as its subcomponents. This ensures that the derived data and real-time longitudinal analytics by the program are accurate and representative of the host medicinal state. At the same time, ongoing bot QA and QC by the program provides a method in which bots can be continuously repaired and modified to ensure high levels of functional performance. This is further enhanced by the unique invention application which allows identification of individual bots, correlation with bot architecture, and real-time anatomic location tracking.

Exemplary Methods of Operation

A. In-Vivo Stem Cell Identification, Induction, Harvesting, and Delivery

Stem cells are unspecialized cells capable of regeneration and proliferation through cell division which can be induced to become tissue or organ specific (i.e., pluripotent). There are two primary types of stem cells: embryonic stem cells and adult (somatic) stem cells. While embryonic stem cells are harvested from fetal tissue, adult stem cells reside in the adult body and therefore provide a potential source of host-specific cellular regeneration (which in theory would be less apt to rejection).

Adult stem cells have been identified in a variety of organs and tissues including the brain, bone marrow, peripheral blood, skeletal muscle, heart, skin, teeth, gastrointestinal tract, liver, ovary, and testis. These adult stem cells are thought to reside in a specific area of each tissue (i.e., stem cell niche), which serves as a potential in-vivo source for medical use. Adult stem cells routinely reside in a quiescent state for long periods of time until they become activated by a stressor (e.g., trauma, disease). The process in which unspecialized stem cells give rise to specialized cells is termed differentiation. Both internal and external signals drive differentiation, with internal signals controlled by genes and external signals facilitated by chemical secretion and molecules in the microenvironment.

Adult stem cells can be identified through a wide array of molecular surface markers, which constitute genes and their protein products. While hundreds of these markers have been identified to date (with the list continuing to expand), a few examples include glycoprotein 1B, HAS2gene expression, iron oxide nanoparticles, interleukin-3 receptor alpha chain, neurofilament microtubule-associated protein, and Sca-1.

The identification of adult stem cell molecular surface markers, genes controlling differentiation, and micro-environmental chemicals, all present potential opportunities for in-vivo stem cell detection and activation by the present invention. In one embodiment, multi-functional bots provide the capability of identifying these molecular, genetic, and chemical markers through embedded miniaturized biosensors along with precise anatomic localization of the stem cells. Once verified, the bots can in turn communicate anatomy-specific instructions and actively solicit additional bots for stem cell collection and harvesting.

One potential clinical application for stem cell therapy which has the potential for profound improvement in patient outcomes is cardiac disease, which is a major worldwide cause of morbidity and mortality. Despite advances in cardiac revascularization (e.g., bypass surgery, coronary artery stents) and pharmacotherapy, no treatment to date can reverse myocardial cell death other than cardiac transplant which is limited in availability, extremely expensive, and associated with high morbidity/mortality rates. As a result, patients suffering from severe cardiac cell injury and/or dysfunction (e.g., myocardial infarction (MI), cardiomyopathy), often go onto to develop cardiac failure and eventual death.

Transplantation of pluripotent stem cells or multipotent myocardial progenitor cells directly into the site of damaged myocardium offers the potential to regenerate new functioning myocardium and vascularity, thereby improving cardiac function. To date, these techniques are largely restricted to in vitro testing and preclinical applications. The present invention, however, provides a methodology for in-vivo transplantation of stem and/or progenitor cells, with a number of additional clinical benefits, applications, and deliverables which will be described in the following use case.

In addition to embryonic and adult stem cells, a third option for cardiac cellular regeneration exists in the form of endogenous cardiac progenitor cells (CPCs). CPCs are a heterogeneous group of cells distributed throughout the heart (e.g., atria, ventricles, pericardium), which under normal physiologic conditions are quiescent. After myocardial injury (e.g., MI), CPCs may be activated and undergo differentiation into new myocytes or vascular cells. A number of CPC populations have been reported in the heart including (but not limited to) c-Kit +, cardiospheres, cardiosphere-derived cells (CDCs), epicardium derived cells, cardiac side population cells, stem cell antigen-1 (Sca-1), platelet derived growth factor receptor alpha.

The mechanisms for cardiac repair following stem cell or progenitor cell transplantation are thought to be multifactorial, with both direct and indirect mechanisms at play. The repair mechanisms include (but are not limited to) differentiation into myocytes and vascular cells, secretion of paracrine factors inducing hyperplasia and proliferation of existing myocytes, induction of cellular fusion between transplanted cells and existing myocytes, enhanced neovascularization, and remodeling of scar tissue (which enhances myocardial contractility and function).

This multifactorial nature of cardiac repair is specifically important and relevant to the present invention for the specialized bots described herein play a number of different diagnostic and therapeutic roles in real-time disease diagnosis and quantification, anatomic localization, identification and characterization of endogenous stem and progenitor cells, in-vivo collection and harvesting of these stem/progenitor cells, targeted in-vivo cell delivery to the specific anatomic location of injury/disease, monitoring of cellular and organ physiology and function, identification of neovascularity, and correlation with other clinical and medical device derived data.

1. Diagnosis

In the exemplary embodiment, a patient with underlying ischemic heart disease, diabetes, and hypertension experiences an acute change in clinical status characterized by new onset of shortness of breath and blood pressure lability. Review of the patient's vital signs and preliminary lab work reveal an unexpectedly high blood glucose level of 257 (normally in the 110-120 range), unexpected drop in blood pressure at 90/56 mm Hg (normally around 130/70), increased heart rate from a baseline of 88 to 114, normal temperature of 98.6 degrees, and increased respiratory rate of 22 breaths per minute (normally 12-14). Based upon these changes in physiologic parameters, an unexplained pathologic stressor is favored over a pharmacologic etiology (e.g., change in insulin or other diabetic medication). Circulating bots offers unique in-vivo diagnostic capabilities, which allow for a variety of organ specific and systemic bioassays to be performed, which can simultaneously be anatomically localized. If for example, an abnormal bioassay measurement is detected, it can be localized to the specific anatomic site of origin, which cannot be performed through conventional systemic blood assays.

During the course of these real-time in-vivo bioassays, it is determined that the patient experienced a myocardial infarction (MI) based upon a variety of cardiac biomarkers and genetic markers (e.g., cardiac troponin [cTN], creatine kinase myocardial band [CK-MB], cardiac myosin binding protein C, platelet mRNA, thromboxane A2, nucleotide polymorphisms, CTA 4 hydrolase). Note that in addition to being instrumental in establishing early and accurate diagnosis of cardiac injury, these biomarkers also provide the ability to monitor response to therapy, which is another unique application of the present invention. In some circumstances, these biomarkers may be elevated on the basis of underlying disease (e.g., renal failure), which can be clarified on the basis of longitudinal measurements, which is readily performed through continuous bot derived measurements taken by the program.

Another important diagnostic advantage of bot derived biomarker data is the ability to localize the specific site of pathology in exquisite anatomic detail. With conventional measurements which are obtained through systemic blood assays, bot derived bioassays provide the ability to localize the specific anatomic location at which the bioassay data was recorded, while correlating bioassay measurements from thousands (or even millions) of neighboring bots sequentially, thereby creating the ability to localize myocardial injury at both cellular and tissue levels. These anatomic-specific bioassay data can in turn be correlated by the program with external macro-data (e.g., EKG, echocardiography), which provides additional clinical data related to overall cardiac function. The ability of the program to sequentially analyze these micro-assays over time and over a variety of anatomic locations provides the ability of the program to create detailed pathologic-anatomic maps, which simultaneously can identify the specific anatomic location, disease state, severity, and temporal change. Unlike traditional diagnostic tests which provide a more general and macroscopic perspective on disease progression and location, bot derived data of the program of the present invention, provides a granular and microscopic analysis on disease. This takes on heightened clinical importance in disease states associated with high degrees of morbidity/mortality (e.g., cardiac MI), and which require time sensitive and customized intervention.

In one embodiment, in addition to bioassay data, circulating bots may also derive additional clinical data, which can be used by the program and/or clinician for important diagnoses, functional assessments, and determination of optimal therapies. Examples of bot derived data of importance in the setting of MI include (but are not limited to) assessment of cardiac contractility and wall motion (through ultrasound), determination and measurement of coronary vascular obstruction, characterization of atherosclerotic plaque, identification of thrombosis and anti-thrombosis pathways, and platelet aggregation. As the myriad of real-time and sequential bot derived data is collected and analyzed by the program, the program can determine an accurate assessment of disease, severity, anatomic location, disease progression, structural integrity and functionality, and physiologic response. This enhanced in-vivo diagnostic capabilities provides for more accurate and definitive treatment, with the added capability of monitoring treatment response on a cellular level.

2. Treatment Planning

In one embodiment, once the diagnosis, severity, and progression of disease is determined by the program through objective data, the next step is to review treatment options in order to determine the most efficacious form of therapy specific to the patient and clinical circumstances. While traditional treatment of MI includes pharmacologic and revascularization techniques, in one embodiment, stem cell transplantation offers a new and potentially breakthrough strategy, aimed at revitalization of cardiac tissue at the site of injury/necrosis.

As previously discussed, a number of transplantation options exist in the forms of embryonic stem cells, adult stem cells, and endogenous cardiac progenitor cells (CPCs). Identification and anatomic localization of adult stem cells and CPCs can be performed by the program through the identification of molecular surface markers, genes controlling differentiation, and microenvironmental chemicals. In one embodiment, multi-functional bots provide the capability of identifying and anatomically localizing these molecular, genetic, and chemical markers through embedded miniaturized biosensors. Once identified, additional biochemical and genetic analysis can be performed by the program on stem and progenitor cells to ascertain their cell type of origin, concentration, degree of differentiation, and mitotic potential. Ideally, these stem and progenitor cells are clustered together into stem cell niches, which provide the ability to harvest stem and progenitor cells in large numbers.

In one embodiment, a unique application of the present invention is the creation by the program of host-specific stem cell and progenitor cell maps (which will be subsequently referred to as "stem cell maps") which provide a 3-dimensional anatomic display of stem/progenitor cell location, concentration, differentiation potential, and biologic activity. These baseline anatomic maps of stem cell/progenitor cell location provide an authorized end-user with a reference guide of location and functionality of adult stem and progenitor cells in the event that an autologous (i.e., intra-host) transplantation is required. Since stem and progenitor cell populations and locations can change over time they are periodically updated by the program, the frequency of which is commensurate with the underlying host's clinical status and potential need for future intervention. If for example the host is a 35 year-old male in excellent health and no active medical problems, then a stem cell and progenitor cell map may only be performed by the program on a bi-annual basis. If, however the patient is diagnosed with a new malignancy with a high potential for stem cell transplantation (e.g., lymphoma, leukemia), the frequency of such mapping may be increased by the program to every four months in order to provide an updated reference in the event that an acute crisis was to occur requiring immediate transplantation. While exogenous fetal stem cell transplantation also remains a viable option, this might be determined to be less viable given the external stem cell source (which could potentiate a graft versus host response), lack of availability, and/or religious objections on the part of the host patient.

In one embodiment, an example of a stem/progenitor cell anatomic map prepared by the program, shows the anatomic location and relative concentration of stem/progenitor cells, along with a crude measure of differentiation potential. While the science of quantifying differentiation potential is evolving, there are a few relevant examples of how markers in stem and progenitor cells can be used to determine differentiation potential and cell potency, along with a variety of methods to stimulate cell proliferation. A few examples include expression level of the gene encoding chromodomain helicase DNA binding protein 7 (CHD7) and identification of transcription factors responsible for epigenetic cell programming (e.g., OCT4, SOX 2, NANOG). As new and improved in-vivo methods for identifying and characterizing differentiation potential and cell potency are discovered, these can be incorporated by the program into the diagnostic arsenal of the invention, in a manner similar to identification and measurement of other bioassays and biomarkers.

In one embodiment, in the reference stem cell map, an anatomic 2 or 3-D display is provided by the program, which identifies the different anatomic locations of adult stem and progenitor cells, the concentration of these cells, the corresponding cell of origin, and a measure of differentiation potential. If desired, these cells can be periodically sampled and subjected to in vitro testing to provide additional data related to functionality. During routine or heightened surveillance (the latter of which would be based on changes in clinical status), the stem cell map is updated by the program in accordance with the new data collected. In addition to the new map displaying this updated information on the display 123, a temporal change map can be derived by the program, which illustrates changes in stem and/or progenitor cell populations over time. These temporal change maps can be extremely valuable in population health assessment and analysis, for they show expected changes in stem and progenitor cell pollutions over time for both the general population, as well as subgroups, which can be sorted on the basis of specific clinical and/or demographic attributes. As an example, one subgroup may include all patients with a longstanding diagnosis of poorly controlled diabetes, another group includes all lymphoma patients in remission, one subgroup includes patients who are dietary vegans, and another subgroup includes Hispanic females over the age of 55.

In one embodiment, an additional optional component of the stem cell map may incorporate additional in-depth functional data which goes beyond simple surveillance. Suppose for example a sample of adult stem cells were collected from a specific bone marrow location (e.g., proximal left femur), with the goal of providing more detailed analysis of differentiation potential and cell potency. In current practice this type of testing would be performed in vitro, and would therefore require extraction of the cells to be tested, which could be readily performed by bots containing cellular collection capabilities. Once the targeted cell specimens are collected, the corresponding bots are retrieved, and the cellular specimens are subjected to in vitro testing, with the specific anatomic location and cell source recorded by the program to ensure that each individual cell specimen has its own associated data. This in-vitro testing may include a number of parameters which may not be available through routine bot surveillance including (but not limited to) metabolic activity, measures of mitosis, vascularity, genetic expression, DNA/RNA analysis, and more detailed internal and external cell markers. This additional in-depth testing takes on heightened importance in the event that an actual transplantation becomes necessary and extensive pre-procedural testing and analysis is required.

In one embodiment, in addition to identifying and quantifying the anatomic locations of stem and/or progenitor cells, the stem cell maps can also incorporate clinical data into the anatomic and organ specific map. This provides an overview and reference of pertinent clinical data including (but not limited to) active and/or previous disease processes, surgery (or other types of medical intervention), medical devices, medications, "at risk" anatomic regions and/or organ systems, and genetic disease markers. This reference clinical data provides an anatomic and organ system overview as to the host's current and prior medical history which may be of relevance to stem/progenitor cell harvesting, collection, and/or transplantation.

In the example cited where a patient has experienced an acute MI, the anatomic/organ system clinical overlay provides valuable clinical data which may be directly relevant to the patient's cardiac status, prior interventional procedures, medications, and comorbidities. If for example, the patient's cardiac history is significant for prior placement of a right coronary artery stent, in-dwelling pacemaker, beta-blockers and antihypertensive medications, and prior arrhythmia, these factors may become relevant in the event that stem cell transplantation is actively considered for treatment of the MI and diseased myocardium. Suppose for example a localized niche of cardiac progenitor cells is identified in the right ventricle, which in theory may serve as an excellent source for transplantation. Knowing that this region is supplied by the right coronary artery branch in which the stent is located places this anatomic location at "high risk" as a potential stem cell/progenitor donor site. Additional vascular and metabolic testing would therefore be required to assess myocardial function and blood flow in the region of anatomic region of interest, as well as pharmacologic assessment of whether current beta-blockers and/or antihypertensive medications would need to be adjusted prior to performing stem/progenitor cell collection. In the event that this clinical data was to reduce or eliminate the right ventricle as a potential donor site, alternative anatomic sites would have to be identified by the program in order to safeguard the patient's cardiac status and anatomic limitations.

2. Detailed Assessment of Recipient Site

In one exemplary embodiment, once the diagnosis has been established and potential donor sites have been identified, the next step is a detailed assessment of the anatomic recipient site. This entails accurately assessing the anatomic location and severity of pathologic involvement, associated biochemical abnormalities, and functional disturbances. In the setting of an acute MI, it is important to identify the specific location and volume of affected myocardium, while distinguishing between dead (i.e., necrotic), ischemic, and "at risk" tissue. This delineation is particularly important for prognostication and determination of optimal therapy (e.g., pharmacologic, revascularization, stem cell transplantation).

Traditional techniques (e.g., cardiac CT, MRI nuclear medicine, Echocardiography) used to determine the location and severity of myocardial injury are "macroscopic" in nature and provide assessment on a tissue level, while the present invention offers the potential to provide analysis on a microscopic and cellular level, which may be far more valuable and accurate in determining biochemical, functional, and electrical injury, as well as differentiation between reversible and irreversible myocardial insult.

Unlike traditional imaging techniques which evaluate cardiac perfusion and wall motion on a global level, the circulating bots of the present invention can provide a number of quantitative and functional measurements on a local or even cellular level. Bots can be directed to the specific site of infarction and cell injury through a variety of methods including (but not limited to) real-time analysis of cardiac biomarkers, cellular chemotaxis (i.e., macrophages and fibroblasts typically migrate to the site of injury), identification of vascular stenosis and/or occlusion, and correlation with external data sources (e.g., Echocardiography, Cardiac CT). Once the anatomic region of interest has been identified, a number of different bot derived actions can take place which provide in-depth and objective analysis of local cardiac anatomy, ischemic/necrosis, quantitative assessment of blood flow, metabolism, biochemistry, electrical conductivity, and myocardial function (i.e., contractility).

In one embodiment, in addition to providing real-time and longitudinal diagnostic data collection, bots can also perform other functions including (but not limited to) cell/tissue collection, local release/injection of pharmacologic agents, deployment of anatomic markers (for future bot navigation and aggregation), revascularization, and microsurgery. The derived real-time data can then be used by the program to create a 3-D anatomic map of the heart providing a detailed anatomic and functional assessment of the local area of pathology with visual highlights showing "at risk" myocardium and real-time changes in biochemistry and function. This ability to provide continuous qualitative and quantitative assessment of myocardial viability provides an in depth and objective methodology for updated diagnosis and prognostication, which frequently change during the acute and subacute phases of MI.

3. Treatment Planning and Intervention Options

Traditional pharmacologic and revascularization treatment strategies are primarily aimed at preventing extension of myocardial necrosis and not aimed at reversing existing myocardial cell death. Stem cell and/or progenitor cell transplantation on the other hand offers the potential to regenerate viable myocardial cells at the site of infarction and as a result improve cardiac function at or near its pre-infarction state. This is especially appealing in clinical situations where large volume of myocardium has been irreversibly injured and/or the damaged myocardium has resulted in markedly decreased cardiac function and/or conductivity which is life threatening.

In a scenario where stem/progenitor cell transplantation is deemed the optimal therapeutic action, the present invention provides a number of options and benefits which are not available through traditional techniques. Using the present invention, the specific anatomic area of interest is first delineated by "anatomic scout" bots 200 (see FIG. 2) which identify the myocardial cells 201 which have destroyed by the MI as well as surrounding myocardial cells deemed "at risk". In addition to depositing the disease-specific anatomic localizers 202 at the site of pathology, the anatomic localizers 202 also have the ability to emit a unique radiofrequency signal which serves as a beacon to help guide authorized bots 200 to the anatomic site of interest for further action. In this case, the primary action to be taken consists of targeted injection of stem/progenitor cells in the region of infarcted myocardium.

In one embodiment, additional actions may be indicated in accordance with the specific clinical context and status of the underlying myocardium. As an example, other therapeutic options in addition to stem cell transplantation may be deemed advantageous to MI therapy, which can be directed through targeted bot action. Two primary categories of alternative targeted intervention include localized pharmacologic intervention and structural intervention. Examples of pharmacologic intervention include (but are not limited to) antiplatelet therapy, thrombolytics, B-adrenoreceptor blockers, vasodilators, calcium channel and beta blockers, and angiotensin inhibiters. Unlike traditional pharmacologic therapy where these agents are administered systemically (and have associated side effects), targeted bot delivered therapy provides for local injection at the specific site of pathology, which allows for higher local dose to be delivered along with diminished systemic side effects.

In one embodiment, another category of bot intervention is structural or mechanical in nature, in which specialized bots can be used for local therapeutic intervention by acting directly on infarcted and/or at risk myocardium. Examples of such intervention may include (but are not limited to) angioplasty, atherectomy, radiofrequency ablation, stent placement, and transmyocardial revascularization using lasers. The net result is that bots can be specifically directed to the anatomic region and pathology of interest to effect local therapeutic action which can come in a variety of forms including stem cell transplantation, pharmacologic delivery, or mechanical intervention. The methods used for intervention can be customized in accordance with the individual patient, underlying anatomy, and clinical context. The goal is to minimize the extent of invasiveness (and thereby reduce morbidity and post-operative complications) while delivering the therapeutic action directly at the site of pathology, at both tissue and cellular levels.

4. Stem Cell and Progenitor Cell Harvesting

In one embodiment, the next step in the process of stem/progenitor cell transplantation is the targeted harvesting of stem/progenitor cells, based upon availability, location, potency, and clinical efficacy (relative to the specific state of pathology).

In the event that the host has a pre-existing stem cell map, this can serve as a valuable resource and starting point for targeted stem/progenitor cell harvesting. If this is not readily available then the harvesting must be done from scratch, which entails having large numbers of circulating surveillance bots identify potential stem/progenitor cell candidates and depositing anatomic markers for future reference and analysis. Ideally, stem cell niches would be identified which represent large numbers of localized stem/progenitor cells, which thereby reduce the time and effort identifying and harvesting prospective candidates for subsequent transplantation.

In one embodiment, once potential donor sites are identified (through pre-existing stem cell maps and/or new surveillance), the potential stem and/or progenitor cells must be tested to determine viability (relative to the specific clinical context), potency, and differentiation potential. This testing may be performed in-vivo through bot derived identification of molecular surface markers, genes controlling differentiation, and microenvironmental chemicals.

Alternatively, in one embodiment, this testing may be performed in vitro, which would necessitate and additional step of bot cell collection, transport, and retrieval. In either scenario, the stem and/or progenitor cell candidates are analyzed by the program for the purpose of determining the optimal candidates relative to the clinical context. In the event that an endogenous (i.e., host-derived) source cannot be identified, transplantation of exogenous embryonic stem cells would be considered.

In one embodiment, the process of in-vivo harvesting of stem/progenitor cells entails directing specialized cell collection bots to the specific anatomic sites of qualified stem/progenitor cells, which often have had anatomic localizers placed for reference. Once appropriately validated by the program, cell collection is performed by bots armed with specialized aspiration devices and storage reservoirs. In situations where large numbers of cells are being collected and/or the internal storage reservoirs contain insufficient capacity, the aspirated cells may be transferred to storage bots, which are specifically designed with the capacity to hold larger volumes of cells, tissue, and/or fluid.

In the present invention, there are two options for transporting the acquired stem/progenitor cells to the anatomic site/s requiring transplantation. In one embodiment, in the first option, the bots containing the newly collected stem cell specimens undergo elimination and once retrieved have their stem/progenitor cell specimens transferred to specialized bots tasked with transplantation. In one embodiment, in the second option, the bots containing the stem/progenitor cell specimens are redirected to the specific anatomic site of transplantation. In this scenario, these bots are not eliminated from the host, thereby allowing the process of stem cell transplantation to directly proceed, which offers the theoretical advantages of time saving and reducing potential loss of the stem/progenitor cell specimens.

5. Transplantation

In the present invention, there are three separate steps involved in stem/progenitor cell transplantation. In one embodiment, in the first step, bots must navigate to the specific anatomic area of clinical concern. In one embodiment, in the second step, bots transporting the stem/progenitor cells must perform the process of transplantation at the desired anatomic site. In one embodiment, in the third step, additional preparatory steps may be taken which serve to improve the overall success of the transplantation procedure and cell regeneration. While not a direct step of the transplantation process, per se, continuous data collection (e.g., biomarkers) is performed by the program pre- and post-transplantation, which serves as an important objective measure of analyzing the relative success or failure of the transplantation process.

In one embodiment, the first step of anatomic localization at the specific anatomic site of transplantation is important to overall success since it is imperative that the delivery of stem/progenitor cells occur at the specific site of clinical concern, which in this example, includes an infarcted myocardium. In one embodiment, once the bots containing the stem/progenitor cell specimens reach the desired anatomic site of transplantation, they coordinate localization with one another based upon the number of participating bots, requisite anatomic coverage volume, and predefined transplantation stem cell concentration. This latter variable refers to the fact that stem/progenitor cell transplantation is not necessarily uniformly distributed but instead may be heterogeneous in nature, depending upon anatomy, functionality, and distribution/severity of disease.

As an example, suppose that in the case of MI, an important area responsible for electrical conductivity of a major nodal pathway has been damaged and as a result the patient is experiencing a life-threatening arrhythmia (e.g., ventricular tachycardia). In an attempt to revitalize myocardial cells in this region and return the heart to normal electrical conductivity and rhythm, a larger concentration of stem cells is designated for the specific anatomic location corresponding to the electrical pathway. The net effect is that the anatomic designation of disease and its differential area of involvement leads to the creation of a disease map which serves as a 4-D graphical representation of anatomy (on both macroscopic and microscopic levels), pathology, differential disease severity, and associated clinical markers (e.g., bioassays, cellular distribution). This provides an important objective reference which can serve to guide diagnosis, treatment planning, and assessment of clinical response. Since this disease map is dynamic in nature, it will often require periodic updating to reflect changes in disease location, severity, and response to intervention.

In this example, the representative disease map is created by the program in accordance with a variety of macroscopic and microscopic clinical data sources including (but not limited to) functional cardiac tests (e.g., Echocardiography, EKG), laboratory tests (e.g., troponin, cardiac enzymes), imaging studies (e.g., cardiac CT, nuclear medicine SPECT), bioassays, prior interventional procedures (e.g., CABG, coronary stent placement) and molecular markers. The combination of this data by the program can in turn lead to the creation of the cardiac disease map which provides a 3-D graphical display of the heart in its entirety along with any focal areas of pathology (which can be represented by individual disease states and temporal change). When intervention is performed on a molecular level (as in the case of bots directed stem cell transplantation), the disease map is presented by the program in both macroscopic and microscopic display presentation states, in order to accurately depict anatomy, function, and disease on a cellular level.

In one embodiment, the disease map is particularly important given the unpredictable nature of disease in terms of anatomic distribution and progression. In many disease states, the distribution of disease is non-linear and often follows a distribution which is multi-centric or multifocal. While traditional medical imaging studies (e.g., MRI CT) show disease in its macroscopic form, they often do not adequately display the non-linear pathway and insidious disease process may follow, nor do they show disease at the molecular level. As a result, these traditional imaging exams underestimate the full extent of disease in its anatomic distribution, while also failing to address the pathophysiology of disease. In the example cited of a recent MI, conventional imaging exams (e.g., cardiac MRI, Echocardiography, nuclear medicine) will show the global extent of infarction but fail to determine myocardial functionality at the cellular level. At the same time, if myocardial necrosis and/or ischemia follows a non-linear pathway, these macroscopic imaging studies will show the epicenter of disease and immediately surrounding tissue but often fail to visualize small non-linear extensions of disease.

In one embodiment, the additional ability of the disease map to record disease progression (or regression) in real-time and at the molecular level is another important attribute of the program of the present invention. The same manner in which program can track, record and analyze real-time longitudinal data on the basis of bioassays, molecular markers, and cell distribution, can be directly applied to the disease map. This provides authorized healthcare providers with up to the date quantitative and qualitative analyses and 4-D visual displays of the continuum of disease, which cannot be readily provided by conventional imaging and/or laboratory exams. This ability of the program to graphically display and objectively analyze disease change is applicable to a myriad of pathologies (e.g., cancer, infarction, infection) and takes on heightened importance in the instances of rapid and life-threatening disease states (e.g., sepsis, bleeding). In the example of bleeding, continuous data tracking can not only demonstrate the progression and location of overall disease but the program can also provide vital data related to anatomy (e.g., specific locations of active bleeding), quantification of disease (e.g., bleeding rate and volume), and physiology (e.g., changes in blood pressure, heart rate, vasoconstriction). The combination of time stamped objective data and anatomic visualization by the program is achievable through the disease map and can also be recorded in a referenceable database 125 to provide clinical correlation and analysis of other patients with similar disease profiles.

In one embodiment, once the disease map has been created by the program, authorized providers can utilize this information to determine treatment options in accordance with the patient baseline clinical status, surgical history, pharmacologic regimen, comorbidities, genetic predisposition, disease severity, and anatomic area of disease involvement. Based on this analysis by the program, the best course of action in this example case is stem/progenitor cell transplantation, which can be customized to the specific anatomy of concern and disease extent. Using the 4-D disease map, a transplantation strategy can be devised by the clinician, with assistance from the program, which takes into account the anatomic distribution of disease (at both macroscopic and molecular levels), disease severity, and functionality (e.g., electrical pathways, myocardial contractility). In this example, the authorized cardiologist may utilize the visual and functional properties of the disease map to outline the number, distribution, and requisite functionality of stem/progenitor cells to be transplanted as they specifically relate to the individual patient's cardiac anatomy, disease, and physiology (i.e., customized therapeutic intervention). Since certain areas of myocardium (e.g., electrical pathway) may be deemed to be of higher clinical priority, this anatomic location may be selected to have "high potency" stem cells transplanted, in an attempt to optimize clinical outcome in the anatomic area of greatest clinical priority. Other anatomic regions (e.g., on the periphery of the infarct) may be deemed to be of lower clinical priority and as a result utilize progenitor cells of lower potency for transplantation. The goal is to match stem/progenitor cell functionality with anatomy in accordance with clinical priority, in an attempt to optimize clinical outcomes.

In one embodiment, once the disease map and intervention strategy has been established, the next step is directing the deployment of bots for the purpose of targeted stem/progenitor cell harvesting, delivery, and transplantation. Using the stem/cell map, the authorized end-user can select the specific donor sites and requisite number of stem cells to be harvested while taking into account the proliferation potential and potency of these donor cells. Each individual stem/progenitor cell is assigned by the program to a specific "harvesting bot", which is then assigned a specific anatomic location for delivery (i.e., transplantation). This provides a mechanism for targeted stem cell harvesting, individual bot assignment, and targeted delivery to a specific disease location. At each individual step in the process, a communication signal is sent by the program between the bot and authorized end-user to ensure that the step was satisfactorily completed at the correct anatomic site. In the event that a mistake is made (e.g., wrong stem location of harvesting), the bot may be directed by the program and/or clinician, to terminate further action, redirect the anatomic site of transplantation, or discard the transplanted stem cell and retrieve the specific stem cell of interest. Once the required action has been successfully completed and verified, the next step is directed to occur. Since stem/progenitor cell transplantation may require the coordinated action of thousands of bots, this process of individual step confirmation achieves the desired goal at the specific anatomic locations of interest.

In one embodiment, once stem/progenitor cell delivery has been completed, an additional "priming" step may take place, which is when a specific bot directed action takes place in an effort to improve transplantation effectiveness. Examples of "priming" strategies include (but are not limited to) pharmacologic manipulation (e.g., ATP channel openers, growth factor), conjugation with biomolecules, molecular modification (e.g., overexpression of anti-apoptotic oncogenes), hypoxia, and radiation. In one embodiment, these actions can be performed by a separate set of bots which arrive at the designated anatomic locations shortly after transplantation and perform their designated function (e.g., release of growth factor) in a regional fashion, so as to perform the "priming" action on numerous transplanted calls in a single coordinated action. The selection of the optimal priming strategy can be determined by the program in accordance with the anatomic location, disease state, origin and type of stem/progenitor transplant cells, and patient clinical profile.

In one embodiment, once the transplantation process (with or without an additional priming step) is complete, the next step is disease surveillance and monitoring. This provides an objective data-driven analysis for assessment of disease change pre and post stem cell transplantation along with the need for additional and/or alternative intervention. In the case described where stem/progenitor cells have been transplanted following myocardial infarction, real-time bot derived data can provide a variety of analyses relating to myocardial function (e.g., contractility), electrical activity (e.g., cardiac rate and rhythm), physiology (e.g., blood oxygenation), and myocardial cell viability (e.g., cytokines). These data-derived myocardial metrics can in turn be correlated by the program directly with cardiac anatomy to determine data differential between "normal" myocardium (i.e., unaffected by MI) and "diseased" myocardium (i.e., MI affected). In addition, analysis by the program of comparable measurements in the affected anatomic area which can be obtained before and after stem/progenitor cell transplantation, provides valuable information relating to transplant effectiveness and the need for additional and/or alternative treatment (e.g., pharmacologic, supplemental stem cell transplantation).

As new time stamped data is collected, new disease maps can be created by the program, which provide visual representation of disease, anatomy, and treatment. The corresponding data is simultaneously recorded in a referenceable database 125 by the program for further analysis and guidance for future best practice guidelines.

Information Required for Bot Derived Stem/Progenitor Cell Transplantation

A. Stem Cell Map
  1. Organ specific (chronologic)
  2. Cellular concentration
  3. Classification of stem cell type
B. Stem Cell Activity
  1. Biologic activity (over time): metabolic, vascularity, mitosis
  2. Type and level of stem cell markers (intra and extracellular)
  3. Differentiation potential
C. Disease
  1. Organ/tissue specific
  2. Disease severity
  3. At risk vs. disease
  4. Metabolic/pathologic markers
D. Stem Cell Implantation Response
  1. Pre and Post Disease Markers
  2. Metabolic Activity
  3. Mitosis
  4. Tissue/Organ Physiology
E. Patient Profile
  1. Genetic Markers
  2. Disease State
  3. Co-Morbidities
  4. Pharmacologic
  5. Demographics
  6. Prior Medical Interventions
  7. Response to Treatment Applications In one embodiment, the combined data collected, stored, and analyzed by the program from a single source, provides a real-time and longitudinal 4-D in-vivo record of the individual patient, which can be directly communicated by the program with the conventional electronic patient record (which combines data from other external data sources).

In one embodiment, in addition to diagnostic mode (where bots are tasked with real-time data collection for diagnostic purposes), bots can also act in therapeutic mode (where bots are tasked with performing a variety of therapeutic interventions. Examples of therapeutic actions include (but are not limited to) drug delivery, stem cell implantation, surgery, radiation, cryotherapy, thermal ablation, electromagnetic pulse, and vascular occlusion (e.g., ligation, deployment of occlusive device (e.g., embolization coils), or release of chemical substance (e.g., glue). Note that bots may have multifunctional capabilities, allowing them to switch from diagnostic to therapeutic modes of operation.

1. Targeted stem cell delivery is another important and unique therapeutic application of the present invention. The ability to perform extremely localized anatomy-specific diagnosis and therapeutic intervention on a molecular level provides a unique ability for earlier and more definitive diagnosis and treatment. If, for example, myocardial infarction localized to the inferior right ventricular wall is detected, a variety of localized therapeutic interventions can be attempted and prospectively monitored to assess treatment response. In this example, in addition to assaying biochemical markers for myocardial cell death (e.g., troponins, creatine kinase, monoclonal anti-creatine kinase antibodies), bots of the present invention can also monitor local myocardial electrical activity in the anatomic region of interest for a combined assessment of cell death and electrical conductivity by the program. In the event that the clinical response to conventional medical therapy was poor, an alternative approach such as localized implantation of stem cells could be performed by nanobots with a series of stem cell implantations at multiple targeted anatomic sites (including both the surface and centrally located components of the affected myocardium). Once completed, nanobots can in turn be used for continuous assessment of treatment response and return of myocardial function (e.g., chemical markers, electrical conductivity, wall motion, contractivity).

2. In one embodiment, another unique feature of the nanobots includes in-vivo stem cell harvesting, where nanobots can be used in selected hosts to retrieve organ and anatomy specific stem cells, which to date require prolonged time (e.g., peripheral blood sampling), painful procedures (e.g., bone marrow sampling), or politically controversial techniques (e.g. umbilical cord sampling).

3. While a myriad of unique clinical applications exist using the present invention with nanobots embedded with multifunctional miniaturized biosensors, wireless transmission, and self-propelled capabilities a few pertinent examples include the following:
   A. Diagnosis and therapeutic interventions for organ rejection (following transplant)
   B. Real-time localization, intervention, and remote monitoring of active bleeding source in acute trauma (e.g., battlefield injury)
   C. Surveillance of environmental exposure in bioterrorism (e.g., XRT, nerve gas, bacterial toxin) or epidemic, with capabilities for population screening, real-time environmental tracking of agent (e.g., wind, water propagation), source localization, disease surveillance, and quarantine strategic planning.
   D. In utero diagnosis and treatment of maternally transmitted infection or congenital defect.

4. In one embodiment, in addition to intra-body applications, the same nanobots with embedded sensors can also be used externally to the body for detection, genetic mapping, localization, sampling, and temporal concentration change of environmental agents (e.g., viral, bacterial, XRT, toxins). In addition, clusters of therapeutic nanobots can be used for containment and therapeutic intervention.

5. In one embodiment, a variety of options exist for nanobot communication including (but not limited to) Wi-Fi, WiMax, Bluetooth, Airdrop, ambient backscatter, high frequency audio, ultrasound tracking, ZigBee, wireless router, microwave, infrared, vibrations, and near field communication (NFC).

6. In one embodiment, nanobot positioning can be fixed or mobile in accordance with the application (i.e., task being performed), anatomic location (i.e., milieu), and functionality. In mobile operation, the nanobot can travel via both passive and active modes. Passive mode utilizes intrinsic flow in the local environment (e.g., blood flow in vessels, gastrointestinal peristalsis, airflow in lungs) versus active mode which utilizes an energy source (e.g., battery, kinetic harvester, thermal gradient, fuel cells, infrared radiation, low frequency magnetic fields, inductive links).

7. In one embodiment, when fixed positioning of a nanobot is required a number of options are available including (but not limited to) release of a chemical adhesive to physically secure the nanobot to an adjacent anatomic surface, deployment of a mechanical structure contained within the nanobot (e.g., strut, prong) which physically anchors the nanobot to local anatomy, or deployment of a semipermeable balloon which provides stationary positioning of the nanobot within an anatomic structure (e.g., blood vessel, bronchus) without impeding normal flow. When a physical structure or barrier is utilized, this can be manually removed once the nanobot task is completed. When an externally secreted substance (e.g., bio-adhesive) is utilized, the nanobot can disengage from the agent by either local removal of the substance (e.g., physical removal using scrubbers or brushes) or release of a chemical that dissolves the bio-adhesive. A third option is for physical retrieval of the nanobot by another nanobot (e.g., magnetic attachment).

8. In other embodiments, in addition to conventional communication strategies using wireless technologies, nanobot communication and physical control can also be exerted using gaming technologies, which effectively allow an authorized end-user to selectively control individual or groups of nanobots for the performance of individual tasks. This external control and navigation is particularly relevant when complicated therapeutic interventions are performed (based upon the specific type of task, technology being deployed, or anatomic structure). If for example microsurgery is being performed on a cerebrovascular malformation, the clinical condition, anatomic region, and technical challenge classifies the procedure as "high risk". If the risk-benefit analysis favors human oversight and control, a specially trained operator (e.g., neurosurgeon) may elect to take control of the nanobot for task performance and can do so using specially developed game controls which provide targeted nanobot selection, anatomic localization, and deployment of specialized tools/surgical applications. Using nanobot generated real-time magnified video imagery, the operator can directly visualize the anatomy and pathology of interest as well as the performance of the procedure. In the event that an iatrogenic complication was to occur (e.g., bleeding, vascular injury), additional nanobots can be manually deployed for intervention (which can also be under the control of the operator if needed).

9. In one embodiment, data authorization and multi-tiered data access is predicated on a number of different levels including the host (e.g., individual patient of record), disease, organ system/anatomy, nanobot classification, type of biosensor and task being performed. It is entirely possible for an authorized provider to have access to one type of nanobot/biosensor without access to others within the same host. As an example, a provider (e.g., cardiologist) tasked with diagnosis and treatment of one disease (e.g., coronary artery disease) may not have authorization for data access and nanobot interaction with a different disease process (e.g., renal failure) within the same host. At the same time, a thoracic surgeon may have access to specialized nanobots with interventional capabilities (e.g., cardiac stem cell implantation) which another specialist provider (e.g., cardiologist) does not have authorization for. This compartmentalization of data authorization and access is intended to ensure that providers have restricted access only to the data and corresponding nanobots required for their specific occupational needs and education/training. In some circumstances, clinical providers may have more generalized (i.e., multi-disease/multi-organ) data access, as might be expected for a given primary care provider. However, in this circumstance, the provider may have broad base data access for diagnostic purposes, without corresponding access to certain types of therapeutic interventions. This again is intended to ensure that nanobot and biosensor functionality is selectively provided to the least number of professionals required for optimal healthcare delivery, for the combined purposes of improved data security and clinical outcomes. Since each individual nanobot has its own unique identifying data, authorization and access to its functionality and derived data can be performed on an individual or group basis.

10. In one embodiment, the nanobot and biosensor derived data may be multidimensional in nature and highly specific to individual anatomic regions within a single or multiple organ system, thereby allowing for highly targeted diagnosis and treatment, which may even extend to the molecular level. As an example, if one was interested in analyzing data related to blood flow a variety of data could be collected and analyzed through various anatomic regions within the same host including the following:
   A. Arterial/venous (AV) shunting (e.g. arteriovenous malformation)
   B. Localized hyperemia (e.g. infection)

C. Stenosis (e.g. renal artery associated with hypertension)
D. Active bleeding (e.g. trauma)
E. Neovascularization (e.g. malignancy)
F. Intramural hematoma (e.g. aortic dissection)
G. Cessation of flow (e.g. brain death and organ procurement)

11. Up until now the applications of the invention have largely focused on nanobot derived real-time diagnosis, disease surveillance, and treatment at the tissue level. Another application of the present invention is biologic analysis at the cellular or molecular level using nanotechnology (i.e., microscopic nanobots containing miniaturized biosensors). One application of the present invention is the biochemical analysis of signal transduction in which cellular surface binding proteins are assayed for the purpose of analyzing intermolecular signaling which can drive a variety of cellular functions including (but not limited to) cell attachment, shape change, migration, destruction and proliferation. Signal transduction events (e.g., change in calcium, pH) can be actively measured and monitored through immunohistochemistry using labelled antibodies. In addition to direct bioassay, these surface binding proteins can also be actively modulated through the local release of specific inhibitors (e.g., kinase and EGFR inhibitors) for the purpose of measuring response, which can in turn be used for therapeutic purposes.

12. In one embodiment, a method for in-vivo molecular analysis would be to initiate deliberate phagocytosis of the injected nanobots through either mechanical aggregation of nanobots or local release of a chemical compound. Upon phagocytosis, the nanobots would be intracellular in location, thereby providing them with the ability to perform in-vivo intracellular analysis. (Note that current molecular analysis is largely performed through in vitro analysis.)

13. In one embodiment, a unique application of the invention is to introduce artificial intelligence (e.g., machine learning, neural networks) into the nanobots, thereby providing them with the ability to "self-direct" and proactively interact with their local environment and other nanobots in accordance with the real-time data they collect. As an example, upon registering an unexpectedly elevated bioassay measurement, the program would be expected to confirm the authenticity of the data by repeating the test result, either with the same of a neighboring nanobot (i.e., data confirmation). If the measurement of interest is confirmed by the program, then the ensuing action to be taken can be derived from a variety of options including (but not limited to) the following: retrieval of comparable data from the centralized database 125 by the program, to determine what actions were previously taken under similar circumstances (i.e., database retrieval); query of predefined rules-based algorithms by the program; external direction of an authorized third party (e.g., physician specialist) by the program; or application of computerized artificial intelligence techniques by the program (e.g., within the local area network). As more patient-specific data is actively collected and analyzed over time by the program, the resulting data and derived actions are used by the program to create a patient and data-specific knowledge base which can be automatically transferred to the nanobot at the time of data collection and confirmation.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A visualization system disposed in a human body, comprising:
   a nanobot configured to be disposed within the human body, said nanobot having at least one embedded biosensor, said biosensor which operates in real-time to continuously obtain data from within the human body;
   a visualization device configured to be integrated and/or embedded within said nanobot to provide real-time visualization data in the human body;
   a transmitter/receiver disposed on said nanobot which transmits data from said nanobot to an external transmitter/receiver, said transmitted data including said data from said biosensor and said data from said visualization device; and
   a processor configured to receive said data from said external transmitter/receiver of said nanobot and analyze said visualization data to determine said anatomic localization of said nanobot at a specific anatomic position within the human body.

2. The system of claim 1, wherein said visualization device includes at least one of photography, video, endoscopy, confocal imaging, two photon imaging, intravital imaging, laser excitation, optical frequency domain imaging, optical coherence tomography, infrared imaging, or ultrasound.

3. The system of claim 1, wherein said processor comprises:
   a visualization module which analyzes said visualization data from said visualization device, with biologic and pathologic data from said biosensor, from one or more anatomic sites; and
   a mapping module configured to create four-dimensional (4D) maps;
   wherein said mapping module combines said analysis from said visualization module to yield at least one of an anatomic, visualization, functional or pathologic 4D map which is continuously monitored by said processor to detect environmental changes at cellular and tissue levels at said specific anatomic position in the human body.

4. The system of claim 3, wherein said visualization module combines said 4D map with external data from macroscopic imaging/visualization technologies to create a 4D visualization map.

5. The system of claim 4, wherein said macroscopic imaging/visualization technologies include at least one of MRI, ultrasound, intraoperative photography or intra-procedural photography.

6. The system of claim 5, wherein said visualization data from said visualization device is derived from a plurality of nanobots.

7. The system of claim 4, further comprising a display on which said 4D visualization map is displayed.

8. The system of claim 7, wherein said 4D visualization map is patient-specific and tracks disease progression or regression on said display.

9. The system of claim 8, wherein said visualization data is time-stamped.

10. The system of claim 1, further comprising:
   an anatomic localizer configured to provide data on a position of said nanobot within the human body to said external transmitter/receiver, in conjunction with said visualization device from said nanobot.

11. The system of claim 10, wherein said nanobot includes a propulsion system, and said nanobot is self-propelled to said specific anatomic position based on said analysis of said data from said visualization device.

12. The system of claim 1, wherein each said nanobot can physically attach to another nanobot by aggregation using an attachment mechanism, to complete a designated action.

13. The system of claim 10, wherein said anatomic localizer emits a tracking signal which is received by a receiving sensor on said nanobot, such that said nanobot is deployed to said anatomic localizer by a location module which directs a location of said nanobot.

14. The system of claim 13, wherein a deployment nanobot one of deposits or propels said anatomic localizers to said specific anatomic position in the human body.

15. The system of claim 14, wherein a signal emitted from said transmitter/receiver on said nanobot, signals anatomic registration between said nanobot and said anatomic localizer.

16. The system of claim 8, wherein said processor further comprises an electronic alert module which issues a real-time alert on condition that a pre-defined data threshold has been reached.

17. The system of claim 8, wherein said processor performs a trending analysis which is directly incorporated into said 4D visualization map.

18. The system of claim 8, wherein said processor provides temporal change at a variety of data points for display on said 4D visualization map.

19. A method of visualizing a human body, comprising:
disposing a nanobot within the human body, said nanobot having at least one embedded biosensor, said biosensor which operates in real-time to continuously obtain data from within the human body;
integrating and/or embedding a visualization device within said nanobot to provide real-time visualization data in the human body;
transmitting data via a transmitter/receiver disposed on said nanobot, from said nanobot to an external transmitter/receiver, said transmitted data including said data from said biosensor and said data from said visualization device; and
receiving said data from said external transmitter/receiver of said nanobot at a processor of a computer system and analyzing said visualization data to determine said anatomic localization of said nanobot at a specific anatomic position within the human body.

20. The method of claim 19, further comprising:
analyzing said visualization data from said visualization device using a visualization module of said processor, with biologic and pathologic data from said biosensor, from one or more anatomic sites; and
creating a four-dimensional (4D) map using a mapping module of said processor;
wherein said mapping module combines said analysis from said visualization module to yield at least one of an anatomic, visualization, functional or pathologic 4D map which is continuously monitored by said processor to detect environmental changes at cellular and tissue levels at said specific anatomic position in the human body; and
wherein said visualization module combines said 4D map with external data from macroscopic imaging/visualization technologies to create a 4D visualization map.

* * * * *